US010578092B2

(12) United States Patent
Overson et al.

(10) Patent No.: US 10,578,092 B2
(45) Date of Patent: Mar. 3, 2020

(54) PRESSURE CONTROL GASKETS FOR OPERATING PUMP CASSETTE MEMBRANES

(71) Applicant: DEKA Products Limited Partnership, Manchester, NH (US)

(72) Inventors: Jason M. Overson, Manchester, NH (US); Daniel S. Karol, Southborough, MA (US); Jacob W. Scarpaci, Manchester, NH (US); John F. Mannisto, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 323 days.

(21) Appl. No.: 15/462,497

(22) Filed: Mar. 17, 2017

(65) Prior Publication Data

US 2017/0268495 A1 Sep. 21, 2017

Related U.S. Application Data

(60) Provisional application No. 62/310,361, filed on Mar. 18, 2016.

(51) Int. Cl.
*F04B 43/02* (2006.01)
*F04B 43/06* (2006.01)
(Continued)

(52) U.S. Cl.
CPC ............ *F04B 43/028* (2013.01); *F04B 43/06* (2013.01); *F04B 45/045* (2013.01); *F04B 45/053* (2013.01)

(58) Field of Classification Search
CPC ................. F16K 15/144; F16K 15/145; F04B 43/02–43/0736; F04B 45/04–45/0536
See application file for complete search history.

(56) References Cited

U.S. PATENT DOCUMENTS 356,997 A 2/1887 Gil
2,339,876 A 1/1944 Phillips
(Continued)

FOREIGN PATENT DOCUMENTS

WO WO 2012/006425 A2 1/2012

OTHER PUBLICATIONS

*International Search Report and Written Opinion* dated May 31, 2017, received in International Patent Application No. PCT/US2017/023046, 12 pgs.

*Primary Examiner* — Bryan M Lettman
(74) *Attorney, Agent, or Firm* — Marc J. Gorayeb

(57) ABSTRACT

A pump cassette comprising an outer flexible membrane covering flowpaths, valve chambers and pump chambers of the cassette is designed to be actuated by a control gasket on a base unit arranged to move designated valve and pump portions of the cassette membrane. The performance of a cassette valve may improved by optimizing the configuration of the valve control region of the control gasket overlying the cassette valve. This may improve both fluid flow through the valve and reduce the amount of vibratory noise associated with opening the valve. The gasket valve control or actuation region is at least partially bounded by a vacuum channel facing the outside of the gasket so that a constant vacuum can be applied between the gasket valve control or actuation region and the adjacent portion of the cassette membrane. An improved version of the vacuum channel comprises a flexible inner wall (contiguous with the valve control region) so that the inner wall flexes or partially collapses away from the cassette valve seat, while still maintaining patency of the vacuum channel during the application of negative pressure on the gasket valve actuation region to open the cassette valve.

10 Claims, 32 Drawing Sheets

(51) Int. Cl.
*F04B 45/053* (2006.01)
*F04B 45/04* (2006.01)

(56) References Cited

U.S. PATENT DOCUMENTS

| | | | |
|---|---|---|---|
| 3,083,943 A | | 4/1963 | Stewart, Jr. et al. |
| 4,086,036 A | * | 4/1978 | Hagen .................. F04B 43/0054 417/413.1 |
| 4,222,127 A | | 9/1980 | Donachy et al. |
| 4,416,599 A | * | 11/1983 | De Longchamp .... F04B 43/067 417/386 |
| 4,452,572 A | * | 6/1984 | Evrard .................... F04B 37/14 417/395 |
| 4,662,829 A | * | 5/1987 | Nehring .................. F04B 43/06 417/395 |
| 4,741,678 A | * | 5/1988 | Nehring .................. F04B 43/06 417/395 |
| 4,881,876 A | * | 11/1989 | Laziou .................. F04B 43/009 417/63 |
| 5,002,471 A | * | 3/1991 | Perlov ................. F04B 43/0054 417/413.1 |
| 5,098,262 A | | 3/1992 | Wecker et al. |
| 5,350,357 A | | 9/1994 | Kamen et al. |
| 5,593,290 A | | 1/1997 | Greisch et al. |
| 5,704,520 A | | 1/1998 | Gross |
| 5,755,683 A | | 5/1998 | Houle et al. |
| 5,938,634 A | | 8/1999 | Packard |
| 5,961,305 A | | 10/1999 | Eek et al. |
| 5,983,777 A | * | 11/1999 | Cassaday ............ F04B 43/0063 92/13.2 |
| 6,295,918 B1 | | 10/2001 | Simmons et al. |
| 6,604,908 B1 | | 8/2003 | Bryant et al. |
| 6,877,419 B2 | | 4/2005 | Ohrle et al. |
| 6,953,323 B2 | | 10/2005 | Childers et al. |
| 8,246,826 B2 | | 8/2012 | Wilt et al. |
| 8,292,594 B2 | | 10/2012 | Tracey et al. |
| 8,366,655 B2 | | 2/2013 | Kamen et al. |
| 8,545,195 B2 | * | 10/2013 | Barton ................ H01M 8/0606 417/269 |
| 8,708,950 B2 | | 4/2014 | Scarpaci et al. |
| 8,715,235 B2 | | 5/2014 | Childers et al. |
| 9,078,971 B2 | | 7/2015 | Scarpaci et al. |
| 9,248,225 B2 | | 2/2016 | Demers et al. |
| 9,302,039 B2 | | 4/2016 | Kelly et al. |
| 9,517,295 B2 | | 12/2016 | Wilt et al. |
| 2003/0194332 A1 | * | 10/2003 | Jahn .................. F04B 43/0733 417/395 |
| 2004/0001766 A1 | | 1/2004 | Maianti et al. |
| 2004/0019313 A1 | | 1/2004 | Childers et al. |
| 2005/0074340 A1 | * | 4/2005 | Xu ........................ F04B 19/006 417/395 |
| 2005/0095154 A1 | | 5/2005 | Tracey et al. |
| 2005/0115402 A1 | * | 6/2005 | Hembree ............ F04B 43/0054 92/96 |
| 2005/0126998 A1 | | 6/2005 | Childers |
| 2006/0195064 A1 | | 8/2006 | Plahey et al. |
| 2007/0253463 A1 | * | 11/2007 | Perry .................... A61M 1/369 374/208 |
| 2008/0077068 A1 | * | 3/2008 | Orr .......................... F04B 7/02 604/6.11 |
| 2008/0202591 A1 | * | 8/2008 | Grant .................. A61M 1/1639 137/12 |
| 2008/0216898 A1 | * | 9/2008 | Grant .................. A61M 1/1037 137/154 |
| 2009/0012448 A1 | | 1/2009 | Childers et al. |
| 2013/0165847 A1 | | 6/2013 | Scarpaci et al. |

\* cited by examiner

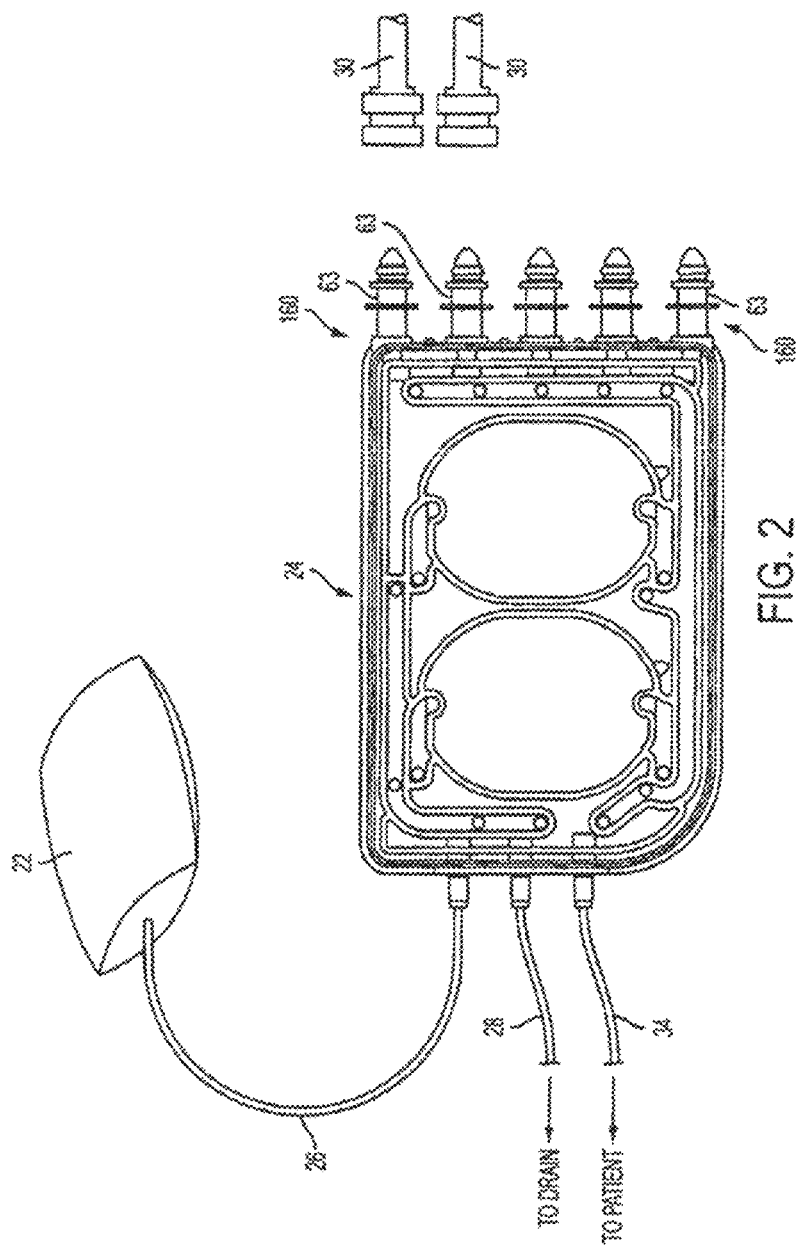

PRESSURE CONTROL GASKETS FOR OPERATING PUMP CASSETTE MEMBRANES

CROSS REFERENCE TO RELATED APPLICATIONS

The present application is a Non-Provisional application which claims the benefit of U.S. Provisional Patent Application Ser. No. 62/310,361, filed Mar. 18, 2016 and entitled Pressure Control Gaskets for Operating Pump Cassette Membranes, which is hereby incorporated herein by reference in its entirety.

BACKGROUND

Fluid handling devices (an example of which is described herein as a base unit) can be configured to receive fluid pumping cassettes to actuate membrane-based pumps and valves on the cassette, with a goal of delivering fluid from various sources to various destinations. An advantage of such a system is that the cassette can be discarded after a single use, obviating the need for sterilization and packaging for reuse, and the fluid handling device can remain free from contact with the fluids being processed. Such a system can be used in any application in which fluid pumping is needed and in which disposable fluid-carrying components (such as pump cassettes) are desirable. This is particularly useful in the medical field, because cleaning and sterilization procedures for repeated use of certain fluid-exposed equipment can be expensive, unreliable, and may result in a reduced lifespan of the equipment. Disposable membrane-based pumping cassettes can be used in many medical applications, including, for example, IV infusion devices, extracorporeal blood handling devices, hemodialysis/hemoperfusion devices, body cavity irrigation devices, and automated peritoneal dialysis devices. This technology can similarly be applied to non-medical fluid handling systems in various industries, including biotechnology.

Pumping cassettes may comprise self-enclosed units that include both a fluid flowpath side and an actuation side (commonly pneumatic actuation of membrane-based pumps and valves), the actuation side having one or more attached diaphragms to operate the pumps and valves. The cassettes have ports for connection to fluid sources and destinations. The actuation side of the cassette is configured to be coupled or mated to pressure actuation sources (potentially hydraulic, but more typically pneumatic). Pumping cassettes may also comprise relatively flat, thin housings that include fluid pathways, occludable valve orifices to control the direction of fluid flow in the cassette, and the pumping chamber portion of one or more membrane-based pumps. In one version, these cassettes are typically covered on one or both sides with a flexible membrane fused to the perimeter of the cassette, providing a liquid seal between the fluid paths within the cassette and the outside environment. Both the on-board pumping chambers and valves are operated by having a base unit provide actuation pressure (both positive and negative pressure) to pump actuation regions and valve actuation regions of the outer cassette membrane facing the base unit. This actuation pressure can be delivered by a valved manifold connected to positive and negative pressure sources (e.g. tanks pressurized by separate pumps). The valved manifold can be configured to deliver positive or negative pressure to an installed pump cassette through the use of controller-driven electromechanical valves installed in the manifold. The manifold can deliver the actuation pressure to various valves and pumps of the installed cassette through a pressure delivery block that mates with the cassette, which when mated with adequate force, seals the cassette membrane against various walls defining flowpaths, valves and pumps in the cassette to form sealed fluid flowpaths within the cassette. The pressure delivery block includes pneumatic ports that align with the locations of various valves and pumps on the cassette.

In some embodiments, a gasket can be positioned against the face of the pressure delivery block, the gasket having elastomeric actuation regions that mate with corresponding regions on a cassette membrane when the cassette is installed on the base unit. In this arrangement, the pressure delivery block may also include vacuum ports that penetrate the gasket near the control regions so that a constant vacuum can be applied between the gasket and the membrane of an installed cassette, so that movement of a gasket control region toward or away from the pressure delivery block can be mimicked by the corresponding region of the cassette membrane. The gasket placed over the pressure delivery block can be made of rubber or other elastomeric material, and can provide the method of sealing the cassette membrane against the cassette. The separate pump and valve control regions can be made of the same material, but with varying degrees of thickness or various profiles to deliver positive or negative pressure to the corresponding pump and valve regions of the cassette membrane. The features are designed to form a tight seal between the cassette membrane and the actuation regions of the gasket, so that both outward and inward movement of the control regions of the gasket are followed closely by the adjacent actuation portions of the cassette membrane. Opening and closing of cassette valves, and filling and delivery strokes of the cassette pumps can thus be performed effectively. The control gasket also serves to protect the passageways of the pressure delivery block and the manifold from fluid infiltration should any part of the membrane of an installed cassette fail or become torn or punctured. In medical applications, the interposition of a gasket between the pressure source (air or fluid) and the cassette provides an important safety feature that prevents the actuation fluid or air from being delivered to a cassette (and then possibly to a patient) if the cassette has a punctured or torn membrane.

The way in which the pump and valve control regions of the control gasket are formed and shaped affects the efficiency of fluid pumping by the cassette, and may also affect how accurately the system controller can measure fluid flows in the cassette. The way in which the valve control regions of the control gasket are formed may also affect how much noise or vibration is generated by the pumping system during operation. In the following description, an automated peritoneal dialysis system is used as an example of the implementation these features, but the same principles and solutions can be applied to any fluid handling device—medical or non-medical—that uses membrane-based pump cassettes to move fluid.

SUMMARY

A fluid pumping system comprises a pumping cassette that comprises a generally planar body having one or more depressions to form one or more pump chambers, a plurality of fluid flowpaths defined by rigid walls in the body, and a plurality of valves comprising valve orifices defined by raised valve seats in the body. The pumping cassette has a flexible membrane affixed to a face of the body overlying the depressions, flowpaths and valve orifices. A base unit is arranged to receive the pumping cassette and to provide positive or negative pressure to the flexible membrane to operate the one or more pump chambers and the plurality of valves. A control gasket is positioned over a pressure delivery block of the base unit, the control gasket having valve and pump control regions arranged to move toward or away from the pressure delivery block under force of positive or negative pressure transmitted through passageways in the pressure delivery block. The valve control regions are positioned adjacent corresponding valve control regions of the flexible membrane of the cassette, and opposite valve seats of the plurality of valves in the cassette. Portions of the control gasket not comprising valve or pump control regions are arranged to provide a sealing engagement of the flexible membrane against the rigid walls of the body, these portions of the control gasket lying in a plane of the control gasket.

In an embodiment, the gasket has a first side configured for placement against a pressure delivery block and having an opposing second side configured for placement against a flexible cassette membrane overlying the pump cassette, the gasket having a main body and an elastomeric valve actuation region that moves outward toward the cassette under positive pressure and inward toward the pressure delivery block under negative pressure. The valve actuation region is configured to be positioned adjacent a valve actuation portion of the cassette membrane overlying a cassette valve of the pump cassette. The valve actuation region comprises a central portion configured to align with and to be pressed against a valve seat defining an orifice of the cassette valve; a peripheral portion configured to extend over a valve chamber of the pump cassette surrounding the valve orifice; and a vacuum channel forming a perimeter around at least a portion of the peripheral portion of the actuation region, the vacuum channel defined by an inner wall contiguous with the peripheral portion of the actuation region, a floor, and an outer wall contiguous with or formed from the main body of the gasket, the vacuum channel being open to the second side of the gasket. The vacuum channel is fluidically connected to a vacuum port in the gasket that penetrates from the second side to the first side of the gasket, the vacuum port configured to communicate with a corresponding pressure delivery block vacuum port when the gasket is positioned against the pressure delivery block. And the inner wall of the vacuum channel is configured to flex toward the pressure delivery block when the gasket valve actuation region is placed under negative pressure, at least partially collapsing the inner wall of the vacuum channel while the valve actuation region moves inward and is pulled away from the cassette valve orifice when the pump cassette is present against the gasket.

The seat of the cassette valve seat may comprise a raised circumferential wall, and the gasket valve actuation region may be configured to press the cassette membrane against the circumferential wall to occlude or close the cassette valve. The vacuum channel of the valve actuation region may be configured to be positioned outside the circumferential wall of the valve seat and over a well or chamber of the cassette valve. And the inner and outer walls of the vacuum channel may be configured to apply pressure between the valve actuation region and the valve seat when the first side of the valve actuation region is exposed to atmospheric pressure and the pump cassette is placed against the gasket.

In another embodiment, a fluid pumping system comprises a pump cassette comprising a flexible membrane and a membrane based valve; a base pumping unit comprising a source of positive or negative pressure, a pressure distribution manifold, and a pressure delivery block configured to be positioned adjacent the cassette membrane and valve. A gasket is configured for placement between the pressure delivery block and the cassette membrane, a first side of the gasket positioned against the pressure delivery block and a second opposing side of the gasket positioned against the cassette, the gasket comprising an elastomeric valve actuation region for positioning against the cassette membrane and valve. The pressure delivery block comprises a control port for delivering positive pressure to the valve actuation region to move the cassette membrane against a valve seat of the cassette valve, and for delivering negative pressure to the valve actuation region to move the cassette membrane away from the valve seat of the cassette valve. The gasket comprises a vacuum channel forming a perimeter around at least a portion of the valve actuation region, the vacuum channel defined by an inner wall contiguous with the valve actuation region, a floor, and an outer wall contiguous with or formed from a non-actuation region of the gasket surrounding the valve actuation region. The vacuum channel is in communication with a vacuum port in the gasket that penetrates from the second side to the first side of the gasket and that is aligned with a pressure delivery block vacuum port. And the inner wall of the vacuum channel is configured to flex toward the pressure delivery block when negative pressure is applied to the valve actuation region via the control port, and patency of the vacuum channel is maintained.

The positive or negative pressure may be pneumatic pressure. The vacuum channel may be positioned circumferentially around the periphery of the gasket valve actuation region. The cassette valve seat may comprise a raised circumferential wall, and the gasket valve actuation region may be configured to press the cassette membrane against the circumferential wall to occlude or close the cassette valve. The vacuum channel of the valve actuation region may be positioned outside the circumferential wall of the valve seat and over a well or chamber of the cassette valve. And the inner and outer walls of the vacuum channel may be configured to apply pressure between the valve actuation region and the valve seat when the first side of the valve actuation region is exposed to atmospheric or ambient pressure.

In another embodiment, a method is disclosed of opening or closing a pump cassette membrane valve comprising a flexible membrane overlying a valve seat of the pump cassette and using an elastomeric valve actuation region of a gasket placed between the flexible membrane of the pump cassette and a pressure delivery block. The method comprises: applying negative pressure via the pressure delivery block to an outer side of the gasket valve actuation region facing the cassette membrane via a vacuum channel located along a periphery of the valve actuation region and open to the outer side of the gasket valve actuation region; applying negative pressure via the pressure delivery block to an inner side of the gasket valve actuation region facing the pressure delivery block; flexing an outer wall of the vacuum channel toward the pressure delivery block and away from pump cassette valve seat, the outer wall being contiguous with the valve actuation region of the gasket; and maintaining patency of the vacuum channel so that the negative pressure applied to the outer side of the gasket valve actuation region is uninterrupted.

Applying negative pressure may comprise applying negative pneumatic pressure. Applying negative pressure to an outer side of the gasket valve actuation region may comprise delivering negative pressure via the vacuum channel circumferentially around the valve actuation region. And the method may further comprise closing the pump cassette membrane valve by applying positive pressure via the pressure delivery block to the inner side of the gasket valve actuation region against a raised wall of the valve seat surrounding an orifice of the pump cassette membrane valve.

BRIEF DESCRIPTION OF THE DRAWINGS

FIG. 2 is a schematic view of an illustrative set for use with the APD system of FIG. 1;

DETAILED DESCRIPTION

Automated Peritoneal Dialysis System

Figure 1:
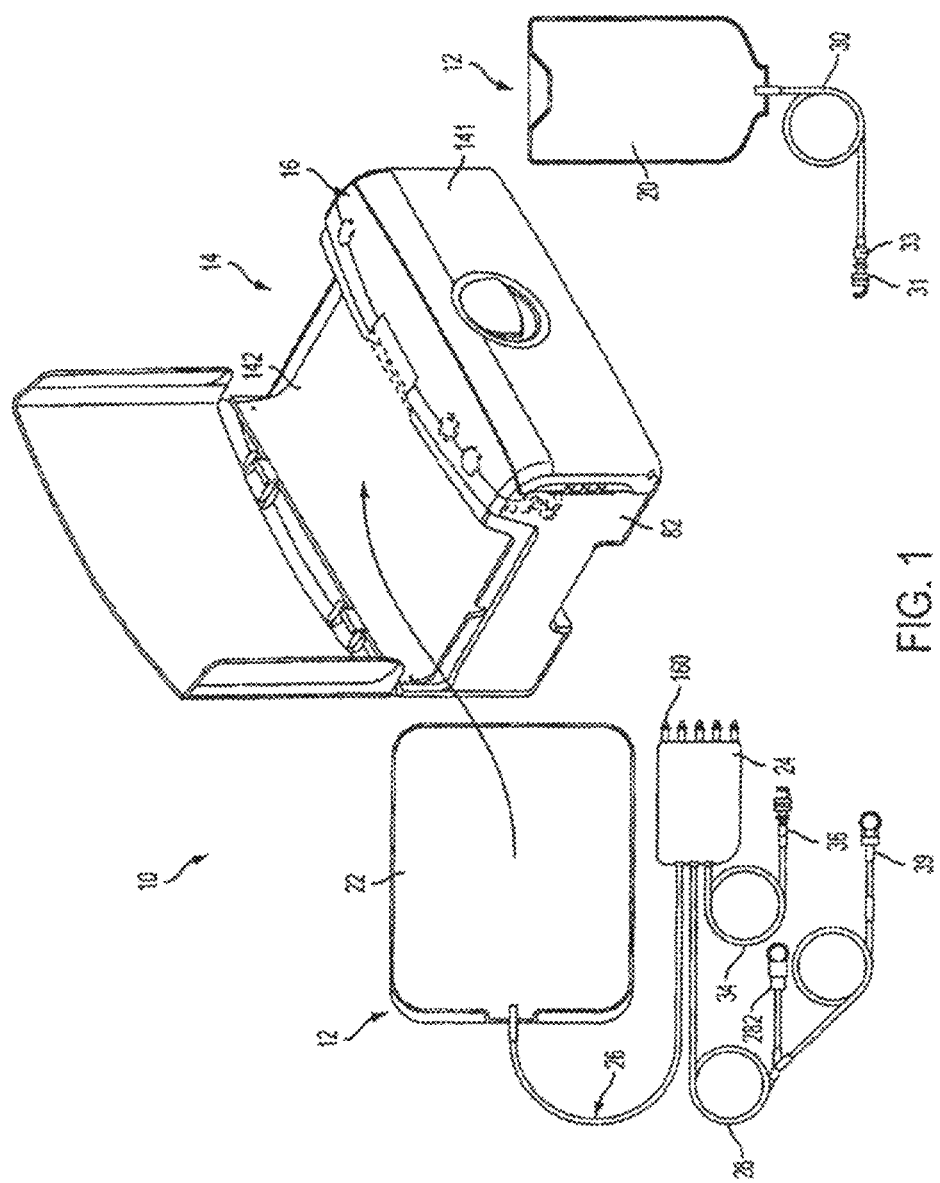
FIG. 1 shows a schematic view of an automated peritoneal dialysis (APD) system that incorporates one or more aspects of the invention.

FIG. 1 shows an automated peritoneal dialysis (APD) system 10 that encompasses one or more aspects of the invention. As shown in FIG. 1, for example, the system 10 in this illustrative embodiment includes a dialysate delivery set 12 (which, in certain embodiments, can be a disposable set), a cycler 14 that interacts with the delivery set 12 to pump liquid provided by a solution container 20 (e.g., a bag), and a control system 16 (e.g., including a programmed computer or other data processor, computer memory, an interface to provide information to and receive input from a user or other device, one or more sensors, actuators, relays, pneumatic pumps, tanks, a power supply, and/or other suitable components—only a few buttons for receiving user control input are shown in FIG. 1, but further details regarding the control system components are provided below) that governs the process to perform an APD procedure. In this illustrative embodiment, the cycler 14 and the control system 16 are associated with a common housing 82, but may be associated with two or more housings and/or may be separate from each other. The cycler 14 may have a compact footprint, suited for operation upon a table top or other relatively small surface normally found in the home. The cycler 14 may be lightweight and portable, e.g., carried by hand via handles at opposite sides of the housing 82.

The set 12 in this embodiment is intended to be a single use, disposable item, but instead may have one or more reusable components, or may be reusable in its entirety. The user associates the set 12 with the cycler 14 before beginning each APD therapy session, e.g., by mounting a cassette 24 within a front door 141 of the cycler 14, which interacts with the cassette 24 to pump and control fluid flow in the various lines of the set 12. For example, dialysate may be pumped both to and from the patient to effect APD. Post therapy, the user may remove all or part of the components of the set 12 from the cycler 14.

As is known in the art, prior to use, the user may connect a patient line 34 of the set 12 to his/her indwelling peritoneal catheter (not shown) at a connection 36. In one embodiment, the cycler 14 may be configured to operate with one or more different types of cassettes 24, such as those having differently sized patient lines 34. For example, the cycler 14 may be arranged to operate with a first type of cassette with a patient line 34 sized for use with an adult patient, and a second type of cassette with a patient line 34 sized for an infant or pediatric use. The pediatric patient line 34 may be shorter and have a smaller inner diameter than the adult line so as to minimize the volume of the line, allowing for more controlled delivery of dialysate and helping to avoid returning a relatively large volume of used dialysate to the pediatric patient when the set 12 is used for consecutive drain and fill cycles. A heater bag 22, which is connected to the cassette 24 by a line 26, may be placed on a heater container receiving portion (in this case, a tray) 142 of the cycler 14. The cycler 14 may pump fresh dialysate (via the cassette 24) into the heater bag 22 so that the dialysate may be heated by the heater tray 142, e.g., by electric resistance heating elements associated with the tray 142 to a temperature of about 37 degrees C. Heated dialysate may be provided from the heater bag 22 to the patient via the cassette 24 and the patient line 34. In an alternative embodiment, the dialysate can be heated on its way to the patient as it enters, or after it exits, the cassette 24 by passing the dialysate through tubing in contact with the heater tray 142, or through an in-line fluid heater (which may be provided in the cassette 24). Used dialysate may be pumped from the patient via the patient line 34 to the cassette 24 and into a drain line 28, which may include one or more clamps to control flow through one or more branches of the drain line 28. In this illustrative embodiment, the drain line 28 may include a connector 39 for connecting the drain line 28 to a dedicated drain receptacle, and an effluent sample port 282 for taking a sample of used dialysate for testing or other analysis. The user may also mount the lines 30 of one or more containers 20 within the door 141. The lines 30 may also be connected to a continuous or real-time dialysate preparation system. (The lines 26, 28, 30, 34 may include a flexible tubing and/or suitable connectors and other components (such as pinch valves, etc.) as desired.) The containers 20 may contain sterile peritoneal dialysis solution for infusion, or other materials (e.g., materials used by the cycler 14 to formulate dialysate by mixing with water, or admixing different types of dialysate solutions). The lines 30 may be connected to spikes 160 of the cassette 24, which are shown in FIG. 1 covered by removable caps.

In one aspect of the invention, the cycler 14 may automatically remove caps from one or more spikes 160 of the cassette 24 and connect lines 30 of solution containers 20 to respective spikes 160. This feature may help reduce the possibility of infection or contamination by reducing the chance of contact of non-sterile items with the spikes 160.

Figure 1A:
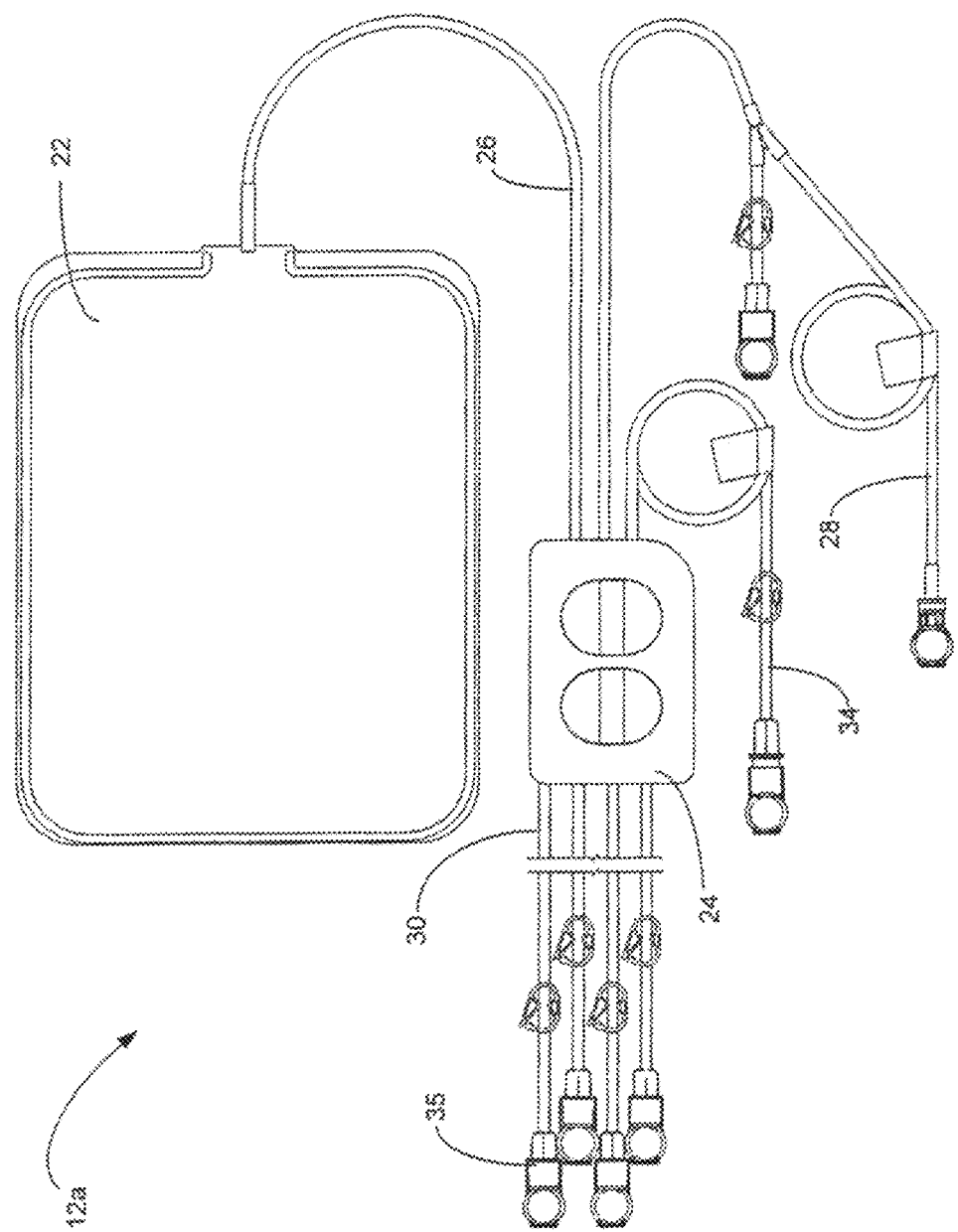
FIG. 1A shows an alternative arrangement for a dialysate delivery set shown in FIG. 1.

In another aspect, a dialysate delivery set 12a may not have cassette spikes 160. Instead, one or more solution lines 30 may be permanently affixed to the inlet ports of cassette 24, as shown in FIG. 1A. In this case, each solution line 30 may have a (capped) spike connector 35 for manual connection to a solution container or dialysate bag 20.

With various connections made, the control system 16 may pace the cycler 14 through a series of fill, dwell, and/or drain cycles typical of an APD procedure. For example, during a fill phase, the cycler 14 may pump dialysate (by way of the cassette 24) from one or more containers 20 (or other source of dialysate supply) into the heater bag 22 for heating. Thereafter, the cycler 14 may infuse heated dialysate from the heater bag 22 through the cassette 24 and into the patient's peritoneal cavity via the patient line 34. Following a dwell phase, the cycler 14 may institute a drain phase, during which the cycler 14 pumps used dialysate from the patient via the line 34 (again by way of the cassette 24), and discharges spent dialysis solution into a nearby drain (not shown) via the drain line 28.

The cycler 14 does not necessarily require the solution containers 20 and/or the heater bag 22 to be positioned at a prescribed head height above the cycler 14, e.g., because the cycler 14 is not necessarily a gravity flow system. Instead, the cycler 14 may emulate gravity flow, or otherwise suitably control flow of dialysate solution, even with the source solution containers 20 above, below or at a same height as the cycler 14, with the patient above or below the cycler, etc. For example, the cycler 14 can emulate a fixed head height during a given procedure, or the cycler 14 can change the effective head height to either increase or decrease pressure applied to the dialysate during a procedure. The cycler 14 may also adjust the rate of flow of dialysate. In one aspect of the invention, the cycler 14 may adjust the pressure and/or flow rate of dialysate when provided to the patient or drawn from the patient so as to reduce the patient's sensation of the fill or drain operation. Such adjustment may occur during a single fill and/or drain cycle, or may be adjusted across different fill and/or drain cycles. In one embodiment, the cycler 14 may taper the pressure used to draw used dialysate from the patient near the end of a drain operation. Because the cycler 14 may establish an artificial head height, it may have the flexibility to interact with and adapt to the particular physiology or changes in the relative elevation of the patient.

Cassette

In one aspect of the invention, a cassette 24 may include patient and drain lines that are separately occludable with respect to solution supply lines. That is, safety critical flow to and from patient line may be controlled, e.g., by pinching the lines to stop flow, without the need to occlude flow through one or more solution supply lines. This feature may allow for a simplified occluder device since occlusion may be performed with respect to only two lines as opposed to occluding other lines that have little or no effect on patient safety. For example, in a circumstance where a patient or drain connection becomes disconnected, the patient and drain lines may be occluded. However, the solution supply and/or heater bag lines may remain open for flow, allowing the cycler 14 to prepare for a next dialysis cycle; e.g., separate occlusion of patient and drain lines may help ensure patient safety while permitting the cycler 14 to continue to pump dialysate from one or more containers 20 to the heater bag 22 or to other solution containers 20.

In another aspect of the invention, the cassette may have patient, drain and heater bag lines at one side or portion of the cassette and one or more solution supply lines at another side or portion of the cassette, e.g., an opposite side of the cassette. Such an arrangement may allow for separate occlusion of patient, drain or heater bag lines with respect to solution lines as discussed above. Physically separating the lines attached to the cassette by type or function allows for more efficient control of interaction with lines of a certain type or function. For example, such an arrangement may allow for a simplified occluder design because less force is required to occlude one, two or three of these lines than all lines leading to or away from the cassette. Alternately, this arrangement may allow for more effective automated connection of solution supply lines to the cassette, as discussed in more detail below. That is, with solution supply lines and their respective connections located apart from patient, drain and/or heater bag lines, an automated de-capping and connection device may remove caps from spikes on the cassette as well as caps on solution supply lines, and connect the lines to respective spikes without interference by the patient, drain or heater bag lines.

FIG. 2 shows an illustrative embodiment of a cassette 24 that incorporates aspects of the invention described above. In this embodiment, the cassette 24 has a generally planar body and the heater bag line 26, the drain line 28 and the patient line 34 are connected at respective ports on the left end of the cassette body, while the right end of the cassette body may include five spikes 160 to which solution supply lines 30 may be connected. In the arrangement shown in FIG. 2, each of the spikes 160 is covered by a spike cap 63, which may be removed, exposing the respective spike and allowing connection to a respective line 30. As described above, the lines 30 may be attached to one or more solution containers or other sources of material, e.g., for use in dialysis and/or the formulation of dialysate, or connected to one or more collection bags for sampling purposes or for peritoneal equilibration testing (PET test).

Figure 3:
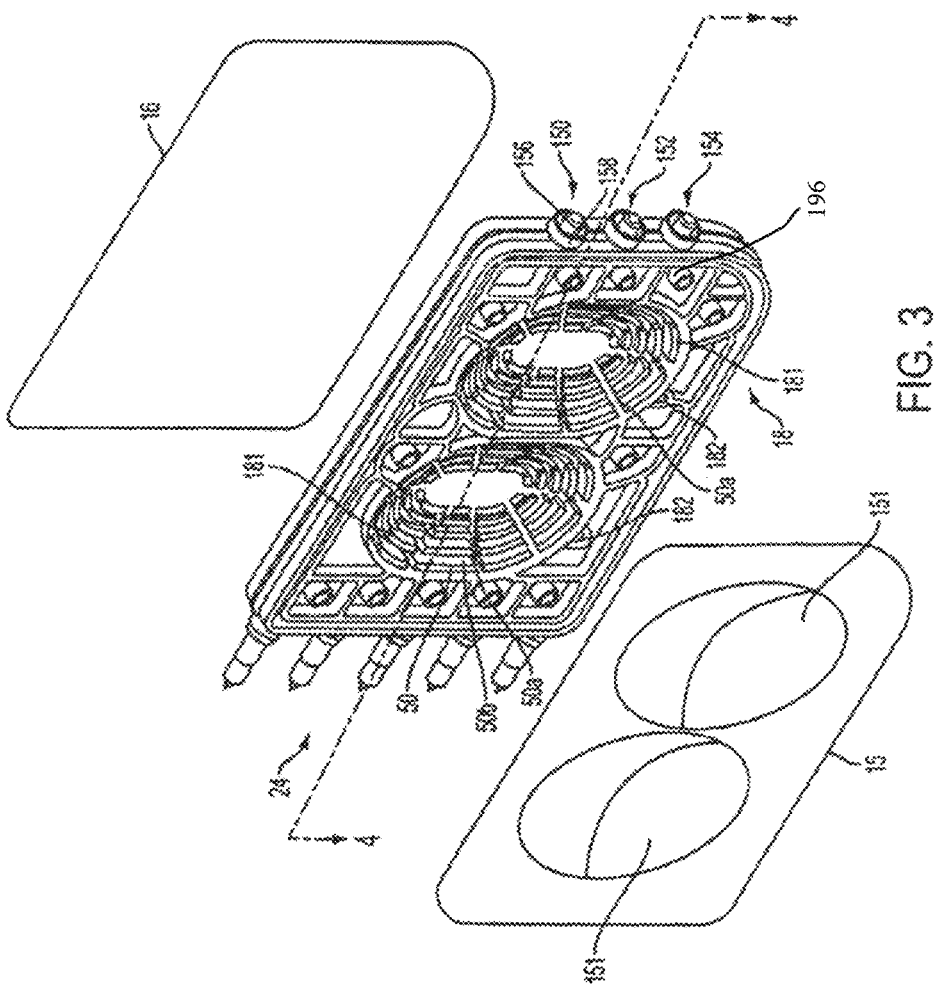
FIG. 3 is an exploded perspective view of a cassette in a first embodiment.
Figure 4:
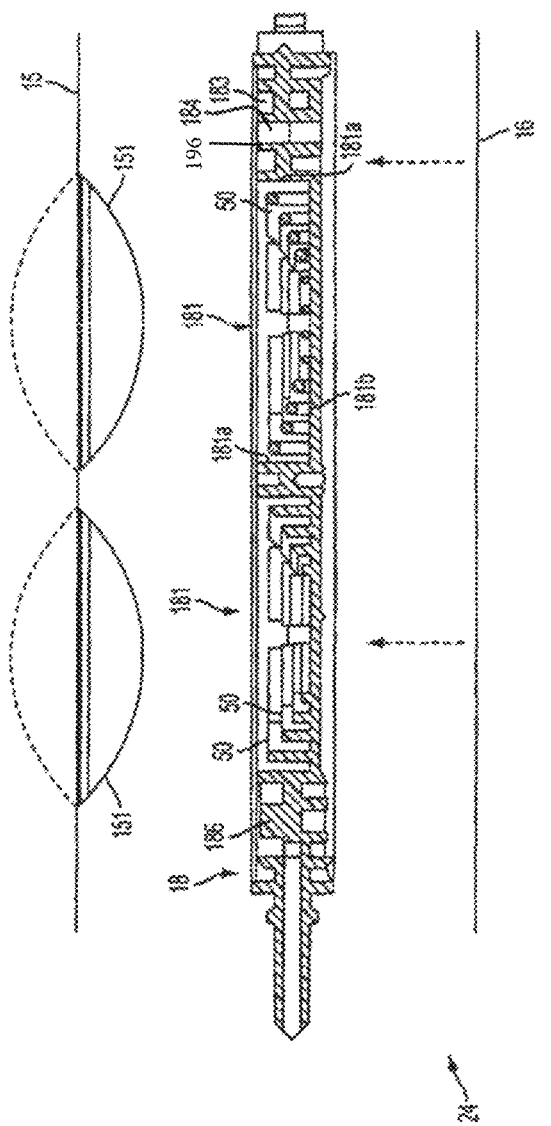
FIG. 4 is a cross sectional view of the cassette along the line 4-4 in FIG. 3.

FIGS. 3 and 4 show exploded views (perspective and top views, respectively) of the cassette 24 in this illustrative embodiment. The cassette 24 is formed as a relatively thin and flat member having a generally planar shape, e.g., may include components that are molded, extruded or otherwise formed from a suitable plastic. In this embodiment, the cassette 24 includes a base member 18 that functions as a frame or structural member for the cassette 24 as well as forming, at least in part, various flow channels, ports, valve portions, etc. The base member 18 may be molded or otherwise formed from a suitable plastic or other material, such as a polymethyl methacrylate (PMMA) acrylic, or a cyclic olefin copolymer/ultra low density polyethylene (COC/ULDPE), and may be relatively rigid. In an embodiment, the ratio of COC to ULDPE can be approximately 85%/15%. FIG. 3 also shows the ports for the heater bag (port 150), drain (port 152) and the patient (port 154) that are formed in the base member 18. Each of these ports may be arranged in any suitable way, such as, for example, a central tube 156 extending from an outer ring or skirt 158, or a central tube alone. Flexible tubing for each of the heater bag, drain and patient lines 26, 28, 34 may be connected to the central tube 156 and engaged by the outer ring 158, if present.

Both sides of the base member 18 may be covered, at least in part, by a membrane 15 and 16, e.g., a flexible polymer film made from, for example, polyvinyl chloride (PVC), that is cast, extruded or otherwise formed. Alternatively, the sheet may be formed as a laminate of two or more layers of poly-cyclohexylene dimethylene cyclohexanedicarboxylate (PCCE) and/or ULDPE, held together, for example, by a coextrudable adhesive (CXA). In some embodiments, the membrane thickness may be in the range of approximately 0.002 to 0.020 inches thick. In a preferred embodiment, the thickness of a PVC-based membrane may be in the range of approximately 0.012 to 0.016 inches thick, and more preferably approximately 0.014 inches thick. In another preferred embodiment, such as, for example, for laminate sheets, the thickness of the laminate may be in the range of approximately 0.006 to 0.010 inches thick, and more preferably approximately 0.008 inches thick.

Both membranes 15 and 16 may function not only to close or otherwise form a part of flowpaths of the cassette 24, but also may be moved or otherwise manipulated to open/close valve ports and/or to function as part of a pump diaphragm, septum or wall that moves fluid in the cassette 24. For example, the membranes 15 and 16 may be positioned on the base member 18 and sealed (e.g., by heat, adhesive, ultrasonic welding or other means) to a rim around the periphery of the base member 18 to prevent fluid from leaking from the cassette 24. The membrane 15 may also be bonded to other, inner walls of the base member 18, e.g., those that form various channels, or may be pressed into sealing contact with the walls and other features of the base member 18 when the cassette 24 suitably mounted in the cycler 14. Thus, both of the membranes 15 and 16 may be sealed to a peripheral rim of the base member 18, e.g., to help prevent leaking of fluid from the cassette 24 upon its removal from the cycler 14 after use, yet be arranged to lie, unattached, over other portions of the base member 18. Once placed in the cycler 14, the cassette 24 may be squeezed between opposed gaskets or other members so that the membranes 15 and 16 are pressed into sealing contact with the base member 18 at regions inside of the periphery, thereby suitably sealing channels, valve ports, etc., from each other.

Other arrangements for the membranes 15 and 16 are possible. For example, the membrane 16 may be formed by a rigid sheet of material that is bonded or otherwise made integral with the body 18. Thus, the membrane 16 need not necessarily be, or include, a flexible member. Similarly, the membrane 15 need not be flexible over its entire surface, but instead may include one or more flexible portions to permit pump and/or valve operation, and one or more rigid portions, e.g., to close flowpaths of the cassette 24. It is also possible that the cassette 24 may not include the membrane 16 or the membrane 15, e.g., where the cycler 14 includes a suitable member to seal pathways of the cassette, control valve and pump function, etc.

Figure 5:
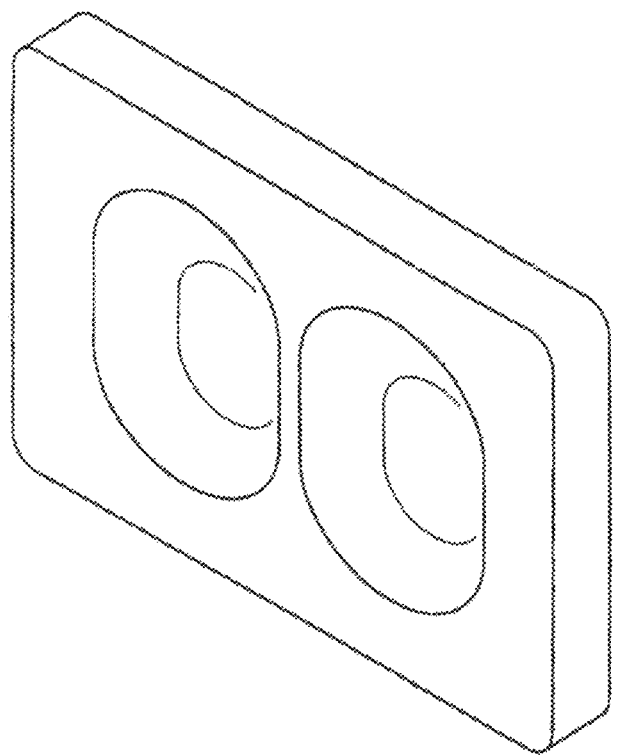
FIG. 5 is a perspective view of a vacuum mold that may be used to form a membrane having pre-formed pump chamber portions in an illustrative embodiment.

In accordance with another aspect of the invention, the membrane 15 may include a pump chamber portion 151 ("pump membrane") that is formed to have a shape that closely conforms to the shape of a corresponding pump chamber 181 depression in the base 18. For example, the membrane 15 may be generally formed as a flat member with thermoformed (or otherwise formed) dome-like shapes 151 that conform to the pump chamber depressions of the base member 18. The dome-like shape of the pre-formed pump chamber portions 151 may be constructed, for example, by heating and forming the membrane over a vacuum form mold of the type shown in FIG. 5. As shown in FIG. 5, the vacuum may be applied through a collection of holes along the wall of the mold. Alternatively, the wall of the mold can be constructed of a porous gas-permeable material, which may result in a more uniformly smooth surface of the molded membrane. In one example, the molded membrane sheet 15 is trimmed while attached to the vacuum form mold. The vacuum form mold then presses the trimmed membrane sheet 15 against the cassette body 18 and bonds them together. In one embodiment the membrane sheets 15, 16 are heat-welded to the cassette body 18. In this way, the membrane 15 may move relative to the pump chambers 181 to effect pumping action without requiring stretching of the membrane 15 (or at least minimal stretching of the membrane 15), both when the membrane 15 is moved maximally into the pump chambers 181 and (potentially) into contact with spacer elements 50 (e.g., as shown in solid line in FIG. 4 while pumping fluid out of the pump chamber 181), and when the membrane 15 is maximally withdrawn from the pump chamber 181 (e.g., as shown in dashed line in FIG. 4 when drawing fluid into the pump chamber 181). Avoiding stretching of the membrane 15 may help prevent pressure surges or other changes in fluid delivery pressure due to sheet stretch and/or help simplify control of the pump when seeking to minimize pressure variation during pump operation. Other benefits may be found, including reduced likelihood of membrane 15 failure (e.g., due to tears in the membrane 15 resulting from stresses place on the membrane 15 during stretching), and/or improved accuracy in pump delivery volume measurement, as described in more detail below. In one embodiment, the pump chamber portions 151 may be formed to have a size (e.g., a define a volume) that is about 85-110% of the pump chamber 181, e.g., if the pump chamber portions 151 define a volume that is about 100% of the pump chamber volume, the pump chamber portion 151 may lie in the pump chamber 181 and in contact with the spacers 50 while at rest and without being stressed.

Providing greater control of the pressure used to generate a fill and delivery stroke of liquid into and out of a pump chamber may have several advantages. For example, it may be desirable to apply the minimum negative pressure possible when the pump chamber draws fluid from the patient's peritoneal cavity during a drain cycle. A patient may experience discomfort during the drain cycle of a treatment in part because of the negative pressure being applied by the pumps during a fill stroke. The added control that a preformed membrane can provide to the negative pressure being applied during a fill stroke may help to reduce the patient's discomfort.

A number of other benefits may be realized by using pump membranes pre-formed to the contour of the cassette pump chamber. For example, the flow rate of liquid through the pump chamber can be made more uniform, because a constant pressure or vacuum can be applied throughout the pump stroke, which in turn may simplify the process of regulating the heating of the liquid. Moreover, temperature changes in the cassette pump may have a smaller effect on the dynamics of displacing the membrane, as well as the accuracy of measuring pressures within the pump chambers. In addition, pressure spikes within the fluid lines can be minimized. Also, correlating the pressures measured by pressure transducers on the control (e.g. pneumatic) side of the membrane with the actual pressure of the liquid on the pump chamber side of the membrane may be simpler. This in turn may permit more accurate head height measurements of the patient and fluid source bags prior to therapy, improve the sensitivity of detecting air in the pump chamber, and improve the accuracy of volumetric measurements. Furthermore, eliminating the need to stretch the membrane may allow for the construction and use of pump chambers having greater volumes.

In this embodiment, the cassette 24 includes a pair of pump chambers 181 that are formed in the base member 18, although one pump chamber or more than two pump chambers are possible. In accordance with an aspect of the invention, the inner wall of pump chambers 181 includes spacer elements 50 that are spaced from each other and extend from the inner wall of pump chamber 18 to help prevent portions of the membrane 15 from contacting the inner wall of pump chamber 181. (As shown on the right-side pump chamber 181 in FIG. 4, the inner wall is defined by side portions 181a and a bottom portion 181b. The spacers 50 extend upwardly from the bottom portion 181b in this embodiment, but could extend from the side portions 181a or be formed in other ways.) By preventing contact of the membrane 15 with the pump chamber inner wall, the spacer elements 50 may provide a dead space (or trap volume) which may help trap air or other gas in the pump chamber 181 and inhibit the gas from being pumped out of the pump chamber 181 in some circumstances. In other cases, the spacers 50 may help the gas move to an outlet of the pump chamber 181 so that the gas may be removed from the pump chamber 181, e.g., during priming. Also, the spacers 50 may help prevent the membrane 15 from sticking to the pump chamber inner wall and/or allow flow to continue through the pump chamber 181, even if the membrane 15 is pressed into contact with the spacer elements 50. In addition, the spacers 50 help to prevent premature closure of the outlet port of the pump chamber (openings 187 and/or 191) if the sheet happens to contact the pump chamber inner wall in a non-uniform manner. Further details regarding the arrangement and/or function of spacers 50 are provided in U.S. Pat. Nos. 6,302,653 and 6,382,923, both of which are incorporated herein by reference.

In this embodiment, the spacer elements 50 are arranged in a kind of "stadium seating" arrangement such that the spacer elements 50 are arranged in a concentric elliptical pattern with ends of the spacer elements 50 increasing in height from the bottom portion 181b of the inner wall with distance away from the center of the pump chamber 181 to form a semi-elliptical domed shaped region (shown by dotted line in FIG. 4). Positioning spacer elements 50 such that the ends of the spacer elements 50 form a semi-elliptical region that defines the domed region intended to be swept by the pump chamber portion 151 of the membrane 15 may allow for a desired volume of dead space that minimizes any reduction to the intended stroke capacity of pump chambers 181. As can be seen in FIG. 3 (and FIG. 6), the "stadium seating" arrangement in which spacer elements 50 are arranged may include "aisles" or breaks 50a in the elliptical pattern. Breaks (or aisles) 50a help to maintain an equal gas level throughout the rows (voids or dead space) 50b between spacer elements 50 as fluid is delivered from the pump chamber 181. For example, if the spacer elements 50 were arranged in the stadium seating arrangement shown in FIG. 6 without breaks (or aisles) 50a or other means of allowing liquid and air to flow between spacer elements 50, the membrane 15 might bottom out on the spacer element 50 located at the outermost periphery of the pump chamber 181, trapping whatever gas or liquid is present in the void between this outermost spacer element 50 and the side portions 181a of the pump chamber wall. Similarly, if the membrane 15 bottomed out on any two adjacent spacer elements 50, any gas and liquid in the void between the elements 50 may become trapped. In such an arrangement, at the end of the pump stroke, air or other gas at the center of pump chamber 181 could be delivered while liquid remains in the outer rows. Supplying breaks (or aisles) 50a or other means of fluidic communication between the voids between spacer elements 50 helps to maintain an equal gas level throughout the voids during the pump stroke, such that air or other gas may be inhibited from leaving the pump chamber 181 unless the liquid volume has been substantially delivered.

In certain embodiments, spacer elements 50 and/or the membrane 15 may be arranged so that the membrane 15 generally does not wrap or otherwise deform around individual spacers 50 when pressed into contact with them, or otherwise extend significantly into the voids between spacers 50. Such an arrangement may lessen any stretching or damage to membrane 15 caused by wrapping or otherwise deforming around one or more individual spacer elements 50. For example, it has also been found to be advantageous in this embodiment to make the size of the voids between spacers 50 approximately equal in width to the width of the spacers 50. This feature has shown to help prevent deformation of the membrane 15, e.g., sagging of the membrane into the voids between spacers 50, when the membrane 15 is forced into contact with the spacers 50 during a pumping operation.

In accordance with another aspect of the invention, the inner wall of pump chambers 181 may define a depression that is larger than the space, for example a semi-elliptical or domed space, intended to be swept by the pump chamber portion 151 of the membrane 15. In such instances, one or more spacer elements 50 may be positioned below the domed region intended to be swept by the membrane portion 151 rather than extending into that domed region. In certain instances, the ends of spacer elements 50 may define the periphery of the domed region intended to be swept by the membrane 15. Positioning spacer elements 50 outside of, or adjacent to, the periphery of the domed region intended to be swept by the membrane portion 151 may have a number of advantages. For example, positioning one or more spacer elements 50 such that the spacer elements are outside of, or adjacent to, the domed region intended to be swept by the flexible membrane provides a dead space between the spacers and the membrane, such as described above, while minimizing any reduction to the intended stroke capacity of pump chambers 181.

Figure 6:
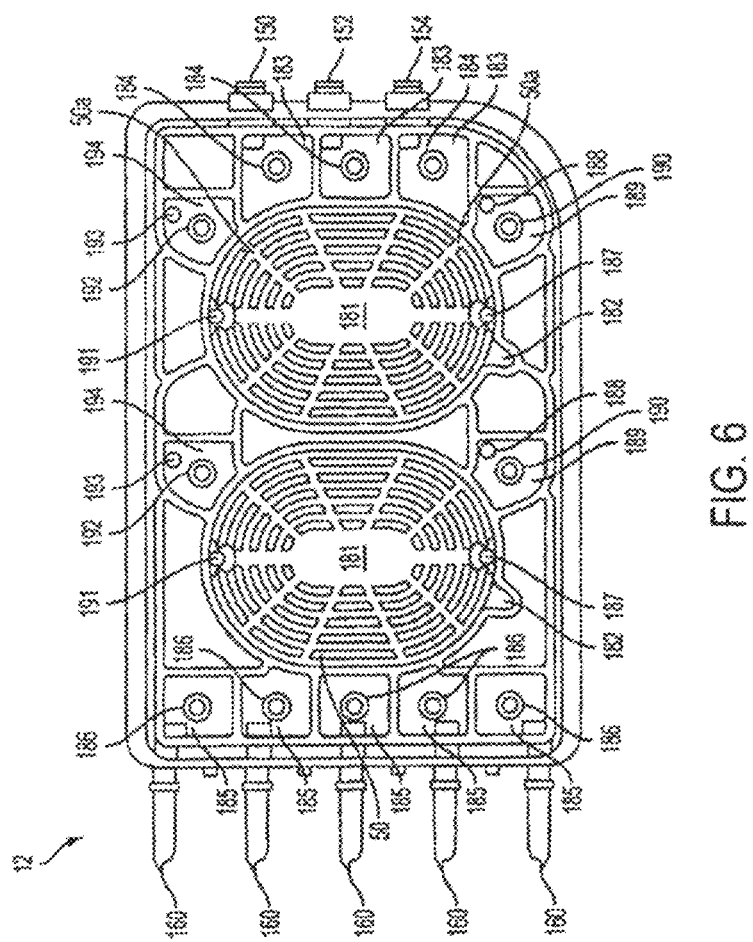
FIG. 6 shows a front view of the cassette body of FIG. 3.
Figure 7:
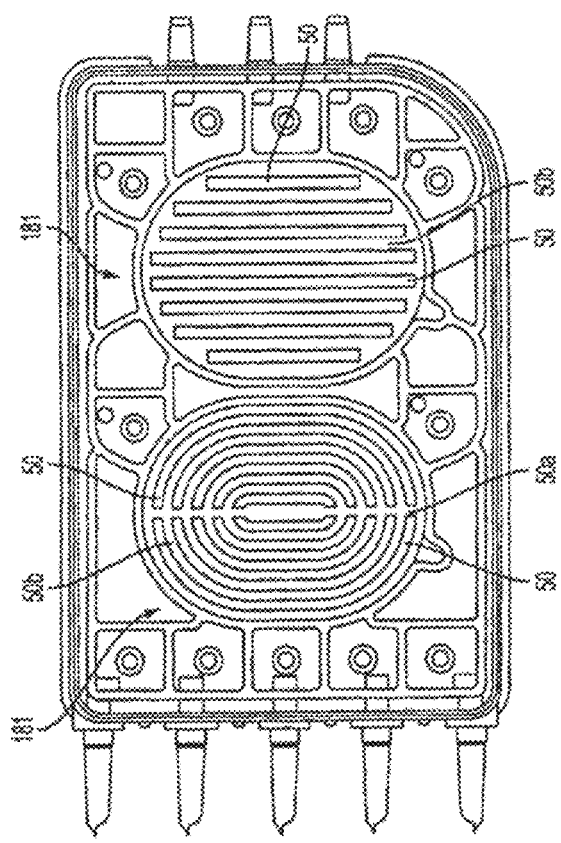
FIG. 7 is a front view of a cassette body including two different spacer arrangements in an illustrative embodiment.

It should be understood that the spacer elements 50, if present, in a pump chamber may be arranged in any other suitable way, such as for example, shown in FIG. 7. The left side pump chamber 181 in FIG. 7 includes spacers 50 arranged similarly to that in FIG. 6, but there is only one break or aisle 50a that runs vertically through the approximate center of the pump chamber 181. The spacers 50 may be arranged to define a concave shape similar to that in FIG. 6 (i.e., the tops of the spacers 50 may form the semi-elliptical shape shown in FIGS. 3 and 4), or may be arranged in other suitable ways, such as to form a spherical shape, a box-like shape, and so on. The right-side pump chamber 181 in FIG. 7 shows an embodiment in which the spacers 50 are arranged vertically with voids 50b between spacers 50 also arranged vertically. As with the left-side pump chamber, the spacers 50 in the right-side pump chamber 181 may define a semi-elliptical, spherical, box-like or any other suitably shaped depression. It should be understood, however, that the spacer elements 50 may have a fixed height, a different spatial pattern than those shown, and so on.

Also, the membrane 15 may itself have spacer elements or other features, such as ribs, bumps, tabs, grooves, channels, etc., in addition to, or in place of the spacer elements 50. Such features on the membrane 15 may help prevent sticking of the membrane 15, etc., and/or provide other features, such as helping to control how the sheet folds or otherwise deforms when moving during pumping action. For example, bumps or other features on the membrane 15 may help the sheet to deform consistently and avoid folding at the same area(s) during repeated cycles. Folding of a same area of the membrane 15 at repeated cycles may cause the membrane 15 to prematurely fail at the fold area, and thus features on the membrane 15 may help control the way in which folds occur and where.

Figure 8:
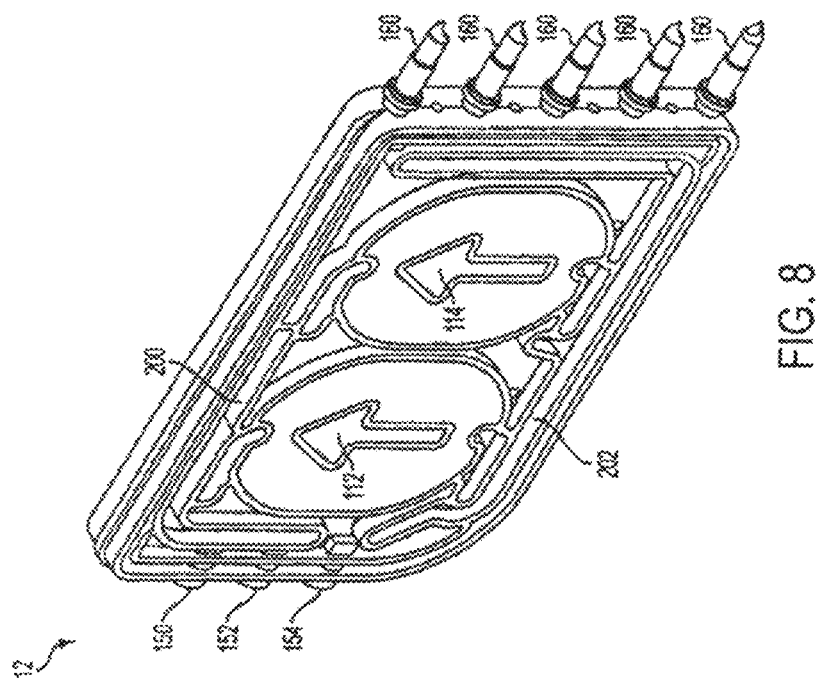
FIG. 8 is a rear perspective view of the cassette body of FIG. 3.
Figure 9:
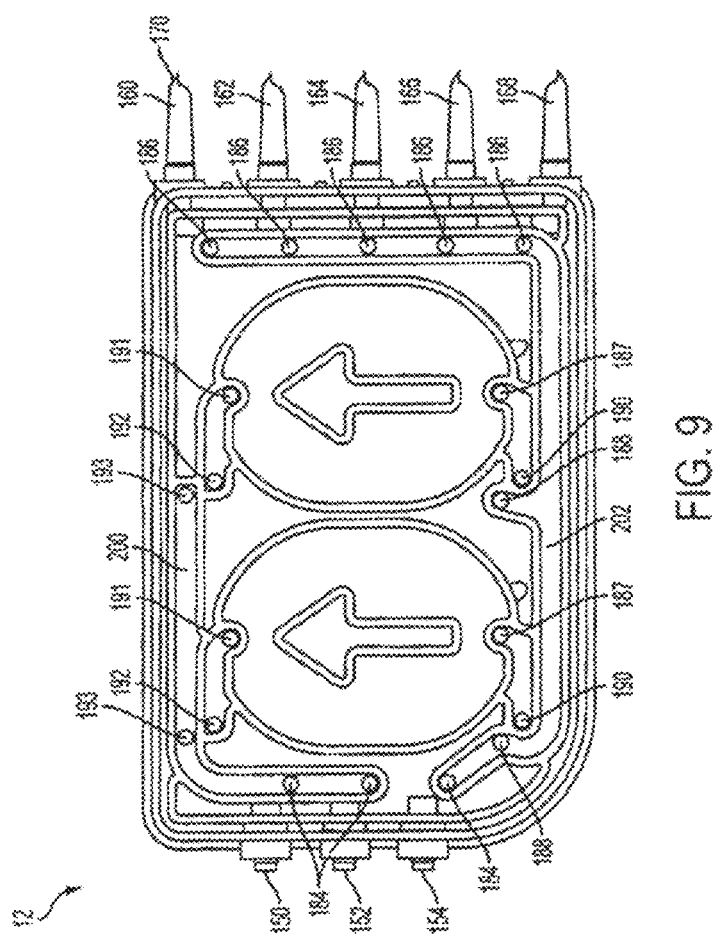
FIG. 9 is a rear view of the cassette body of FIG. 3.

In this illustrative embodiment, the base member 18 of the cassette 24 defines a plurality of controllable valve features, fluid pathways and other structures to guide the movement of fluid in the cassette 24. FIG. 6 shows a plan view of the pump chamber side of the base member 18, which is also seen in perspective view in FIG. 3. FIG. 8 shows a perspective view of a back side of the base member 18, and FIG. 9 shows a plan view of the back side of the base member 18. The tube 156 for each of the ports 150, 152 and 154 fluidly communicates with a respective valve well or chamber 183 that is formed in the base member 18. The valve wells or chambers 183 are fluidly isolated from each other by walls surrounding each valve well or chamber 183 and by sealing engagement of the membrane 15 with the walls around the wells or chambers 183. Similarly, valve wells 185 can be sealed from ports 186 by operation of the cassette membrane 15. And pump inlet or outlet valves have wells 189, 194 that can be sealed from ports 190, 192. As mentioned above, the membrane 15 may sealingly engage the walls 196 (which form the valve seats) around each valve well or chamber 183, 185, 189 and 194 (and other walls of the base member 18) by being pressed into contact with the walls, e.g., when loaded into the cycler 14. Fluid in the valve wells or chambers 183, 185, 189 and 194 may flow into or out of a respective valve port or orifice 184, 186, 190 and 192, if the membrane 15 is not pressed into sealing engagement with the valve port or orifice 184, etc. Thus, each valve port or orifice 184 defines a valve (e.g., a "volcano valve") that can be opened and closed by selectively moving a portion of the membrane 15 associated with the valve port or orifice 184. The cassette valve port or orifice seat can be defined by a raised circumferential wall 196, forming a valve seat (see, e.g., FIGS. 3, 4), so that occlusion of the port by the cassette membrane 15 and associated valve control region of gasket 148 can be achieved more reliably. But in other embodiments, a cassette valve port seat may not comprise a raised wall 196 if the cassette membrane 15 is sufficiently flexible or appropriately shaped, and the applied pressure is sufficient to seal the valve port 184 from the valve well or chamber 183.

As will be described in more detail below, the cycler 14 may selectively control the position of portions of the membrane 15 so that cassette valve ports or orifices (such as ports 184) may be opened or closed so as to control flow through the various fluid channels and other pathways in the cassette 24. Flow through the valve ports or orifices 184 leads to the back side of the base member 18. For the valve ports 184 associated with the heater bag and the drain (ports 150 and 152), the valve ports 184 lead to a common channel 200 formed at the back side of the base member 18. As with the valve wells or chambers 183, the channel 200 is isolated from other channels and pathways of the cassette 24 by the sheet 16 making sealing contact with the walls of the base member 18 that form the channel 200. For the valve port or orifice 184 associated with the patient line port 154, flow through the port 184 leads to a common channel 202 on the back side of the base member 18. Common channel 200 may also be referred to herein as an upper fluidic bus and common channel 202 may also be referred to herein as a lower fluidic bus.

Returning to FIG. 6, each of the spikes 160 (shown uncapped in FIG. 6) fluidly communicates with a respective valve well 185, which are isolated from each other by walls and sealing engagement of the membrane 15 with the walls that form the wells 185. Fluid in the valve wells 185 may flow into a respective valve port 186, if the membrane 15 is not in sealing engagement with the port 186. (Again, the position of portions of the membrane 15 over each valve port 186 can be controlled by the cycler 14 to open and close the valve ports 186.) Flow through the valve ports 186 leads to the back side of the base member 18 and into the common channel 202. Thus, in accordance with one aspect of the invention, a cassette may have a plurality of solution supply lines (or other lines that provide materials for providing dialysate) that are connected to a common manifold or channel of the cassette, and each line may have a corresponding valve to control flow from/to the line with respect to the common manifold or channel. Fluid in the channel 202 may flow into lower openings 187 of the pump chambers 181 by way of openings 188 that lead to lower pump valve wells 189 (see FIG. 6). Flow from the lower pump valve wells 189 may pass through a respective lower pump valve port 190 if a respective portion of the membrane 15 is not pressed in sealing engagement with the port 190. As can be seen in FIG. 9, the lower pump valve ports 190 lead to a channel that communicates with the lower openings 187 of the pump chambers 181. Flow out of the pump chambers 181 may pass through the upper openings 191 and into a channel that communicates with an upper valve port 192. Flow from the upper valve port 192 (if the membrane 15 is not in sealing engagement with the port 192) may pass into a respective upper valve well 194 and into an opening 193 that communicates with the common channel 200 on the back side of the base member 18.

As will be appreciated, the cassette 24 may be controlled so that the pump chambers 181 can pump fluid from and/or into any of the ports 150, 152 and 154 and/or any of the spikes 160. For example, fresh dialysate provided by one of the containers 20 that is connected by a line 30 to one of the spikes 160 may be drawn into the common channel 202 by opening the appropriate valve port 186 for the proper spike 160 (and possibly closing other valve ports 186 for other spikes). Also, the lower pump valve ports 190 may be opened and the upper pump valve ports 192 may be closed. Thereafter, the portion of the membrane 15 associated with the pump chambers 181 (i.e., pump membranes 151) may be moved (e.g., away from the base member 18 and the pump chamber inner wall) so as to lower the pressure in the pump chambers 181, thereby drawing fluid in through the selected spike 160 through the corresponding valve port 186, into the common channel 202, through the openings 188 and into the lower pump valve wells 189, through the (open) lower pump valve ports 190 and into the pump chambers 181 through the lower openings 187. The valve ports 186 are independently operable, allowing for the option to draw fluid through any one or a combination of spikes 160 and associated source containers 20, in any desired sequence, or simultaneously. (Of course, only one pump chamber 181 need be operable to draw fluid into itself. The other pump chamber may be left inoperable and closed off to flow by closing the appropriate lower pump valve port 190.)

With fluid in the pump chambers 181, the lower pump valve ports 190 may be closed, and the upper pump valve ports 192 opened. When the membrane 15 is moved toward the base member 18, the pressure in the pump chambers 181 may rise, causing fluid in the pump chambers 181 to pass through the upper openings 191, through the (open) upper pump valve ports 192 and into the upper pump valve wells 194, through the openings 193 and into the common channel 200. Fluid in the channel 200 may be routed to the heater bag port 150 and/or the drain port 152 (and into the corresponding heater bag line or drain line) by opening the appropriate valve port 184. In this way, for example, fluid in one or more of the containers 20 may be drawn into the cassette 24, and pumped out to the heater bag 22 and/or the drain.

Fluid in the heater bag 22 (e.g., after having been suitably heated on the heater tray for introduction into the patient) may be drawn into the cassette 24 by opening the valve port 184 for the heater bag port 150, closing the lower pump valve ports 190, and opening the upper pump valve ports 192. By moving the portions of the membrane 15 associated with the pump chambers 181 away from the base member 18, the pressure in the pump chambers 181 may be lowered, causing fluid flow from the heater bag 22 and into the pump chambers 181. With the pump chambers 181 filled with heated fluid from the heater bag 22, the upper pump valve ports 192 may be closed and the lower pump valve ports 190 opened. To route the heated dialysate to the patient, the valve port 184 for the patient port 154 may be opened and valve ports 186 for the spikes 160 closed. Movement of the membrane 15 in the pump chambers 181 toward the base member 18 may raise the pressure in the pump chambers 181 causing fluid to flow through the lower pump valve ports 190, through the openings 188 and into the common channel 202 to, and through, the (open) valve port 184 for the patient port 154. This operation may be repeated a suitable number of times to transfer a desired volume of heated dialysate to the patient.

When draining the patient, the valve port 184 for the patient port 154 may be opened, the upper pump valve ports 192 closed, and the lower pump valve ports 190 opened (with the spike valve ports 186 closed). The membrane 15 may be moved to draw fluid from the patient port 154 and into the pump chambers 181. Thereafter, the lower pump valve ports 190 may be closed, the upper valve ports 192 opened, and the valve port 184 for the drain port 152 opened. Fluid from the pump chambers 181 may then be pumped into the drain line for disposal or for sampling into a drain or collection container. (Alternatively, fluid may also be routed to one or more spikes 160/lines 30 for sampling or drain purposes). This operation may be repeated until sufficient dialysate is removed from the patient and pumped to the drain.

The heater bag 22 may also serve as a mixing container. Depending on the specific treatment requirements for an individual patient, dialysate or other solutions having different compositions can be connected to the cassette 24 via suitable solution lines 30 and spikes 160. Measured quantities of each solution can be added to heater bag 22 using cassette 24, and admixed according to one or more predetermined formulae stored in microprocessor memory and accessible by control system 16. Alternatively, specific treatment parameters can be entered by the user via user interface 144. The control system 16 can be programmed to compute the proper admixture requirements based on the type of dialysate or solution containers connected to spikes 160, and can then control the admixture and delivery of the prescribed mixture to the patient.

In accordance with an aspect of the invention, the pressure applied by the pumps to dialysate that is infused into the patient or removed from the patient may be controlled so that patient sensations of "tugging" or "pulling" resulting from pressure variations during drain and fill operations may be minimized. For example, when draining dialysate, the suction pressure (or vacuum/negative pressure) may be reduced near the end of the drain process, thereby minimizing patient sensation of dialysate removal. A similar approach may be used when nearing the end of a fill operation, i.e., the delivery pressure (or positive pressure) may be reduced near the end of fill. Different pressure profiles may be used for different fill and/or drain cycles in case the patient is found to be more or less sensitive to fluid movement during different cycles of the therapy. For example, a relatively higher (or lower) pressure may be used during fill and/or drain cycles when a patient is asleep, as compared to when the patient is awake. The cycler 14 may detect the patient's sleep/awake state, e.g., using an infrared motion detector and inferring sleep if patient motion is reduced, or using a detected change in blood pressure, brain waves, or other parameter that is indicative of sleep, and so on. Alternately, the cycler 14 may simply "ask" the patient— "are you asleep?" and control system operation based on the patient's response (or lack of response).

Set Loading and Operation

Figure 10:
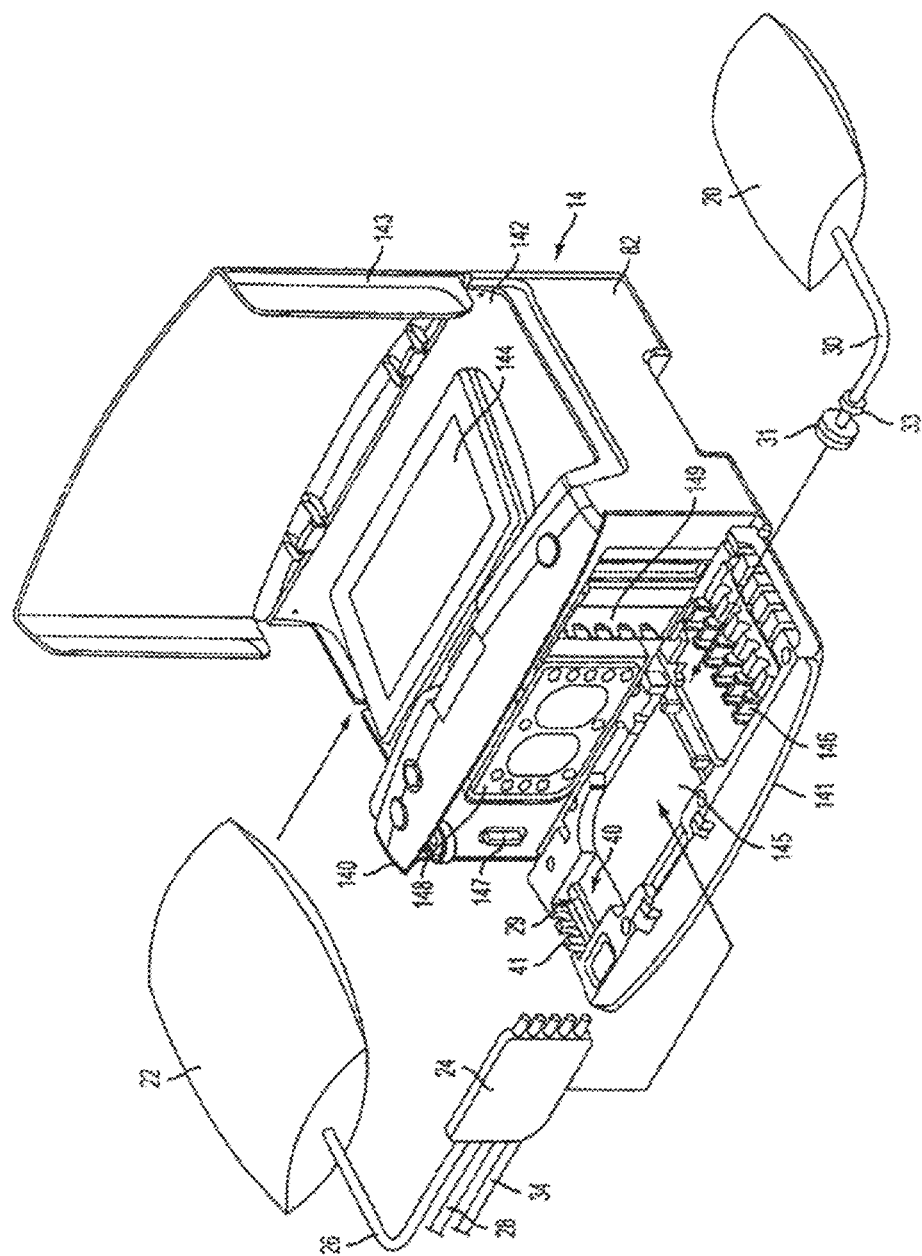
FIG. 10 is a perspective view of the APD system of FIG. 1 with the door of the cycler in an open position.

FIG. 10 shows a perspective view of the APD system 10 of FIG. 1 with the door 141 of the cycler 14 lowered into an open position, exposing a mounting location 145 for the cassette 24 and a carriage 146 for the solution lines 30. (In this embodiment, the door 141 is mounted by a hinge at a lower part of the door 141 to the cycler housing 82.) When loading the set 12, the cassette 24 is placed in the mounting location 145 with the membrane 15 and the pump chamber side of the cassette 24 facing upwardly, allowing the portions of the membrane 15 associated with the pump chambers and the valve ports to interact with a control surface or gasket 148 of the cycler 14 when the door 141 is closed. The mounting location 145 may be shaped so as to match the shape of the base member 18, thereby ensuring proper orientation of the cassette 24 in the mounting location 145. In this illustrative embodiment, the cassette 24 and mounting location 145 have a generally rectangular shape with a single larger radius corner which requires the user to place the cassette 24 in a proper orientation into the mounting location 145 or the door 141 will not close. It should be understood, however, that other shapes or orientation features for the cassette 24 and/or the mounting location 145 are possible.

In accordance with an aspect of the invention, when the cassette 24 is placed in the mounting location 145, the patient, drain and heater bag lines 34, 28 and 26 are routed through a channel 40 in the door 141 to the left as shown in FIG. 37. The channel 40, which may include guides 41 or other features, may hold the patient, drain and heater bag lines 34, 28 and 26 so that an occluder 147 may selectively close/open the lines for flow. Upon closing of door 141, occluder 147 can compress one or more of patient, drain and heater bag lines 34, 28 and 26 against occluder stop 29. Generally, the occluder 147 may allow flow through the lines 34, 28 and 26 when the cycler 14 is operating (and operating properly), yet occlude the lines when the cycler 14 is powered down (and/or not operating properly). Occlusion of the lines may be performed by pressing on the lines, or otherwise pinching the lines to close off the flow path in the lines. Preferably, the occluder 147 may selectively occlude at least the patient and drain lines 34 and 28.

When the cassette 24 is mounted and the door 141 is closed, the pump chamber side of the cassette 24 and the membrane 15 may be pressed into contact with the control surface or gasket 148, e.g., by an air bladder, spring or other suitable arrangement in the door 141 behind the mounting location 145 that squeezes the cassette 24 between the mounting location 145 and the control surface 148. This containment of the cassette 24 may press the membranes 15 and 16 into contact with walls and other features of the base member 18, thereby isolating channels and other flow paths of the cassette 24 as desired. The control surface or gasket 148 may include a flexible or elastomeric material, e.g., a sheet of silicone rubber or other material, either involving the entire gasket, or at least portions of the gasket that serve as pump or valve control regions. The gasket is positioned adjacent the membrane 15 and can selectively move portions of the membrane 15 to cause pumping action in the pump chambers 181 and opening/closing of valve ports of the cassette 24. The control gasket 148 may be associated with the various portions of the membrane 15, e.g., placed into intimate contact with each other, so that portions of the membrane 15 move in response to movement of corresponding portions of the control gasket 148. For example, the membrane 15 and control gasket 148 may be positioned close together, and a suitable vacuum (or pressure that is lower relative to ambient) may be introduced through vacuum ports suitably located in the control gasket 148 (preferably near the respective pump and valve control regions to evacuate air from between the gasket and cassette membrane specifically in the control regions) A negative pressure is maintained between the membrane 15 and the control gasket 148 so that the membrane 15 and the control gasket 148 are essentially stuck together, at least in regions of the membrane 15 that require movement to open/close valve ports and/or to cause pumping action. In another embodiment, the membrane 15 and control gasket 148 may be adhered together, or otherwise suitably associated.

In some embodiments, the surface of the control gasket 148 facing the corresponding cassette membrane overlying the pump chambers and/or valves is textured or roughened. The texturing creates a plurality of small passages horizontally or tangentially along the surface of the gasket when the gasket is pulled against the surface of the corresponding cassette membrane. This may improve evacuation of air between the gasket surface and the cassette membrane surface in the textured locations. It may also improve the accuracy of pump chamber volume determinations using pressure-volume relationships (such as, for example, ideal gas law calcualtions), by minimizing trapped pockets of air between the gasket and the membrane. It may also improve the detection of any liquid that may leak into the potential space between the gasket and the cassette membrane. In an embodiment, the texturing may be accomplished by masking the portions of the gasket mold that do not form the portions of the gasket corresponding to the pump membrane and valve membrane locations. A chemical engraving process such as the Mold-Tech® texturing and chemical engraving process may then be applied to the unmasked portions of the gasket mold. Texturing may also be accomplished by any of a number of other processes, such as, for example, sand blasting, laser etching, or utilizing a mold manufacturing process using electrical discharge machining.

Figure 11:
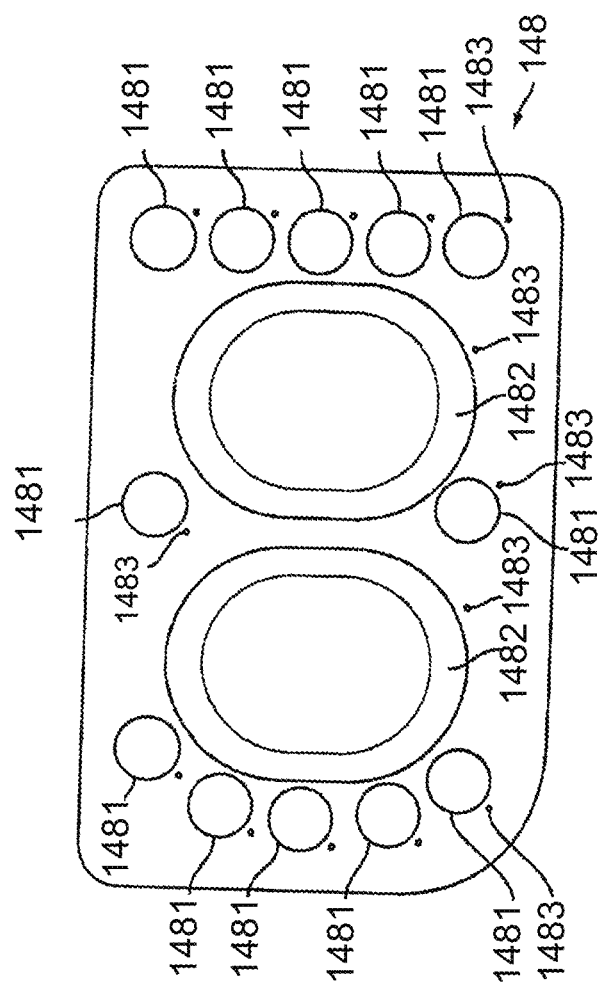
FIG. 11 is a front view of a control surface of the cycler for interaction with a cassette in the FIG. 10 embodiment.

FIG. 11 shows a plan view of the control gasket 148 of the cycler 14 that interacts with the pump chamber side of the cassette 24 (e.g., shown in FIG. 6) to cause fluid pumping and flow path control in the cassette 24. When at rest, the control gasket 148, which may be described as a type of gasket, and comprise a sheet of silicone rubber, may be generally flat. Valve control regions 1481 may (or may not) be defined in the control gasket 148, e.g., by a scoring, groove, rib or other feature in or on the sheet surface, and be arranged to be movable or elastically deformable/stretchable in a direction generally transverse to the plane of the sheet. By moving inwardly/outwardly, the valve control regions 1481 can move associated portions of the membrane 15 on the cassette 24 so as to open and close respective valve ports 184, 186, 190 and 192 of the cassette 24, and thus control flow in the cassette 24. Two larger regions, pump control regions 1482, may likewise be movable so as to move associated shaped portions 151 of the membrane 15 that cooperate with the pump chambers 181. Like the shaped portions 151 of the membrane 15, the pump control regions 1482 may be shaped in a way to correspond to the shape of the pump chambers 181 when the control regions 1482 are extended into the pump chambers 181. In this way, the portion of the control sheet or gasket 148 at the pump control regions 1482 need not necessarily be stretched or otherwise resiliently deformed during pumping operation.

Typically, the control gasket 148 is constructed from a single material, so that it can be readily formed from a mold. The flat portions of the gasket help to compress and seal the cassette membrane 15 against the border or perimeter walls of the cassette, sealing liquid flowpaths within the cassette when it is pressed against the control surface/gasket and its supporting mating block 170. Similarly, as the cassette is pressed against the control surface/gasket, the fluid control ports 173A, 173C can be sealed from each other, so that the control chambers 171A, and 2746 can be individually and independently pressurized with positive or negative pneumatic pressure.

Alternatively, the movable portions of the control gasket 148, such as the pump control regions 1482 and valve control regions 1481 may comprise a material with different thickness, elasticity and/or durometer values than the flat portions of the gasket. The different materials can be fused together in a molding or overmolding operation, or can be solvent-bonded together, for example, using an adhesive. The pump control regions 1482 and valve control regions 1482 of the gasket 148 preferably are constructed of elastomeric material of a thickness and elasticity to permit their adequate movement in response to positive or negative actuation pressure, in order to move the associated pump and valve portions of the cassette membrane 15 a desired amount. The valve control regions 1482 in particular benefit from a relatively stiff control gasket body adjacent the periphery of the valve control regions, so that it can contribute to supporting the body of the valve control region against the valve ports of the cassette when in a valve closing position.

Each of the regions 1481 and 1482 may have an associated vacuum or evacuation port 1483 that may be used to remove all or substantially all of any air or other fluid that may be present between the membrane 15 of cassette 24, and the control gasket 148 of cycler 14, e.g., after the cassette 24 is loaded into the cycler 14 and the door 141 closed. This may help ensure close contact of the membrane 15 with the control regions 1481 and 1482, and help control the delivery of desired volumes with pump operation and/or the open/closed state of the various valve ports. Note that the vacuum ports 1482 are formed in locations where the control gasket 148 will not be pressed into contact with a wall or other relatively rigid feature of the cassette 24. For example, in accordance with one aspect of the invention, one or both of the pump chambers of the cassette 24 may include a vacuum vent clearance region formed adjacent the pump chamber. In this illustrative embodiment as shown in FIGS. 3 and 6, the base member 18 may include vacuum vent port clearance or extension features 182 (e.g., recessed areas that are fluidly connected to the pump chambers) adjacent and outside the oval-shaped depressions forming the pump chambers 181 to allow the vacuum vent port 1483 for the pump control region 1482 to remove any air or fluid from between membrane 15 and control gasket 148 (e.g., due to rupture of the membrane 15) without obstruction. The extension feature may also be located within the perimeter of pump chamber 181. However, locating vent port feature 182 outside the perimeter of pump chamber 181 may preserve more of the pumping chamber volume for pumping liquids, e.g., allows for the full footprint of pump chamber 181 to be used for pumping dialysate. Preferably, extension feature 182 is located in a vertically lower position in relation to pump chamber 181, so that any liquid that leaks between membrane 15 and control gasket 148 is drawn out through vacuum port 1483 at the earliest opportunity. Similarly, vacuum ports 1483 associated with valves 1481 are preferably located in a vertically inferior position with respect to valves 1481.

In some embodiments, the surface of the control gasket 148 or gasket facing the corresponding cassette membrane 148 overlying the pump chambers and/or valves is textured or roughened. The texturing creates a plurality of small passages horizontally or tangentially along the surface of the gasket when the gasket is pulled against the surface of the corresponding cassette membrane. This may improve evacuation of air between the gasket surface and the cassette membrane surface in the textured locations. It may also improve the accuracy of pump chamber volume determinations using pressure-volume relationships (such as, for example, in the FMS procedures described elsewhere), by minimizing trapped pockets of air between the gasket and the membrane. It may also improve the detection of any liquid that may leak into the potential space between the gasket and the cassette membrane. In an embodiment, the texturing may be accomplished by masking the portions of the gasket mold that do not form the portions of the gasket corresponding to the pump membrane and valve membrane locations. A chemical engraving process such as the Mold-Tech® texturing and chemical engraving process may then be applied to the unmasked portions of the gasket mold. Texturing may also be accomplished by any of a number of other processes, such as, for example, sand blasting, laser etching, or utilizing a mold manufacturing process using electrical discharge machining.

Figure 12:
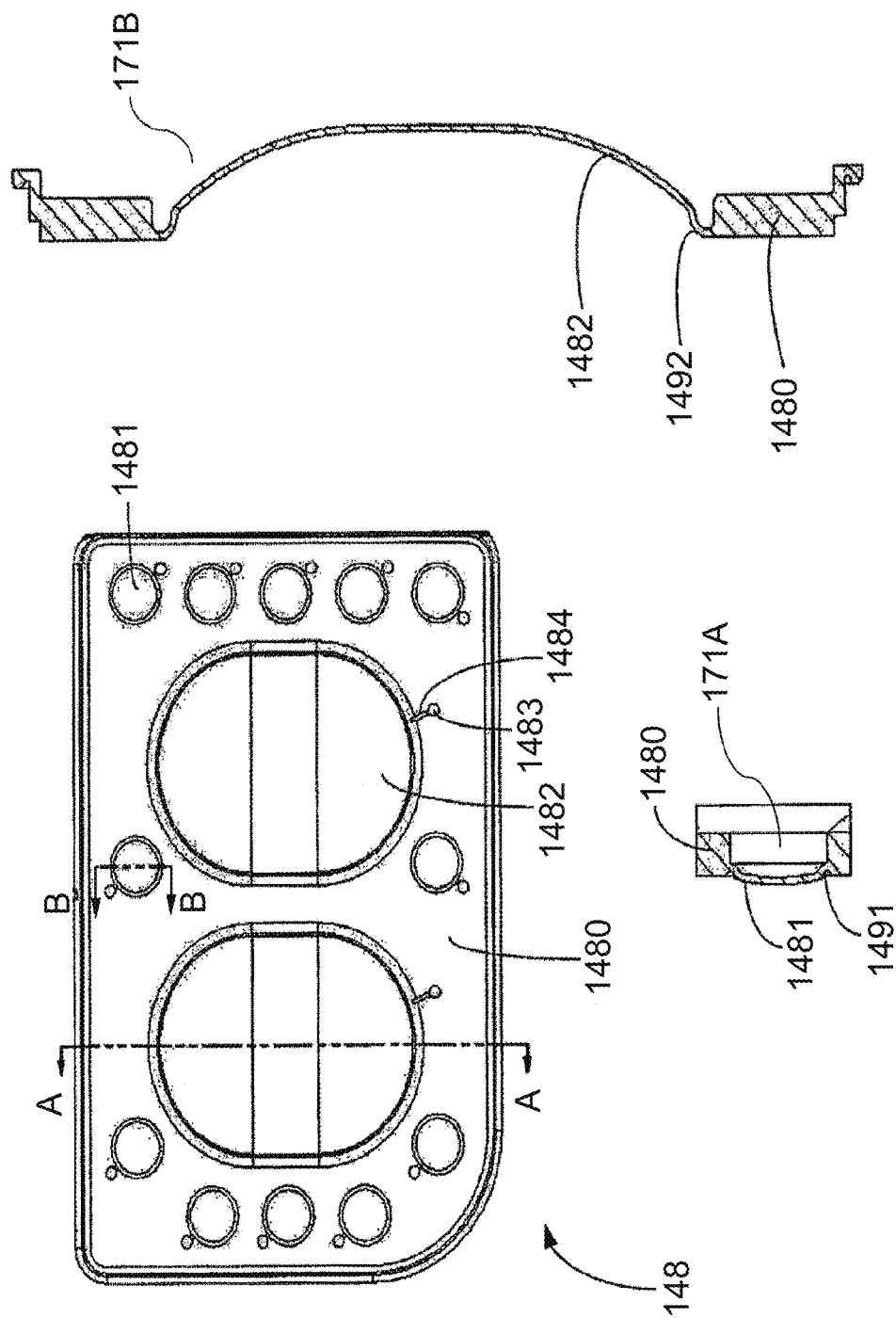
FIG. 12 is a front view and selected cross-sectional views of an embodiment of a control surface of the cycler.

FIG. 12 shows that control gasket 148 may optionally be constructed or molded to have a rounded transition between the base element 1480 of control gasket 148 and the actuation portions of its valve and pump control regions 1481, 1482. These junctions or channels 1491 and 1492 may be molded with a small radius to transition from base element 1480 to valve control region 1481 and pump control region 1482, respectively. A rounded or smooth transition helps to prevent premature fatigue and fracture of the material comprising control gasket 148, and may improve its longevity. In an optional embodiment, radial channels 1484 lead from vacuum ports 1483 to the pump control regions 1482 and valve control regions 1481, and may need to be lengthened somewhat to accommodate the transition feature. Junctions or channels 1491 and 1492 function as vacuum channels, transmitting and distributing the vacuum being applied through the pressure delivery block to the potential spaces between the pump control regions 1482 and valve control regions 1481 and the corresponding pump and valve portions of the cassette membrane 15. (Note that these vacuum channels optionally may also be used to transmit positive pressure to the potential spaces between gasket control regions and the corresponding cassette membrane regions in order to aid in separating the cassette from the pressure delivery block when desired). The vacuum channels 1491 and 1492 run along the periphery or perimeter of the pump or valve control regions of the gasket 148, and allow a more uniform application of vacuum to these surfaces.

Although not necessarily required, these vacuum channels 1491 and 1492 may optionally and conveniently extend along the circumference of the periphery of the pump and valve control regions of gasket 148, as shown, for example, in FIG. 12. For either a pump control region 1482 or a valve control region 1481 of the gasket 148, the channel 1484 corresponding to a particular control region is radially oriented to connect a nearby gasket vacuum port 1483 to channel 1491 or 1492 that extends along a perimeter of its associated gasket control region. Although the vacuum channel 1491, 1492 need not completely encircle its associated pump or valve control region to ensure uniform application of vacuum to the entire surface of the control region, a circumferential arrangement also serves the purpose of providing a flexible mechanical transition between the base element 1480 of gasket 148 and the body of the gasket control region 1481 or 1482.

The control regions 1481 and 1482 may be moved or elastically deformed by controlling a pneumatic pressure and/or volume on a side of the control gasket 148 opposite the cassette 24, e.g., on a back side of the elastomeric sheet that forms the control gasket 148. For example, as shown in FIGS. 15A-23C, the control gasket 148 may be backed by a mating or pressure delivery block 170 that includes control chambers or depressions 171A located in association with each control region 1481, and control chambers or depressions 171B, located in association with each control region 1482, and that are isolated from each other (or at least can be controlled independently of each other if desired). The control chambers or depressions 171A may define a volume. The surface of mating or pressure delivery block 170 forms a mating interface with cassette 24 when cassette 24 is pressed into operative association with control gasket 148 backed by mating block 170 (see, e.g., FIGS. 13, 14). The control chambers or depressions of mating block 170 are thus coupled to complementary valve or pumping chambers of cassette 24, sandwiching the control regions 1481 and 1482 of control gasket 148 between mating block 170 and the associated regions of cassette membrane 15 (such as shaped portion 151) adjacent to cassette 24. Positively or negatively pressurized air or other control fluid may be moved into or out of the control chambers or depressions 171A, 171B of mating block 170 for the regions 1481, 1482, thereby moving the control regions 1481, 1482 as desired to open/close valve ports of the cassette 24 and/or effect pumping action at the pump chambers 181. In one illustrative embodiment shown in FIGS. 15A-C, the control chambers 171A may be arranged as cylindrically-shaped regions or recesses backing each of the valve control regions 1481 of gasket 148. In one configuration of the valve control region 1481 of the gasket 148, the surface of the control region is slightly elevated above the overall surface of the gasket, biasing the elastically deformable control region toward the corresponding valve seat 184 of the cassette. Thus, positive pneumatic pressure applied against the valve control region is more likely to reliably seal the cassette membrane 15 against the valve seat 184. On the other hand, at least a portion of the negative pressure applied to the valve control region to lift the adjacent cassette membrane 15 off the valve seat must be expended to overcome the outwardly biased valve control region of the control gasket 148. It is also apparent that when the gasket is placed against the underlying mating block 170, a space 1478 under the dome of the control region 1481 combines with the control chamber 171A to become the total control volume that is pressurized positively or negatively to move the control region 1481 toward or away from the valve seat. The amount of total control volume that needs to be pressurized will vary based on the shape and configuration of the valve control region of the gasket (e.g., convex vs. concave toward the cassette).

Figure 13:
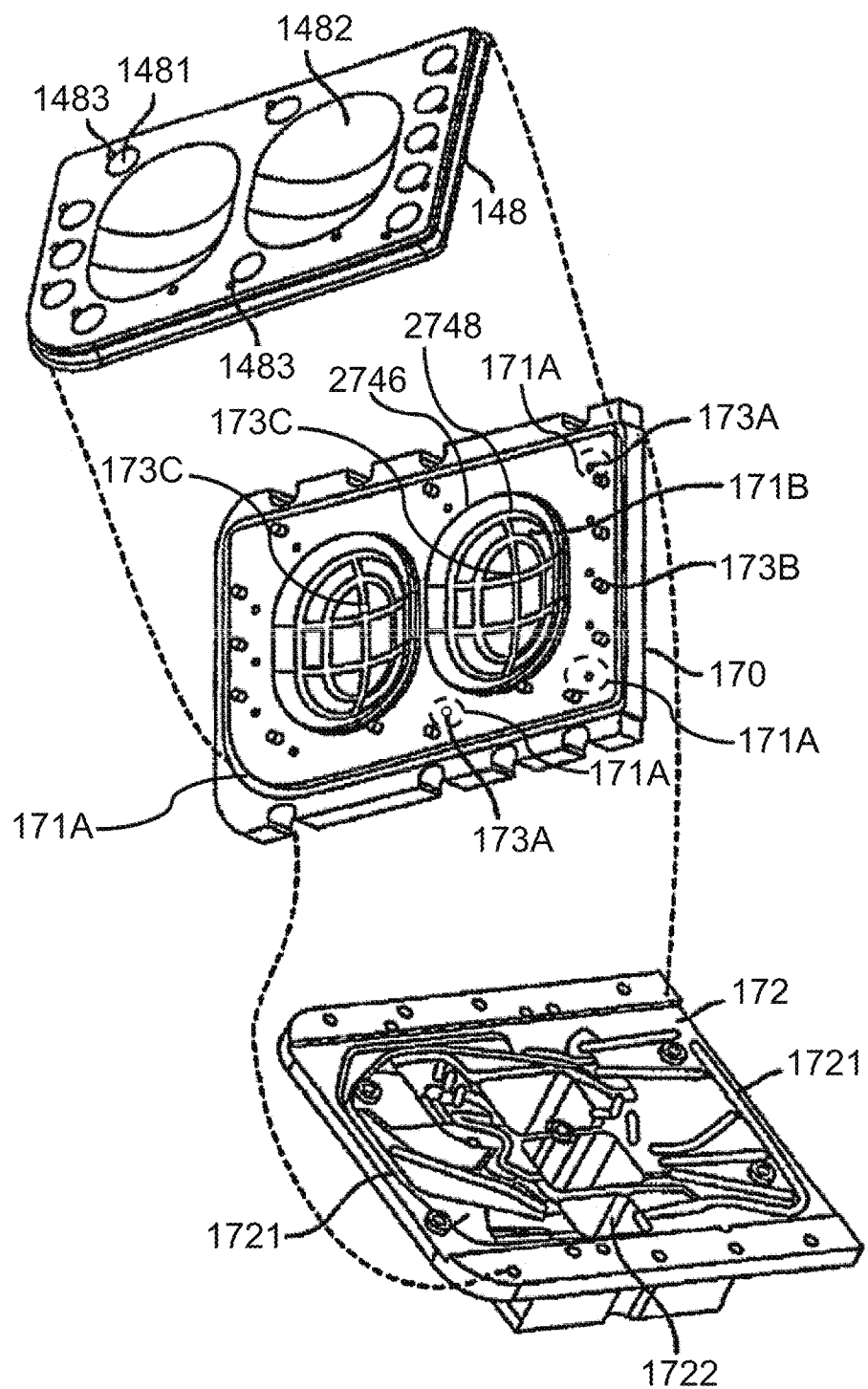
FIG. 13 is an exploded view of an assembly for the interface surface of FIG. 90, with the mating pressure delivery block and pressure distribution module.
Figure 14:
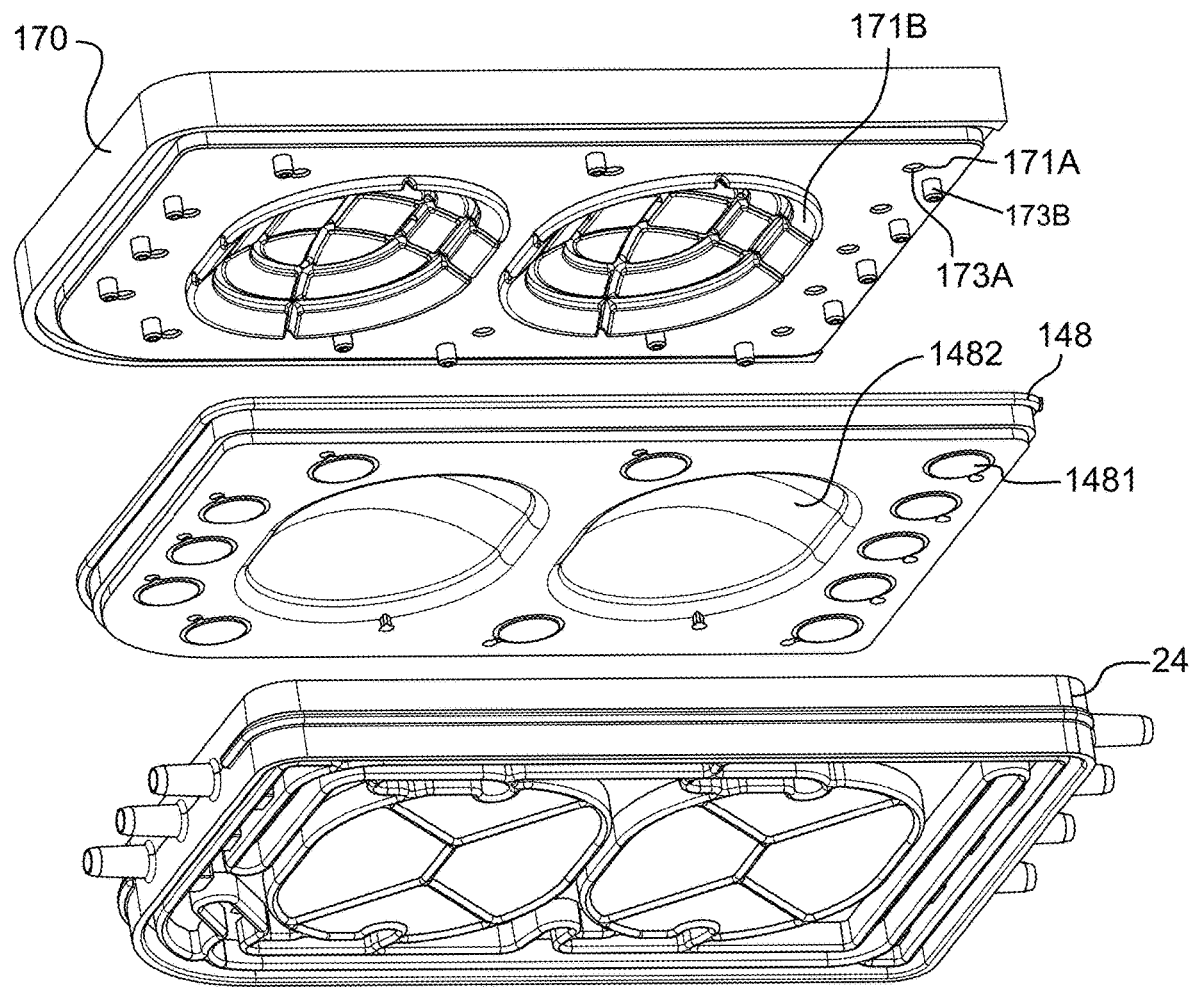
FIG. 14 shows how the control gasket is interposed between the pressure delivery block of the base unit and the pump cassette.

The control chambers or depressions 171B may comprise ellipsoid, ovoid or hemi-spheroid voids or depressions backing the pump control regions 1482. Fluid control ports 173A may be provided for each control chamber 171A so that the cycler 14 can control the volume of fluid and/or the pressure of fluid in each of the valve control chambers 1481. Fluid control ports 173C may be provided for each control chamber 171B so that the cycler 14 can control the volume of fluid and/or the pressure of fluid in each of the volume control chambers 1482. For example, as shown in FIG. 13, the mating block 170 may be mated with a manifold 172 that includes various ports, channels, openings, voids and/or other features that communicate with the control chambers 171A, B and allow suitable pneumatic pressure/vacuum to be applied to the control chambers 171A, B. Although not shown, control of the pneumatic pressure/vacuum may be performed in any suitable way, such as through the use of controllable valves, pumps, pressure sensors, accumulators, and so on. Of course, it should be understood that the control regions 1481, 1482 may be moved in other ways, such as by gravity-based systems, hydraulic systems, and/or mechanical systems (such as by linear motors, etc.), or by a combination of systems including pneumatic, hydraulic, gravity-based and mechanical systems.

Gasket Vacuum Channels

Figure 15A:
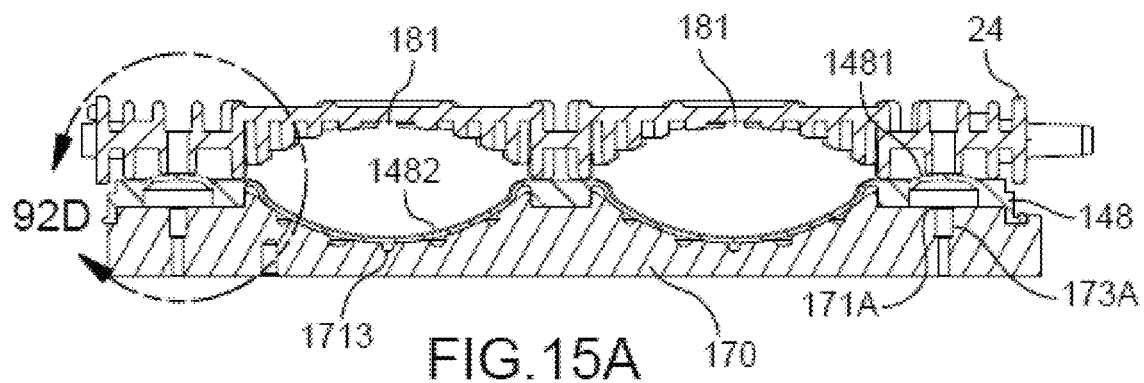
FIGS. 15A-C show cross-sectional views of the interaction between the control gasket and a valve seat of the cassette, with views of the cassette membrane absent for clarity.
Figure 15B:
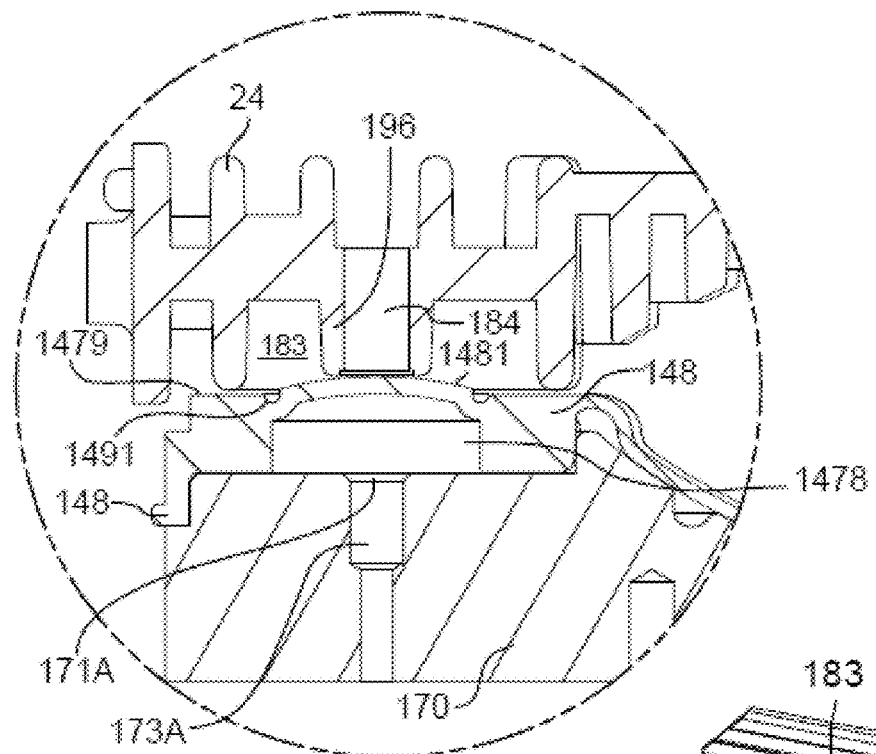
Figure 15C:
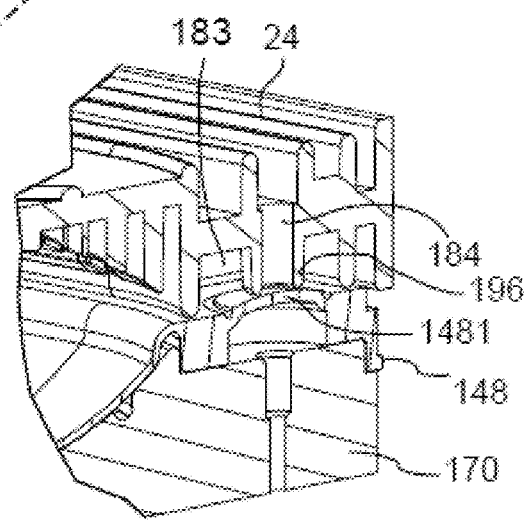

In order to function optimally, the perimeter vacuum channels 1491 or 1492 should remain patent throughout the range of motion of the gasket pump control 1482 or valve control 1481 regions during operation of the cassette (i.e. during application of positive or negative pressure through the valve control ports 173A or pump control ports 173C). That way, a continuous negative pressure can be transmitted to the potential space between the cassette membrane and gasket control region, and movement of the adjacent cassette membrane 15 can more closely follow the movement of the pump and valve control regions of the gasket. (Depending on the amount of negative pressure applied through the vacuum port and channels, an inter-membrane space may nevertheless develop at the point when maximal negative pressure is being applied to the valve control region to open a valve, as shown in FIGS. 16 and 17). To ensure a patent vacuum channel 1491, previous versions of the gasket 148 were constructed to have both walls of the perimeter channel sufficiently rigid not to flex or collapse away when negative pressure is applied to the valve control region 1481 of the gasket 148. Previous perimeter channels were therefore constructed with this rigidity constraint. An example of prior perimeter vacuum channels is shown in FIGS. 15A-C. In this example, vacuum channel 1491 has a semi-circular cross-sectional profile concave to an opposing cassette or cassette membrane (see FIG. 15B). In this case, the gasket valve control surface 1481 has a slightly convex shape toward the cassette or cassette membrane. This configuration favors the effective closure of the associated cassette valve, because the gasket valve control region is biased toward closure and the vacuum channel is defined by supporting walls that exhibit minimal flexing away from the cassette valve during delivery of negative pressure to the valve control port 173A.

Figure 16A:
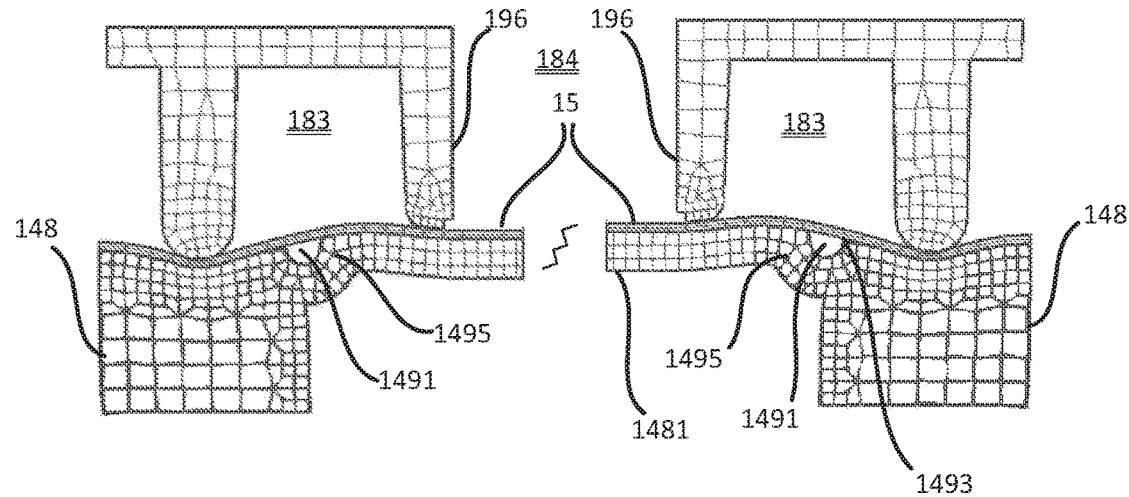
FIGS. 16A-B show cross-sectional views of the gasket perimeter vacuum channel of FIGS. 15A-C and cassette membrane in a valve closed and valve open position.
Figure 16B:
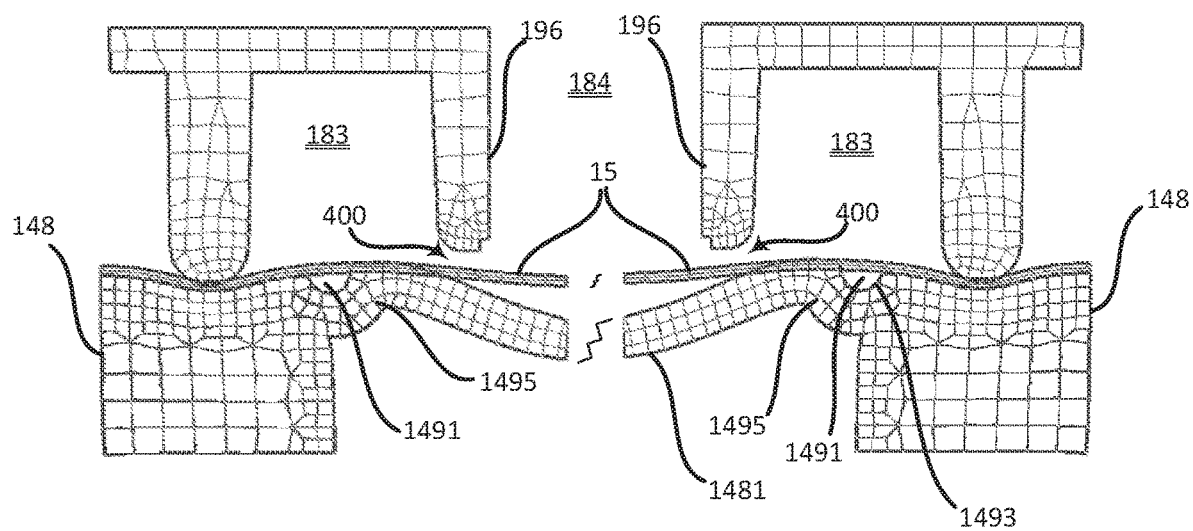

The degree of valve opening in the prior version of the gasket valve control region is shown in FIGS. 16A-B. FIG. 16A shows an example of the position of the gasket valve control region 1481 and the associated cassette membrane 15 against the wall or seat 196 of cassette valve port 184. Depending on the type of valve control region configuration, this may correspond to a closed valve position under both positive pressure and under ambient (eg., atmospheric) pressure conditions, indicating that the gasket valve control region is biased against the cassette port 184. However, the configuration under negative pressure may result in a sub-optimal valve opening area 400 as shown in FIG. 16B. This may result is fluid flow rates through the cassette valve that are sub-optimal, and may also generate membrane vibrations leading to unwanted noise.

Figure 17A:
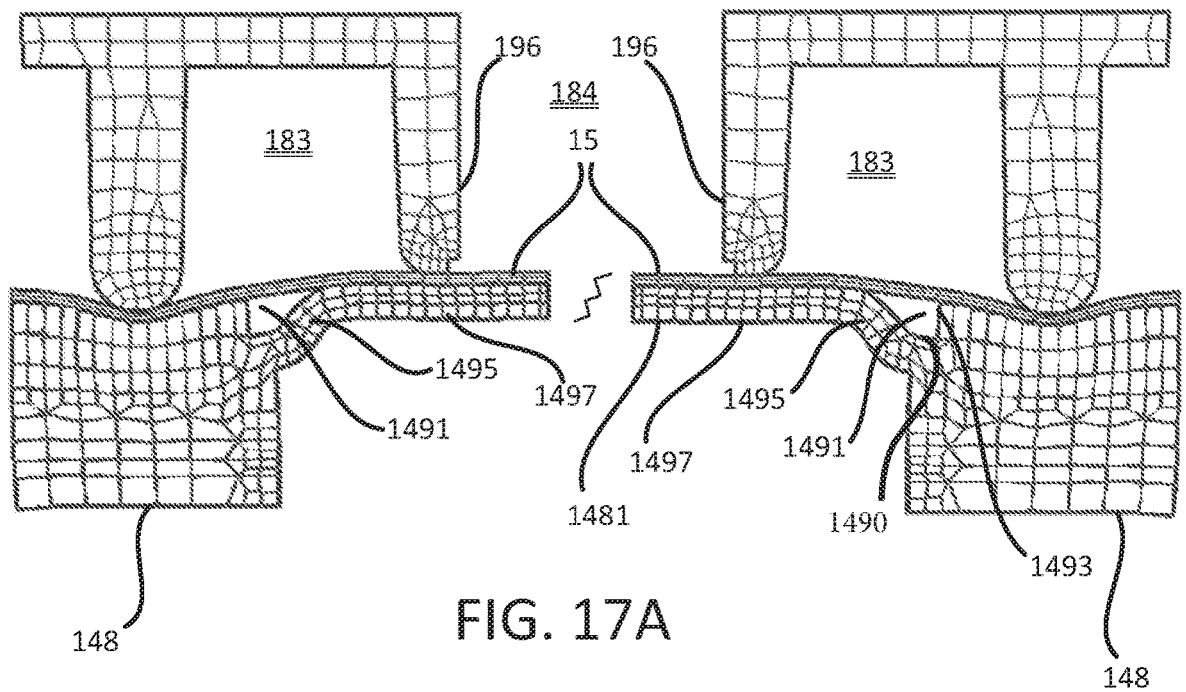
FIGS. 17A-B show cross-sectional views of an alternate gasket perimeter vacuum channel arrangement in a valve closed and valve open position.
Figure 17B:
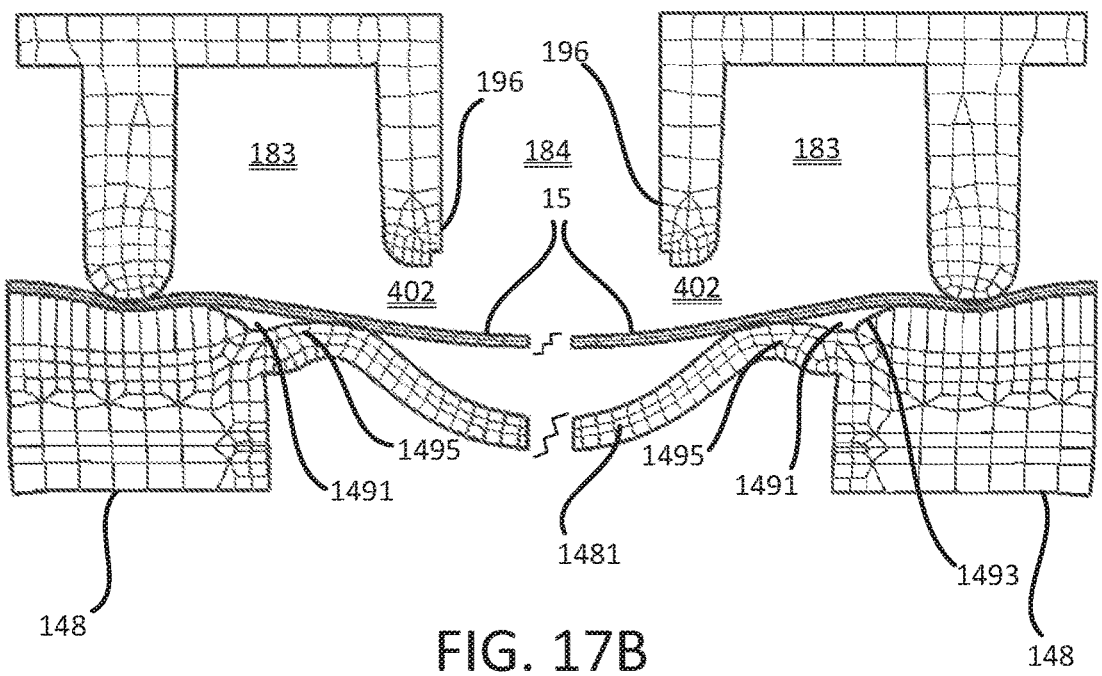

A new configuration of the gasket valve control region 1481 has been developed to reach a more useful compromise between the need to maintain an open vacuum channel 1491, to achieve reliable closure of the cassette valve, and to achieve a greater opening area of the cassette valve when the gasket valve control region is placed under negative pressure. This is shown in FIGS. 17A-B. In this case, an outer wall 1493 of the vacuum channel, contiguous with or comprising the body of the gasket 148 outside of the valve control region 1481, is designed to remain relatively stiff, so that it does not collapse or flex to the point of obliterating the vacuum channel 1491. Also defining the vacuum channel 1491 is a floor 1490, and an inner wall 1495 contiguous with a contact portion 1497 of the gasket valve control region 1481. The contact portion 1497 comprises that portion of the gasket valve control region 1481 that is adjacent the portion of the cassette membrane 15 that contacts the cassette valve port wall or seat 196 to seal the port from the valve well or chamber 183. In this embodiment, the inner vacuum channel wall 1495 is designed, constructed or molded to have greater flexibility than the outer wall 1493, so that it is able to flex or partially collapse away from the cassette when the gasket valve control region 1481 is placed under negative pressure to open the cassette valve. The patency of the vacuum channel 1491 is preserved to an extent sufficient to maintain continuous vacuum pressure through all phases of the operation of the cassette valve. An example of this property is shown in FIG. 17B. The valve opening area 402 is greater than the prior version of the gasket 148 shown in FIGS. 16A-B, which improves fluid flow rates through the cassette valve and reduces flow-related noise. In one embodiment, the elastomeric property of the inner wall 1495 is different from that of the outer wall 1493. Preferably, for manufacturing simplicity, the difference in the elasticity or flexibility of the inner wall 1495 is achieved by altering its radius of curvature, its thickness, or by changing its convexity/concavity profile, or through a combination of these. As shown in FIG. 17A, the inner vacuum channel wall 1495 is also optionally configured to bias the gasket valve control region 1481 against the port wall or seat 196 of the cassette valve, so that an effective seal is formed under positive pressure, and at least a limited seal is formed under ambient pressure. This allows a valve seal to be maintained even if there is a small positive pressure difference between the cassette valve well 183 and the port 173A of the pressure delivery block behind the gasket 148. This configuration of the gasket valve control region satisfies conflicting constraints imposed on the functioning of the cassette valve: to ensure continuous patency of the vacuum channel 1491, to ensure an adequate cassette valve opening area 402 under negative pressure, and to preserve adequate closure of the cassette valve under positive pressure (and optionally limited closure properties under ambient pressure conditions).

Variations in Valve Control Regions of the Control Gasket

In some cases, liquid flow through an open valve of the cassette may be impeded if the valve control surface does not pull the adjacent cassette membrane sufficiently far away from the valve seat (which in an embodiment, comprises a raised circumferential wall around the valve port or orifice). This is more likely to be an issue when a pump chamber is in a filling mode, applying negative pressure to one or more liquid flowpaths that include one of the cassette valves. In this circumstance, negative pressure transmitted to the liquid passing through the valve orifice may oppose the negative pneumatic pressure applied by the valve control surface of the gasket to keep the cassette membrane an adequate distance from the valve seat 184. The flow rate of liquid passing through the valve may be adversely affected, and opposing forces pulling at the membrane-gasket unit could lead to undesirable vibrations of the cassette membrane and/or gasket valve control region, generating noise during liquid flow through the valve orifice. For example, a high liquid flow rate through the valve may further reduce the pressure at the valve through a venturi effect, providing additional force opposing the opening force being applied through the valve control region of the control gasket. This could in theory set up an oscillation of the valve membrane due to variations in the opposing forces, leading to undesirable vibratory noise and an overall reduced flow rate of liquid through the valve.

Therefore in some cases, it may be desirable to alter certain properties of the gasket valve control region to limit this effect. Some of the variables suitable for alteration may include the shape, convexity, elasticity, and thickness of the gasket at the valve control region. Similar changes can be considered for the cassette membrane adjacent the cassette valves, but may be more difficult to implement due to other constraints placed on the cassette membrane (such as, for example, the requirements for the membrane to operate properly, predictably and reliably in the region of the pump chambers). There may also be constraints on the choice of composition of the cassette membrane due to the fact that it must contact and propel fluids that are infused into a patient. The cassette membrane may not therefore have the same elasticity as that of the adjacent gasket control region.

In an example, a system controller can be programmed to limit the filling pressure delivered to a pump chamber, so that any negative pressure transmitted to a valve orifice on the cassette connected to the pump chamber is lower than the negative pressure delivered to the adjacent gasket valve control region. The difference in negative pressures at the valve control region must be sufficient to ensure that the valve orifice is open to fluid flow. For example, if the negative pressure source for the system is approximately −40 kPa, this pressure can be delivered to the valve control region of the control gasket, and it or a lower negative pressure also can be delivered to the potential space between the control gasket and cassette membrane to encourage in-tandem motion of the gasket valve control region and its adjacent cassette membrane. However, the negative pressure delivered to a connected pump control region can be regulated to a lower negative pressure, such as, for example, −25 kPa, so that the associated negative pressure transmitted to the liquid flowing through the valve cannot overcome the valve-opening pressure of the gasket valve control region. However, if the gasket valve control region does not pull the cassette membrane sufficiently far enough from the valve orifice, then a resulting high liquid flow through the valve orifice could further reduce the pressure at the valve orifice, causing the cassette membrane and/or valve control region of the gasket to vibrate toward and away from the valve orifice as liquid flow and pressure begins to vary. In some circumstances, this could reduce the overall liquid flow rate through the valve, and potentially create undesirable vibration noise.

Alternate configurations of the gasket valve control region may ameliorate this problem. But any change in the gasket valve control region should be balanced against the ability of the system to reliably seal the cassette membrane against the cassette valve seat when positive pressure is delivered to the valve control region of the gasket.

FIGS. 15A-C show how a valve control region 1481 of a previous or typical gasket or control surface 148 has been arranged. The elastomeric or elastic valve control region 1481 is biased in a valve closing (or valve seat occluding) position, with an external dome-shaped surface extending above the overall plane 1479 of the gasket 148 (i.e. the plane formed by the non-valve or pump control regions of the control gasket 148). At least some of the applied negative pressure at port 173A must be expended to overcome this bias to invert the valve control region 1481, resulting in less force being available to pull the adjacent cassette membrane away from the valve seat 196. FIGS. 18A-23C show examples of valve control regions 1481A-F of the control gasket 148 in which the shape or configuration of the gasket valve control region has been altered to affect the dynamics of opening and closing the valve under any given positive or negative pneumatic pressure. The valve control regions are shown in resting or unstressed positions. In these cases, the valve control regions 1481 do not rise above the plane 1479 of the gasket 148 (i.e. the plane formed by non-control regions of the gasket). This is in contrast to the valve control region shown in FIGS. 15A-C. Any inherent elastic bias in the valve control regions will be less likely to apply a closing pressure against the adjacent cassette membrane and thus the valve seat. Less force will be needed to pull the gasket/ membrane combination away from the valve seat, allowing for increased space between the cassette membrane and the valve seat and thus increased flow of liquid through the valve. At least a portion of the valve control region at rest does not apply pressure to the cassette membrane and thus does not apply pressure against the valve seat.

In the valve control region configurations shown in FIGS. 18A-18C and 20A-20C, the inverted shape of the control regions 1481A, 1481C allows all of the applied negative pressure to be directed to pulling the gasket/cassette membrane combination away from the valve seat 196. However, less closing pressure for the cassette membrane against the valve seat 196 will be available for any given application of positive pneumatic pressure through port 173A.

Figure 19A:
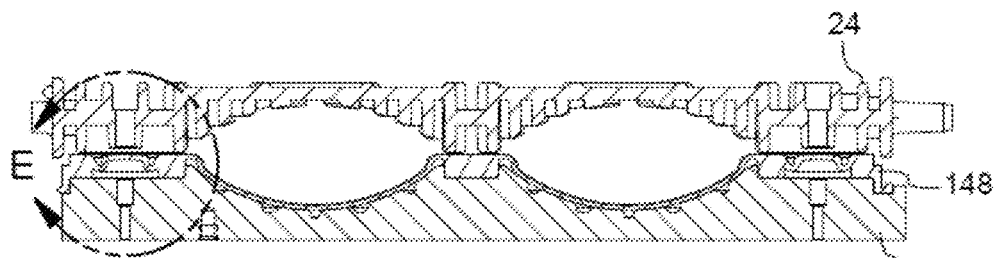
FIGS. 19A-C show cross-sectional views of a cassette valve seat and gasket valve control region, the valve control region being biased toward the valve seat but not raised above the plane of the surface of the control gasket.
Figure 19B:
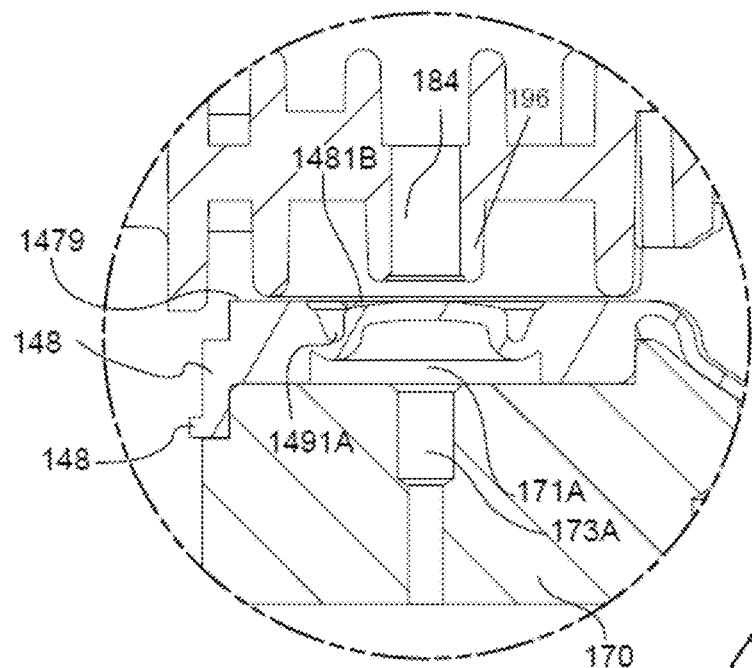
Figure 19C:
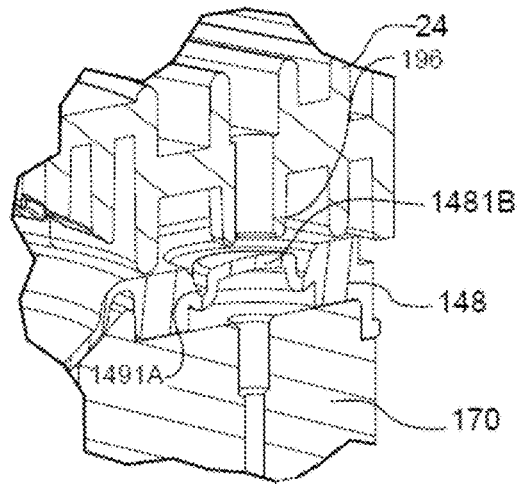

The valve control region 1481B configuration shown in FIGS. 19A-C is biased toward the cassette membrane and valve seat 196, which must be overcome before the cassette membrane can be pulled away from the valve seat 196. However, the depth of the vacuum channel 1491A at the junction between the valve control region 1481B and the main gasket 148 is increased (forming essentially a circumferential pleat around the valve control region), increasing the flexibility of the region to move, which allows the valve control region 1481B to be inverted with less applied negative pressure. This in turn allows a greater degree of valve opening for any given negative pressure applied via port 173A.

Figure 18A:
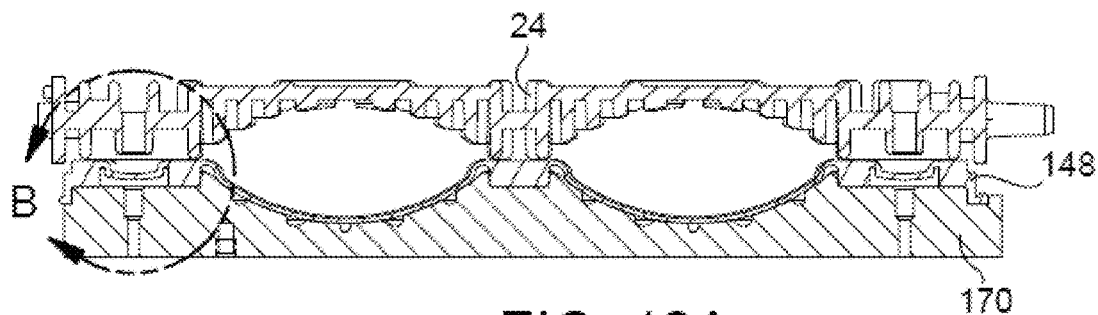
FIGS. 18A-C show cross-sectional views of a cassette valve seat and gasket valve control region, the valve control region biased in an inverted position below the surface of the control gasket.
Figure 18B:
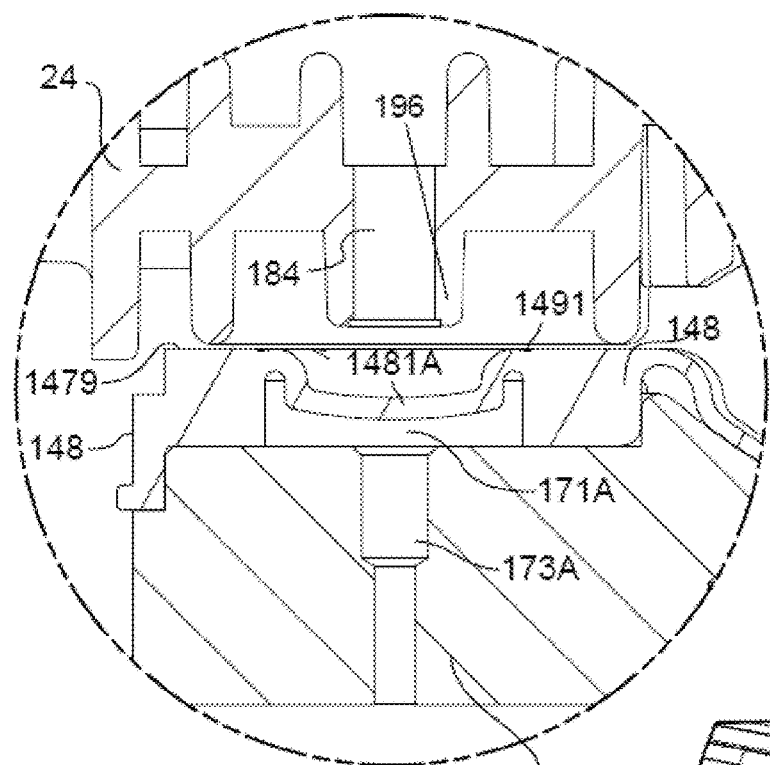
Figure 18C:
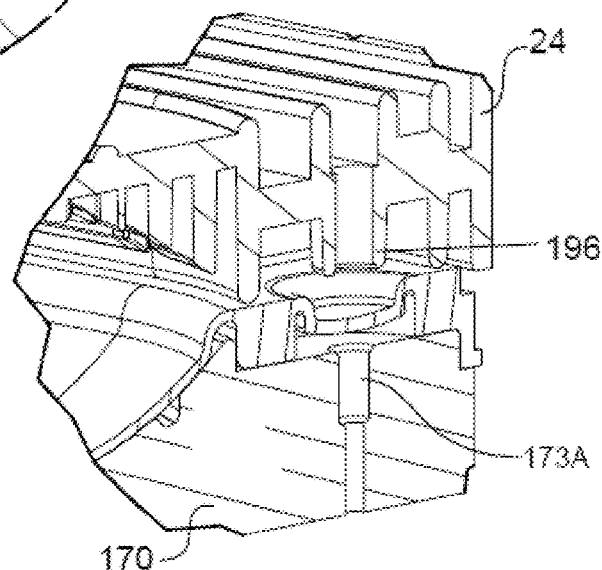

A similar but inverted radius of curvature is incorporated in the inverted valve control region 1481A of FIGS. 18A-18C. This in turn allows more of an applied positive force through port 173A to be expended in pressing the cassette membrane against the valve seat 196 when the valve needs to be closed. But in this case, the vacuum channel may be compromised unless accommodations are made for it in molding the gasket 148.

Figure 20A:
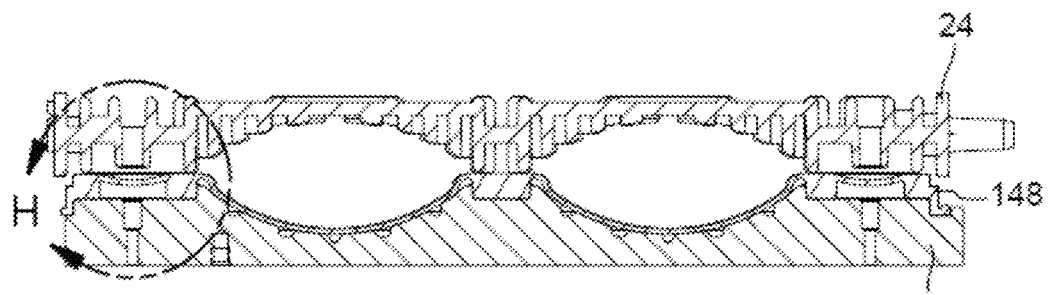
FIGS. 20A-C show cross-sectional views of a cassette valve seat and gasket valve control region, the valve control region biased in an inverted position below the surface of the control gasket.
Figure 20B:
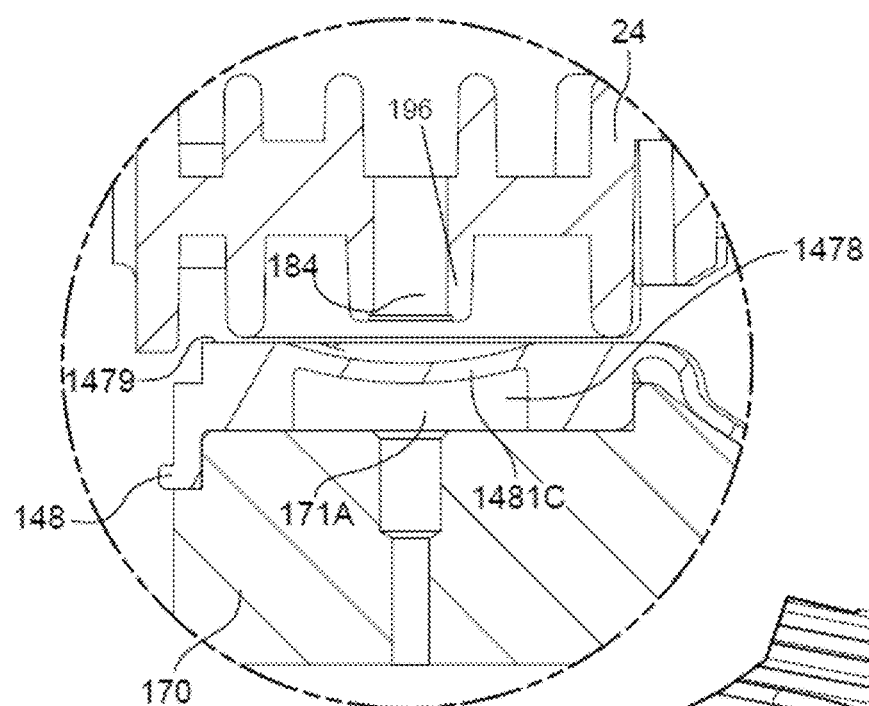
Figure 20C:
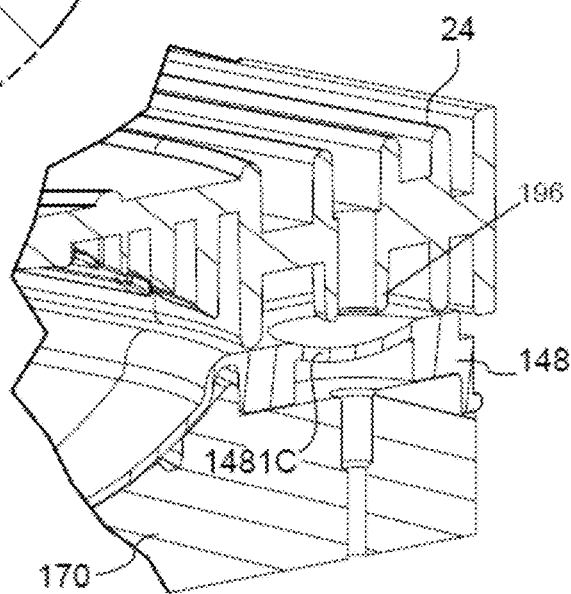
Figure 21A:
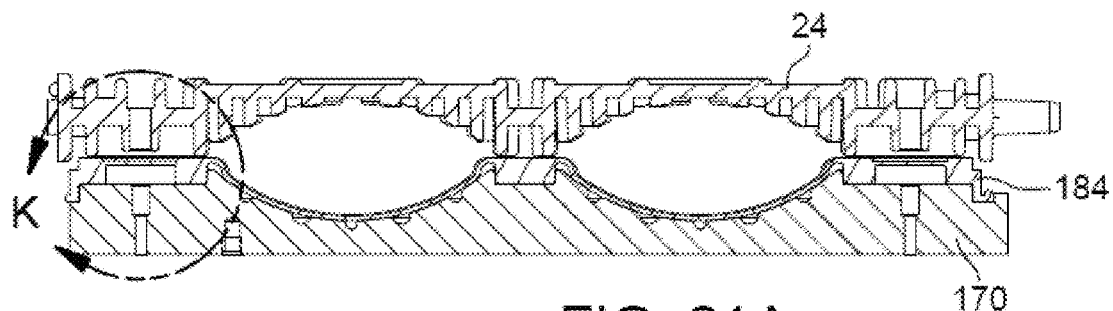
FIGS. 21A-C show cross-sectional views of a cassette valve seat and gasket valve control region, the valve control region biased in a neutral position with respect to the surface of the control gasket.
Figure 21B:
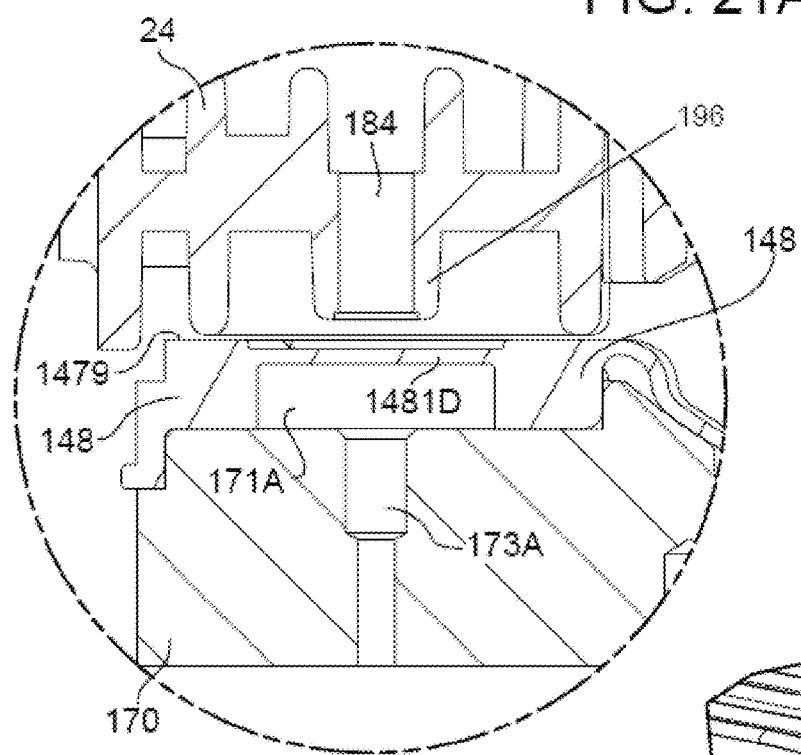
Figure 21C:
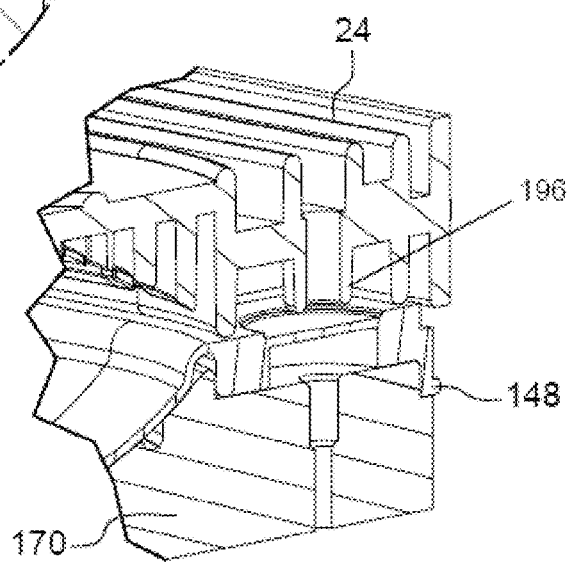

The valve control region 1481C of the arrangement shown in FIGS. 20A-C provides an inverted shape, which facilitates the lifting of the cassette membrane from the valve seat 196 under negative pressure. There is a reduced transition region between the actuation region 1481C and the surrounding gasket 148, which could result in less positive force being available to seal the cassette membrane against the valve seat 196. The presence or patency of a vacuum channel may be compromised in this configuration, but this configuration may also allow for less air volume being trapped between the gasket 148 and cassette membrane 15 when air is evacuated between the two surfaces. The valve control region 1481D of FIGS. 21A-C provides a similar effect, and likely provides for maximal elimination of any air pockets between cassette membrane and gasket. Although the vacuum channel may be compromised, in these cases the movement of the valve control region 1481D of the gasket 148 is likely to be more faithfully reproduced by the adjacent cassette membrane 15 (there being less dampening effect caused by the present of one or more air pockets in the intervening space).

Figure 22A:
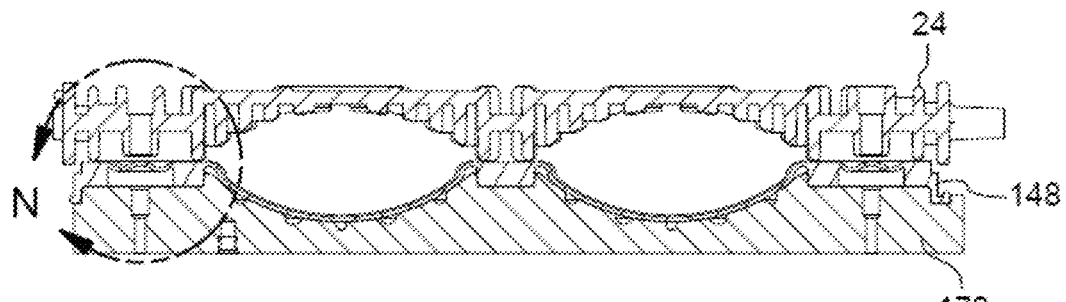
FIGS. 22A-C show cross-sectional views of a cassette valve seat and gasket valve control region, the valve control region being rippled at or below the surface of the control gasket.
Figure 22B:
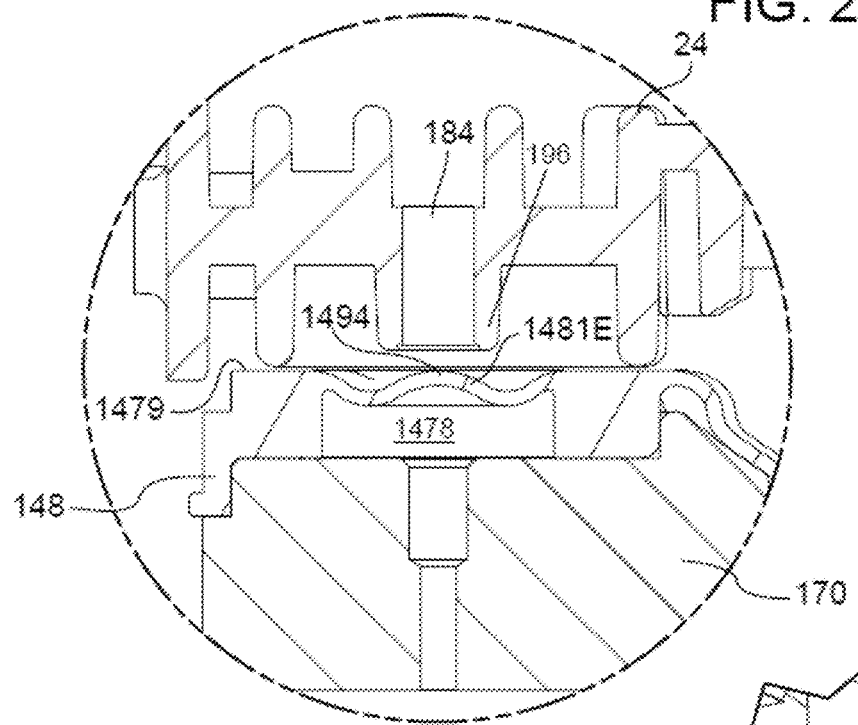
Figure 22C:
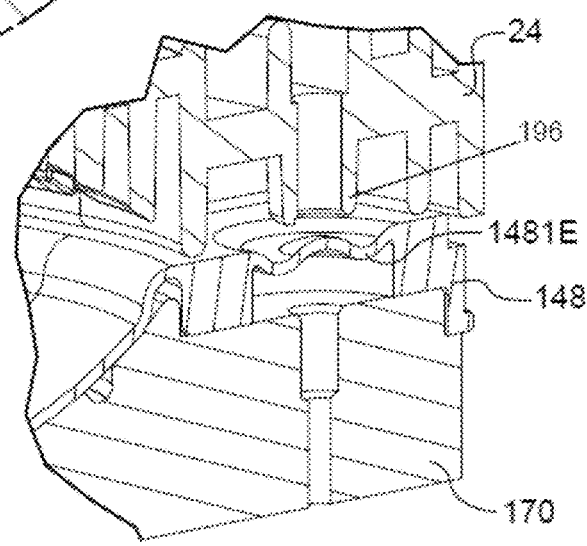

The arrangement shown in FIGS. 22A-C provides a control gasket valve control region 1481E that is partially folded or pleated, creating a rippling or undulation of the surface. The material forming the valve control region has been molded to have a rippled, wavy, or undulated form, preferably arranged in a concentric manner across the valve control region 1481E. This results in a surface area of material forming the valve control region 1481E being greater than a surface area provided to the valve control region on the plane 1479 of the control gasket. In this case, the rippled surface of the valve control region 1481E of the control gasket 148 adds an amount of slack or floppiness that provides for enhanced transmission of opening or closing forces against the valve seat 196 (with less expenditure of pressure to deform the valve control region away from its biased configuration at rest). The effect in this case is to increase the slack or floppiness of the valve control region 1481E, which facilitates its movement both toward and away from the valve seat 196. In the example shown, the control region 1481E forms a crest 1494 opposite the valve orifice 184, and forms a trough opposite the valve seat edge 196 (see, e.g., FIG. 22B). The operation of this valve control region 1481E may be expected to allow for reliable closing of the valve for any given application of positive pressure, but the opening created around the valve seat may not be fully optimized.

It is also more likely that in this arrangement, air pockets or gaps between the cassette membrane and valve control region 1481E of the gasket 148 may not be fully evacuated, because of the difference between the surface area of the material forming the cassette membrane 15 valve control region and the surface area of the material forming the valve control region 1481E of the gasket. The degree of rippling of the valve control region 1481E can be controlled in the molding process so that the cassette membrane 15 continues to move in tandem with the gasket valve control region 1481E in a manner sufficient to preserve adequate operation of the valve.

Figure 23A:
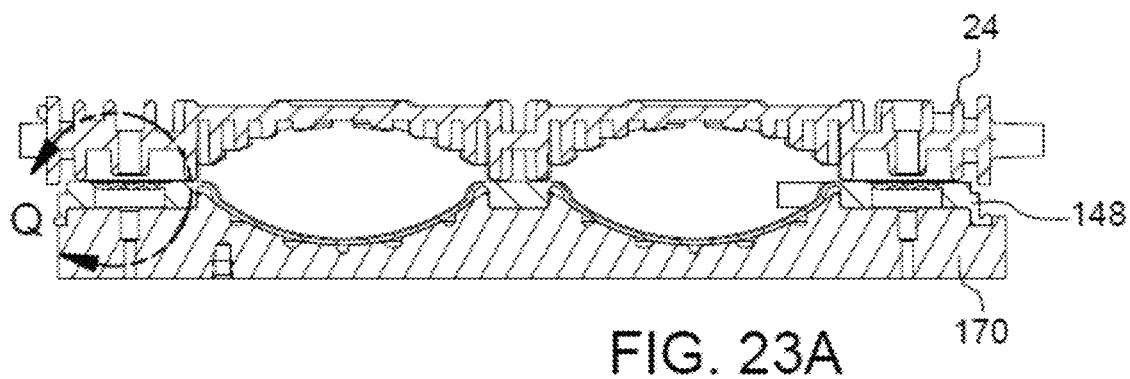
FIGS. 23A-C show cross-sectional views of a cassette valve seat and gasket valve control region, the valve control region being rippled at or below the surface of the control gasket.
Figure 23B:
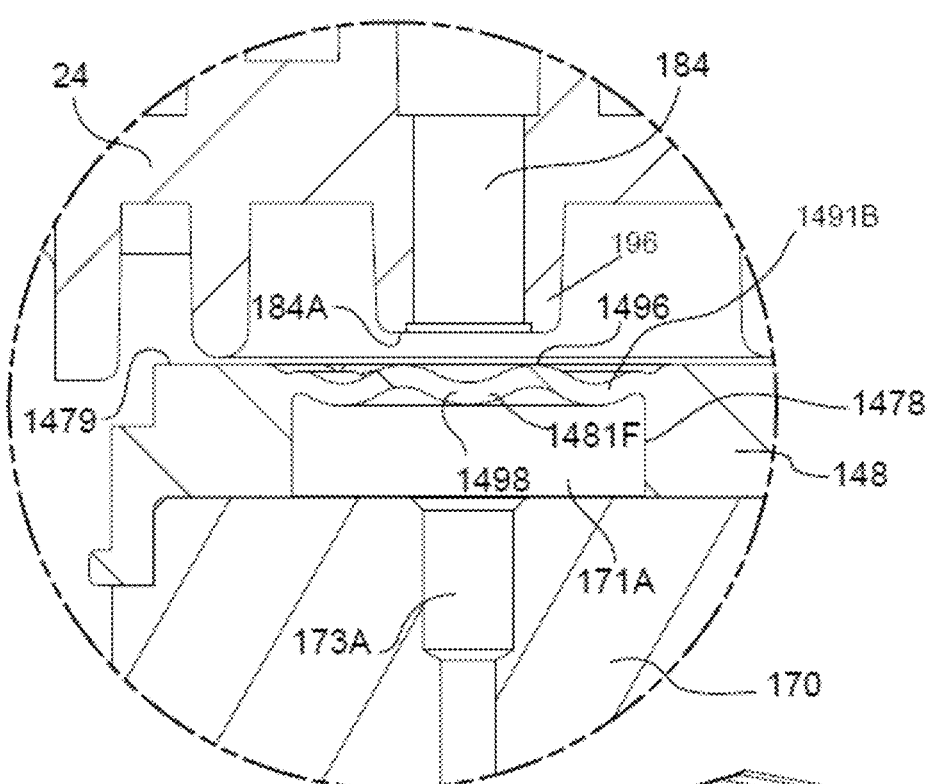
Figure 23C:
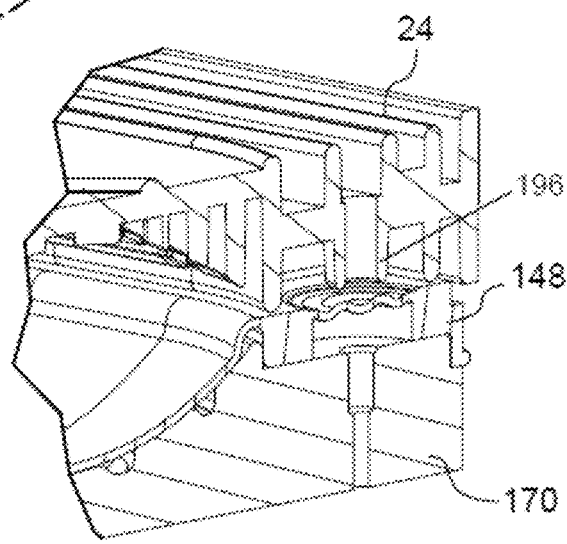

In contrast, the valve control region 1481F of the control gasket 148 depicted in FIGS. 23A-C may provide a more appropriate balance between maximizing the opening of the valve under negative pressure and providing a reliable and leak-free closure of the valve when positive pressure is applied. The material forming the valve control region 1481F has been molded to have a rippled, wavy or undulating form, in this case forming concentric ripples across the valve control region 1481F. This results in a surface area of material forming the valve control region being greater than a surface area provided by the valve control region on the plane 1479 of the control gasket. In this case, the rippled surface of the valve control region 1481F of the control gasket 148 adds an amount of slack or floppiness that provides for enhanced transmission of opening or closing forces against the valve seat 196 (with less expenditure of pressure to deform the valve control region away from its biased configuration at rest). In the example shown, the crest 1496 of the ripple pattern is opposite the edge or wall 196 of the valve seat, with the trough 1498 now being located at the center of the valve control region, opposite the valve orifice 184, as shown in FIG. 23B. This creates a bias in the gasket oriented toward sealing the cassette membrane 15 against the valve seat 196, while still providing for relatively unrestricted movement of the valve control region 1481F under both positive and negative pressure. This arrangement may provide an improved compromise between both opening and closing the valve. Reliable and effective valve closure is achieved under positive pressure, while enhanced fluid flow across the valve and reduced membrane oscillation and vibratory noise are achieved under negative pressure. In this embodiment, a secondary trough outside the valve seat 196 may function as a vacuum channel 1491B.

Figure 24:
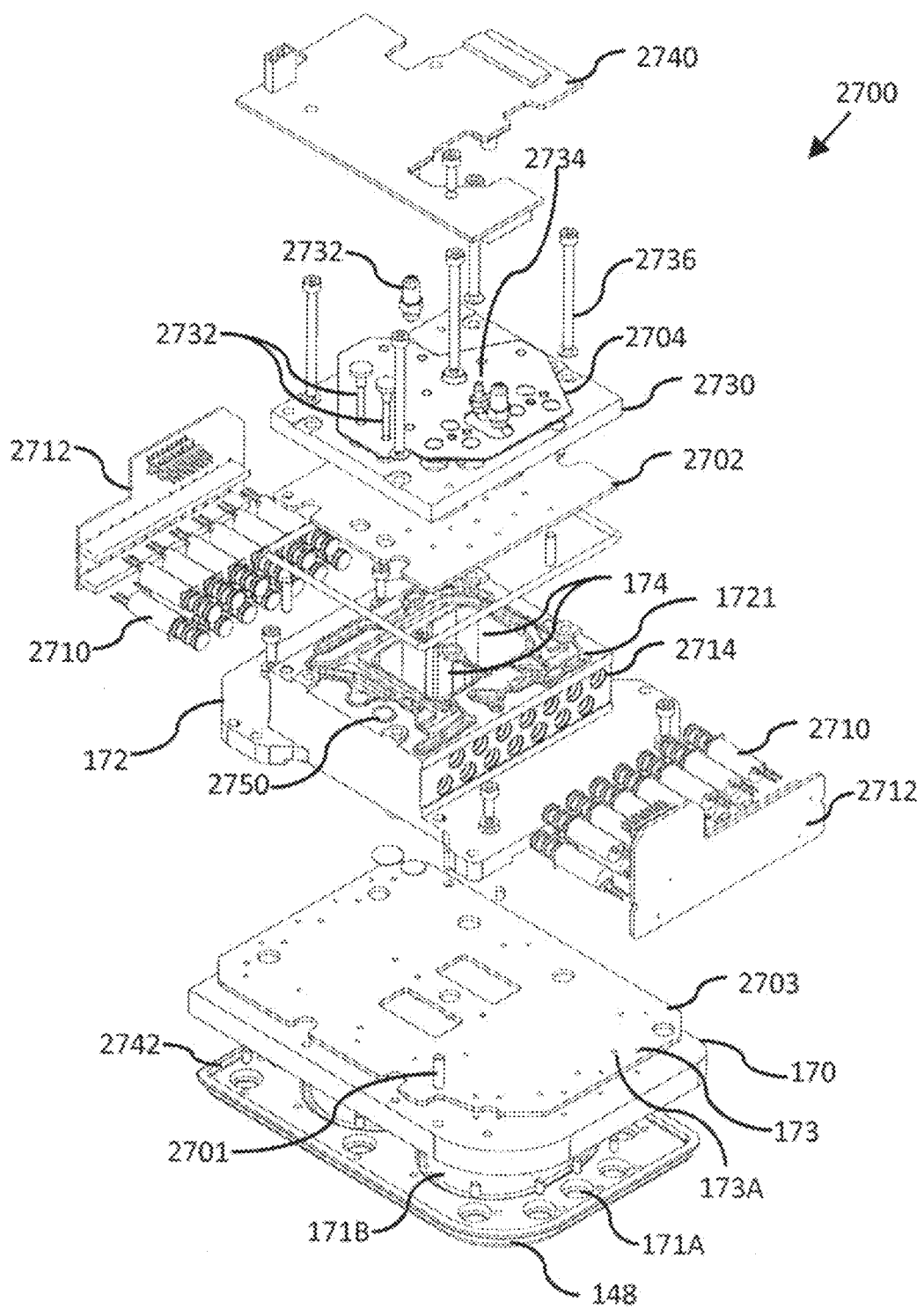
FIG. 24 is an exploded view of the integrated manifold.
Figure 25:
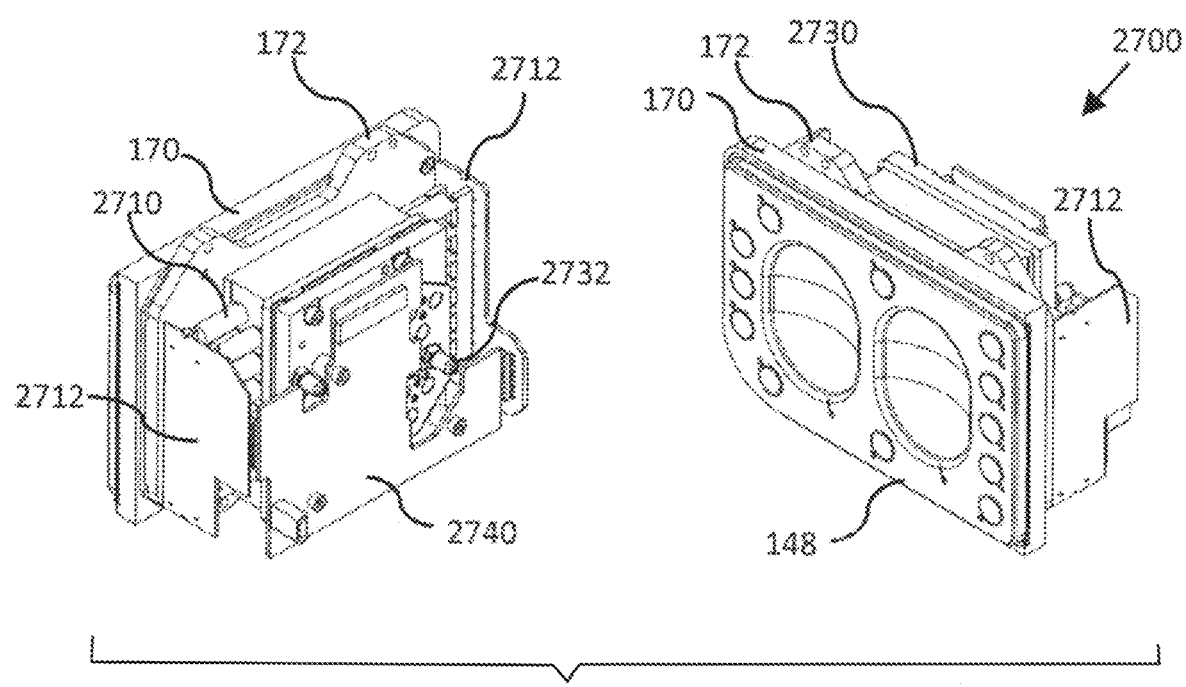
FIG. 25 shows two isometric views of the integrated manifold.

FIG. 24 shows an exploded view of an integrated pressure distribution module or assembly 2700 for use in a fluid flow control apparatus for operating a pumping cassette, and suitable for use as pressure distribution manifold 172 and mating block 170 of cycler 14. FIG. 25 shows an assembled view of integrated module 2700. The integrated module 2700 shown in these drawings comprises a pneumatic manifold or block 172, ports 2714 for supply pressures, pneumatic control valves 2710, pressure sensors 2740, a pressure delivery or mating block 170 and a control surface or actuator 148 that includes regions comprising flexible membranes for actuating pumps 171B and valves 171A on a pumping cassette. The integrated module 2700 may also include reference chambers 174 within the pneumatic manifold 172 for a pressure/volume measurement process for determining the volume of fluid present in a pumping chamber of a pumping cassette based on the ideal gas laws. The integrated module 2700 may also comprise a vacuum port 1483 (in the gasket 148—see e.g. FIG. 11), a mating vacuum port 173B of the pressure delivery block 170 (see, e.g. FIG. 13 or FIG. 14) and a set of pathways or channels from interfaces between the actuator or gasket 148 and flexible pump and valve membranes 15 of a pumping cassette to a fluid trap 1722 and liquid detection system 2670 in the manifold 172 (see, e.g., the pressure distribution schematic illustrated in FIG. 26). In some embodiments, the pneumatic manifold 172 may be formed as a single block. In other embodiments, the pneumatic manifold 172 may be formed from two or more manifold blocks mated together with gaskets positioned between the manifold blocks. The integrated module 2700 occupies a relatively small space in a fluid flow control apparatus, and eliminates the use of tubes or flexible conduits connecting the manifold ports with corresponding ports of a pressure delivery module or block mated to a pumping cassette. Among other possible advantages, the integrated module 2700 reduces the size and assembly cost of the pneumatic actuation assembly of a peritoneal dialysis cycler, which may result in a smaller and less expensive cycler. Additionally, the short distances between pressure or vacuum distribution ports on the pressure distribution manifold block and corresponding pressure or vacuum delivery ports 173A, 173B, 173C on a mating pressure delivery block 170, together with the rigidity of the conduits connecting the ports, may improve the responsiveness of an attached pumping cassette and the accuracy of cassette pump volume measurement processes. When used in a peritoneal dialysis cycler 14, in an embodiment, an integrated module comprising a metallic pressure distribution manifold mated directly to a metallic pressure delivery block may also reduce any temperature differences between the control volume 171B and the reference chamber 174 of the cycler 14, which may improve the accuracy of the pump volume measurement process.

An exploded view of the integrated module 2700 is presented in FIG. 24. The actuator surface, mounted on a mating block or pressure delivery block, is analogous or equivalent to the gasket or control surface 148, that includes flexible regions arranged to move back and forth to pump fluid and/or open and close valves by pushing or pulling on a membrane 15 of a pump cassette 24. With respect to cycler 14, the control gasket 148 is actuated by the positive and negative pneumatic pressure supplied to the control volumes 171A, 171B behind the control regions 1481, 1482. The control gasket 148 attaches to the pressure delivery block or mating block 170 by fitting tightly on a raised surface 2744 on the front surface of the mating block 170 with a lip 2742. The mating block 170 may include one or more surface depressions 2746 to align with and support the oval curved shape of one or more corresponding pump control surfaces 1482, forming a pump control chamber. A similar arrangement, with or without a surface depression, may be included in forming a valve control region 171A to align with a corresponding control surface 1481 for controlling one or more valves of a pumping cassette. The mating block 170 may further include grooves 2748 on the surface of depression 2746 of mating block 170 behind the pump control surface 1482 to facilitate the flow of control fluid or gas from the port 173C to the entire back surface the pump control surface 1482. Alternatively, rather than having grooves 2748, the depression 2746 may be formed with a roughened surface or a tangentially porous surface.

The mating block 170 connects the pressure distribution manifold 172 to the control gasket 148, and delivers pressure or vacuum to various control regions on control gasket 148. The mating block 170 may also be referred to as a pressure delivery block in that it provides pneumatic conduits to supply pressure and vacuum to the valve control regions 1481 and the pump control regions 1482, vacuum to the vacuum ports 1483 and connections from the pump control volumes 171B to the pressure sensors. The ports 173A connect the valve control volumes 171A to the pressure distribution manifold 172. The ports 173C connect the pump control volume 171B to the pressure distribution manifold 172. The vacuum ports 1483 are connected to the pressure distribution manifold 172 via ports 173B. In one embodiment, the ports 173B extend above the surface of the pressure delivery block 170 to pass through the control gasket 148 to provide vacuum at port 1483 without pulling the control surface 148 onto the port 173B and blocking flow.

The pressure delivery block 170 is attached to the front face of the pressure distribution manifold 172. The ports 173A, 173B, 173C line up with pneumatic circuits on the pressure distribution manifold 172 that connect to valve ports 2714. In one example, the pressure delivery block 170 is mated to the pressure distribution manifold 172 with a front flat gasket 2703 clamped between them. The block 170 and manifold 172 are held together mechanically, which in an embodiment is through the use of bolts 2736 or other types of fasteners. In another example, rather than a flat gasket 2703, compliant elements are placed in or molded in either the pressure delivery block 170 or the pressure distribution manifold 172. Alternatively, the pressure delivery block 170 may be bonded to the pressure distribution manifold 172 by an adhesive, double sided tape, friction welding, laser welding, or other bonding method. The block 170 and manifold 172 may be formed of metal or plastic and the bonding methods will vary depending on the material.

The pressure distribution manifold 172 contains ports for the pneumatic valves 2710, reference chambers 174, a fluid trap 1722 and pneumatic circuitry or of the integrated module 2700 connections provides pneumatic connections between the pressure reservoirs, valves, and contains ports 2714 that receive multiple cartridge valves 2710. The cartridge valves 2710 include but are not limited to the binary valves 2660 controlling flow to valve control volumes 171A, the binary valves X1A, X1B, X2, X3 controlling flow to pump control volumes 171B, and the binary valves 2661-2667 controlling flow to the bladders 2630, 2640, 2650 and pressure reservoirs 2610, 2620. The cartridge valves 2710 are pressed into the valve ports 2714 and electrically connected to the hardware interface 310 via circuit board 2712.

The pneumatic circuitry in the pressure distribution manifold 172 may be formed with a combination of grooves or slots 1721 on the front and back faces and approximately perpendicular holes that connect the grooves 1721 on one face to valve ports 2714, the fluid trap 1722 and to grooves and ports on the opposite face. Some grooves 1721 may connect directly to the reference chambers 174. A single perpendicular hole may connect a groove 1721 to multiple valve ports 174 that are closely spaced and staggered. Sealed pneumatic conduits are formed when the grooves 1721 are isolated from one another by, in one example, the front flat gasket 2703 as shown in FIG. 24.

The presence of liquid in the fluid trap 1722 (FIG. 26) may be detected by a pair of conductivity probes 2732 (FIG. 24). The conductivity probes 2732 slide through a back gasket 2704, a back plate 2730 and holes 2750 before entering the fluid trap 1722 in the pressure distribution manifold 172.

The back plate 2730 seals the reference volumes 174, the grooves 1721 on the back face of the pressure distribution manifold 172 and provides ports for the pressure sensors 2740 and ports for pressure and vacuum lines 2734 and vents to the atmosphere 2732. In one example, the pressure sensors may be IC chips soldered to a single board 2740 and pressed as a group against the back gasket 2704 on the back plate 2730. In one example, bolts 2736 clamp the back plate 2730, pressure distribution manifold 172 and pressure delivery block 170 together with gaskets 2703, 2702 between them. In another example, the back plate 2730 may be bonded to the pressure delivery manifold 172 as described above. The assembled integrated module 2700 is presented in FIG. 26.

Figure 26:
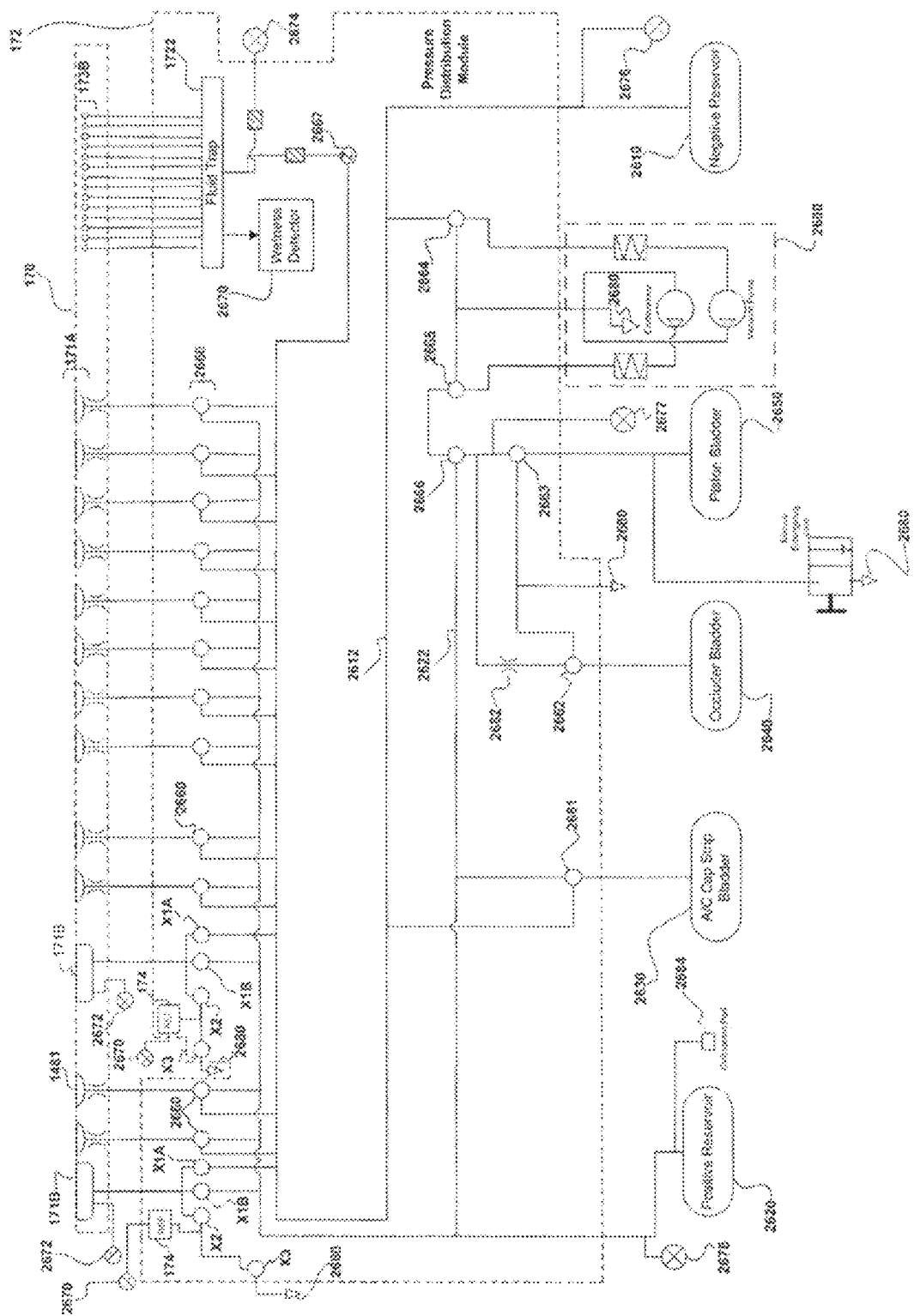
FIG. 26 shows a schematic of the pneumatic system that controls fluid flow through the cycler.

FIG. 26 presents a schematic of the pneumatic pressure circuit in the integrated manifold 2700 and pneumatic elements outside the manifold. The pump 2600 produces vacuum and pressure. The pump 2600 is connected via 3 way valves 2664 and 2665 to a vent 2680 and the negative or vacuum reservoir 2610 and the positive reservoir 2620. Pressures in the positive and negative reservoirs 2620, 2610 are measured respectively by pressure sensors 2678, 2676. The hardware interface 310 controls the speed of the pump 2600 and the position of 3-way valves 2664, 2665, 2666 to control the pressure in each reservoir. The auto-connect stripper element bladder 2630 is connected via 3-way valve 2661 to either the positive pressure line 2622 or the negative or vacuum line 2612. The automation computer 300 commands the position of valve 2661 to control the location of the stripper element 1461. The occluder bladder 2640 and piston bladder 2650 are connected via 3-way valves 2662 and 2663 to either the pressure line 2622 or vent 2680. The automation computer 300 commands valve 2663 to connect the piston bladder 2650 to the pressure line 2622 after the door 141 is closed to securely engage the cassette 24 against the control gasket 148. The occluder bladder 2640 is connected to the pressure line 2622 via valve 2662 and restriction 2682. The occluder bladder 2640 is connected to the vent 2680 via valve 2662. The orifice 2682 advantageously slows the filling of the occluder bladder 2640 that retracts the occluder 147 in order to maintain the pressure in the pressure line 2622. The high pressure in the pressure line 2622 keeps the various valve control surfaces 171A and the piston bladder 2650 actuated against the cassette 24, which prevents flow to or from the patient as the occluder 147 opens. Conversely the connection from the occluder bladder 2640 to the vent 2680 is unrestricted, so that occluder 147 can quickly close.

The valve control surfaces 1481 are controlled by the pressure in the valve control volume 171A, which in turn is controlled by the position of the 3-way valves 2660. The valves 2660 can be controlled individually via commands from the automation computer 300 passed to the hardware interface 310. The valves controlling the pumping pressures in the pump control volumes 171B are controlled with 2-way valves X1A, X1B. The valves X1A, X1B in one example may be controlled by the hardware interface 310 to achieve a pressure commanded by the automation computer 300. The pressure in each pump control chamber 171B is measured by sensors 2672. The pressure in the reference chambers is measured by sensors 2670. The 2-way valves X2, X3 respectively connect the reference chamber 174 to the pump control chamber 171B and the vent 2680.

The fluid trap 1722 is connected to the vacuum line 2612 during operation as explained elsewhere in this application. The fluid trap 1722 is connected by several lines to the ports 173B in the pressure delivery block 170. The pressure in the fluid trap 1722 is monitored by pressure sensor 2674 that is mounted on the back plate 2730.

The vacuum ports 1483 may be employed to separate the membrane 15 from the control gasket 148 at the end of therapy before or during the opening the door. The vacuum provided by the negative pressure source to the vacuum ports 1483 sealingly engages the membrane 15 to the control gasket 148 during therapy. In some instances a substantial amount of force may be needed to separate the control surface from the cassette membrane 15, preventing the door 141 from freely rotating into the open position, even when the application of vacuum is discontinued. Thus, in an embodiment, the pressure distribution module 2700 is configured to provide a valved channel between the positive pressure source and the vacuum ports 1483. Supplying positive pressure at the vacuum ports 1483 may aid in separating the membrane 15 from the control gasket 148, thereby allowing the cassette 24 to separate more easily from the control gasket 148 and allow the door 141 to open freely. The pneumatic valves in the cycler may be controlled by the automation computer 300 to provide a positive pressure to the vacuum ports 1483. The manifold 172 may include a separately valved channel dedicated for this purpose, or alternatively it may employ the existing channel configurations and valves, operated in a particular sequence.

In one example, the vacuum ports 1483 may be supplied with positive pressure by temporarily connecting the vacuum ports 1483 to the positive pressure reservoir 2620. The vacuum ports 1483 are normally connected to the vacuum reservoir 2610 via a common fluid collection chamber or fluid trap 1722 in the manifold 172 during therapy. In one example, the controller or automation computer may open valve X1B between the positive pressure reservoir and the volume control chamber 171B and the valve X1A between the negative pressure reservoir and the same volume control chamber 171B simultaneously, which will pressurize the air in the fluid trap 1722 and the vacuum ports 1483. The pressurized air will flow through the vacuum ports 1483 and between the membrane 15 and the control gasket 148, breaking any vacuum bond between the membrane and control surface. However, in the illustrated manifold, the stripper element 1491 of the cap stripper 149 may extend while the positive pressure is supplied to common fluid collection chamber 1722 fluid, because the stripper bladder 2630 is connected to a the vacuum supply line 2612. In this example, in a subsequent step, the fluid trap 1722 may be valved off from the now-pressurized vacuum line and the two valves X1A, X1B connecting the positive and vacuum reservoirs to the volume control chamber 171B may be closed. The vacuum pump 2600 is then operated to reduce the pressure in the vacuum reservoir 2610 and the vacuum supply line 2612, which in turn allows the stripper element 1491 to be withdrawn. The door 141 may then be opened after detaching the cassette 24 from the control gasket 148 and retracting the stripper element 1491.

In accordance with an aspect of the disclosure, the vacuum ports 1483 may be used to detect leaks in the membrane 15, e.g., a liquid sensor in a conduit or chamber connected to a vacuum port 1483 may detect liquid if the membrane 15 is perforated or liquid otherwise is introduced between the membrane 15 and the control gasket 148. For example, vacuum ports 1483 may align with and be sealingly associated with complementary vacuum ports 173B in mating block 170, which in turn may be sealingly associated with fluid passages 1721 leading to a common fluid collection chamber 1722 in manifold 172. The fluid collection chamber 1722 may contain an inlet through which vacuum can be applied and distributed to all vacuum ports 1483 of control gasket 148. By applying vacuum to the fluid collection chamber 1722, fluid may be drawn from each of the vacuum ports 173B and 1483, thus removing fluid from any space between the membrane 15 and the control gasket 148 at the various control regions. However, if there is liquid present at one or more of the regions, the associated vacuum port 1483 may draw the liquid into the vacuum ports 173B and into the lines 1721 leading to the fluid collection chamber 1722. Any such liquid may collect in the fluid collection chamber 1722, and be detected by one or more suitable sensors, e.g., a pair of conductivity sensors that detect a change in conductivity in the chamber 1722 indicating the presence of liquid. In this embodiment, the sensors may be located at a bottom side of the fluid collection chamber 1722, while a vacuum source connects to the chamber 1722 at an upper end of the chamber 1722. Therefore, if liquid is drawn into the fluid collection chamber 1722, the liquid may be detected before the liquid level reaches the vacuum source. Optionally, a hydrophobic filter, valve or other component may be placed at the vacuum source connection point into the chamber 1722 to help further resist the entry of liquid into the vacuum source. In this way, a liquid leak may be detected and acted upon by controller 16 (e.g., generating an alert, closing liquid inlet valves and ceasing pumping operations) before the vacuum source valve is placed at risk of being contaminated by the liquid.

In the example schematic shown in FIG. 26, a calibration port 2684 is depicted. The calibration port 2684 may be used to calibrate the various pressure sensors 2670, 2672, 2674, 2676, 2677, 2678 in the pneumatic system. For example, a pressure reference may be connected to the pneumatic circuit of the cycler via the calibration port 2684. With the pressure reference connected, the valves of the pneumatic system may be actuated so as to connect all of the pressure sensors 2670, 2672, 2674, 2676, 2677, 2678 to the same fluid volume. A known pressure may then be established in the pneumatic system using the pressure reference. The pressure readings from each of the pressure sensors 2670, 2672, 2674, 2676, 2677, 2678 may be compared to the known pressure of the pressure reference and the pressure sensors 2670, 2672, 2674, 2676, 2677, 2678 may then be calibrated accordingly. In some embodiments, selected pressure sensors of the pressure sensors 2672, 2674, 2676, 2677, 2678 may be connected and brought to the pressure of the reference for calibration in groups or individually.

Any fluid handling device (i.e. base unit) that is configured to actuate diaphragm-based pumps and valves on a removable cassette can take advantage of its pneumatic (or hydraulic) cassette interface to receive a calibrating reference pressure via a specialized calibrating cassette (or 'cassette fixture'). A calibrating cassette can have the same overall dimensions as a standard fluid pumping cassette, so that it can provide a sealing interface with the cassette interface or control surface of the base unit. One or more of the pump or valve regions can be allowed to communicate with a corresponding region of the interface to which it mates, so that a reference pneumatic or hydraulic pressure can be introduced through the calibrating cassette and into the pneumatic or hydraulic flow paths of the base unit (e.g. via a pneumatic or hydraulic manifold).

For example, in a pneumatically operated peritoneal dialysis cycler, the pneumatic circuitry of the cycler may be accessed directly through the cassette interface of the cycler. This may for example, be accomplished using a modified cassette or cassette fixture which allows the control surface 148 to create a seal against the cassette fixture. Additionally, the cassette fixture may be constructed to include at least one access port in fluid communication with a vacuum port 173B of the cassette interface. In the absence of a vacuum port (e.g. in embodiments having slits or perforations in the control surface) the access port may instead be placed in communication with the vacuum vent feature of the cassette interface or control surface.

The cassette fixture (or calibrating cassette) may be constructed to have a direct flow path from an external cassette port to the access port facing the device interface, the external cassette port then being available for connection to a pressure reference. As described above, all or some of the pressure sensors 2670, 2672, 2674, 2676, 2677, 2678 may be placed into fluid communication with a common volume, through the appropriate actuation of pneumatic control valves in the pressure distribution manifold. A known pressure may be established in that volume using the pressure reference. The pressure readings from each of the pressure sensors 2670, 2672, 2674, 2676, 2677, 2678 may be compared to the known pressure of the pressure reference and the pressure sensors 2670, 2672, 2674, 2676, 2677, 2678 may then be calibrated accordingly.

In some embodiments of a pressure distribution manifold, it may not be possible for all of the pressure sensors 2670, 2672, 2674, 2676, 2677, 2678 to be connected to a common volume at one time. In that case, the flow paths to the individual pressure sensors 2670, 2672, 2674, 2676, 2677, 2678 may need to be opened in a sequential manner to ensure calibration of all sensors. Additionally, it should be noted that once calibrated, one or more of the pressure sensors 2670, 2672, 2674, 2676, 2677, 2678 may be used to calibrate other pressure sensors 2670, 2672, 2674, 2676, 2677, 2678 in a pressure distribution manifold of a base unit or cycler. The previously calibrated pressure sensor or sensors may be placed into a common volume with the uncalibrated pressure sensor (e.g. via suitable valve actuations). The pressure of the common volume may be known via the calibrated pressure sensor(s). The uncalibrated pressure sensor's reading may be compared to the known pressure of the common volume and then calibrated accordingly.

Figure 27:
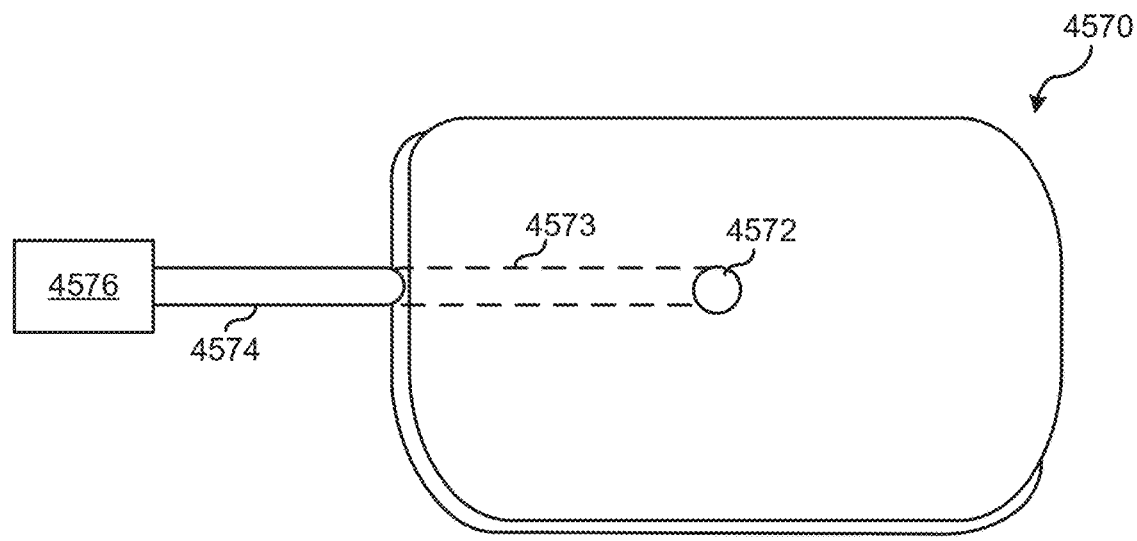
FIG. 27 is a front side view of an embodiment of a cassette fixture.

FIG. 27 depicts a schematized view of an embodiment of a cassette fixture 4570. As shown, the cassette fixture 4570 has the same outline as a standard pump cassette 24 described earlier. The cassette fixture 4570 includes an access port 4572 associated with a specific valve or pump region of a standard cassette to align with its corresponding region on the cassette interface (control surface 148) of the base unit. The cassette fixture 4570 otherwise can have a flat smooth interface surface to allow the control surface to seal against it when it is mated to the base unit or cycler. Preferably, the cassette fixture 4570 is formed from a metal or other hard, stiff material. A resistance to flexing or deformation under pressure may help to increase reliability and consistency over multiple calibrations of multiple cyclers. As shown, the cassette fixture 4570 includes an access port 4572 which is recessed into the face of the cassette fixture 4570. The access port 4572 communicates with a fluid path 4573 extending to tubing 4574 leading away from the cassette fixture 4570. A cassette port or fitting may be included on the side of the cassette for connection via tubing to a reference pressure source 4576 in the example embodiment.

Figure 28:
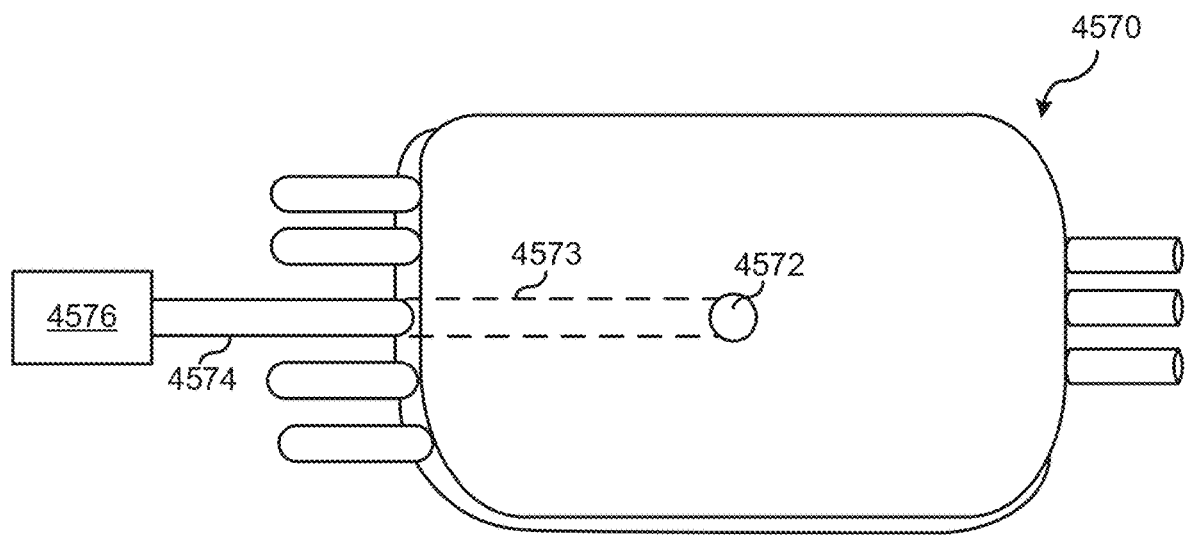
FIG. 28 shows another example of a cassette fixture which is made from a modified cassette such as the cassette shown in FIG. 3.
Figure 29:
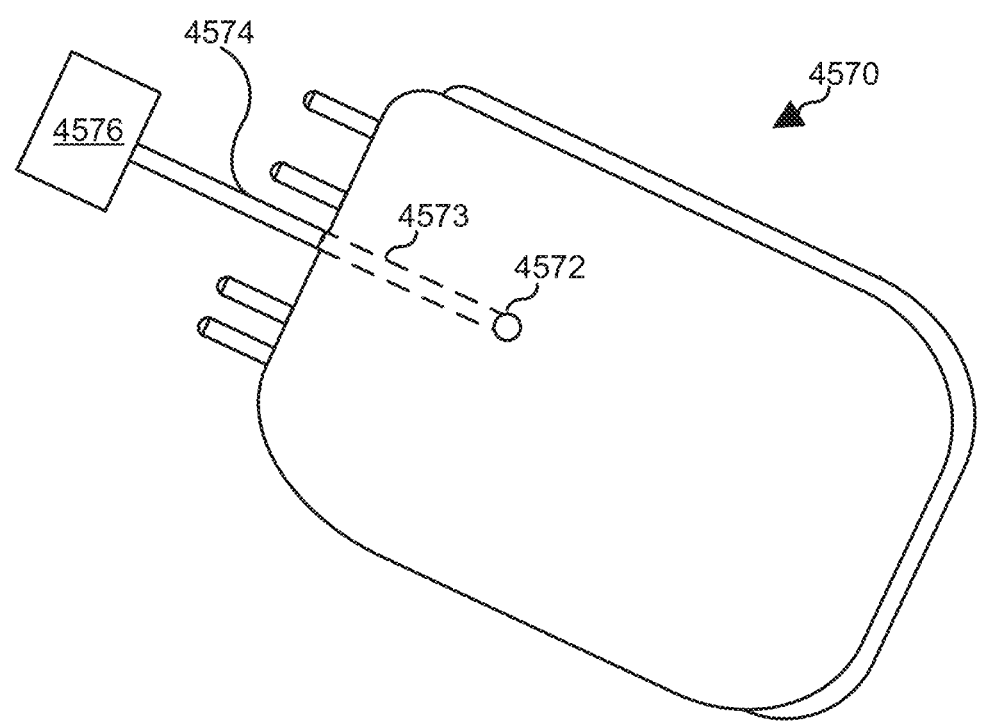
FIG. 29 shows another example of a cassette fixture which is made from a modified cassette.

FIGS. 28 and 29 depict other representations of a cassette fixture 4570 adapted from a modified cassette such as the cassette 24 shown in FIG. 3. In such examples, the cassette fixture 4570 may be made by removing or not including the sheeting or membrane 15 from the control side of the cassette which faces a control surface or cassette interface 148 (see, for example, FIG. 90) of a cycler when installed in the cycler. Referring to FIG. 3, for example, the membrane 15 may not be included on the cassette 24. Thus, the pneumatic circuit of the cycler may be accessed directly through the cassette 24. Alternatively, the membrane or sheeting may be interrupted (e.g. removed, perforated, slit, or the like) on only a portion of the cassette to create the cassette fixture 4570. For example, the membrane may be modified in this manner in the area over which an access port 4572 of the cassette fixture 4570 is located.

Additionally, tubing 4574 may be attached to one or more of the external connection sites of a standard cassette to create the necessary fluid communication path of a cassette fixture 4570. The external connection sites can include any tubing attachment sites on the standard cassette, or may comprise more robust fittings for repeated use in calibration procedures. Referring to FIG. 3, external connection sites may include the cassette spikes 160 and/or the ports 150, 152 and 154. The cassette may then be modified so that all other external connection sites may be blocked, plugged or otherwise sealed.

As above, the tubing 4574 leads from a fluid flowpath 4573 fluidically connected to an access port 4572 in the cassette fixture 4570 to provide a connection path to a pressure reference 4576. The access port 4572 may be a pre-existing opening or valve port in the cassette body. Additionally, the fluid path 4573 may be any pre-existing pathway or combination of pathways in the cassette body which allow fluid communication from the access port 4572 to the tubing 4574 or an associated fitting on the side of the cassette. For example, a fluid path 4573 may include one or more valve port, valve well, pump chamber, and/or channel in the cassette body or any combination thereof.

In one embodiment, the inner wall of the control chambers 171B can include raised elements somewhat analogous to the spacer elements 50 of the pump chamber, e.g., as shown in FIG. 13 for the control chambers 171B associated with the pump control regions 1482. These raised elements can take the form of plateau features, ribs, or other protrusions that keep the control ports recessed away from the fully retracted control regions 1482. This arrangement may allow for a more uniform distribution of pressure or vacuum in the control chamber 171B, and prevent premature blocking of any control port by the control gasket 148. A pre-formed control gasket 148 (at least in the pump control regions) may not be under a significant stretching force when fully extended against either the inner wall of the pump chamber of the cassette 24 during a delivery stroke, or the inner wall of the control chamber 171 during a fill stroke. It may therefore be possible for the control region 1482 to extend asymmetrically into the control chamber 171B, causing the control region 1482 to prematurely close off one or more ports of the control chamber before the chamber is fully evacuated. Having features on the inner surface of the control chamber 171B that prevent contact between the control region 1482 and the control ports may help to assure that the control region 1482 can make uniform contact with the control chamber inner wall during a fill stroke.

As suggested above, the cycler 14 may include a control system 16 with a data processor in electrical communication with the various valves, pressure sensors, motors, etc., of the system and is preferably configured to control such components according to a desired operating sequence or protocol. The control system 16 may include appropriate circuitry, programming, computer memory, electrical connections, and/or other components to perform a specified task. The system may include pumps, tanks, manifolds, valves or other components to generate desired air or other fluid pressure (whether positive pressure—above atmospheric pressure or some other reference—or negative pressure or vacuum—below atmospheric pressure or some other reference) to control operation of the regions of the control gasket 148, and other pneumatically-operated components. Further details regarding the control system 16 (or at least portions of it) are provided below.

In one illustrative embodiment, the pressure in the pump control chambers 171B may be controlled by a binary valve, e.g., which opens to expose the control chamber 171 to a suitable pressure/vacuum and closes to cut off the pressure/vacuum source. The binary valve may be controlled using a saw tooth-shaped control signal which may be modulated to control pressure in the pump control chamber 171B. For example, during a pump delivery stroke (i.e., in which positive pressure is introduced into the pump control chamber 171B to move the membrane 15/control gasket 148 and force liquid out of the pump chamber 181), the binary valve may be driven by the saw tooth signal so as to open and close at a relatively rapid rate to establish a suitable pressure in the control chamber 171B (e.g., a pressure between about 70-90 mmHg). If the pressure in the control chamber 171B rises above about 90 mmHg, the saw tooth signal may be adjusted to close the binary valve for a more extended period. If the pressure drops below about 70 mmHg in the control chamber 171B, the saw tooth control signal may again be applied to the binary valve to raise the pressure in the control chamber 171. Thus, during a typical pump operation, the binary valve will be opened and closed multiple times, and may be closed for one or more extended periods, so that the pressure at which the liquid is forced from the pump chamber 181 is maintained at a desired level or range (e.g., about 70-90 mmHg).

In some embodiments, it may be useful to detect an "end of stroke" of the membrane 15/pump control region 1482, e.g., when the membrane 15 contacts the spacers 50 in the pump chamber 181 or the pump control region 1482 contacts the wall of the pump control chamber 171B. For example, during a pumping operation, detection of the "end of stroke" may indicate that the membrane 15/pump control region 1482 movement should be reversed to initiate a new pump cycle (to fill the pump chamber 181 or drive fluid from the pump chamber 181). In one illustrative embodiment in which the pressure in the control chamber 171B for a pump is controlled by a binary valve driven by a saw tooth control signal, the pressure in the pump chamber 181 will fluctuate at a relatively high frequency, e.g., a frequency at or near the frequency at which the binary valve is opened and closed. A pressure sensor in the control chamber 171B may detect this fluctuation, which generally has a higher amplitude when the membrane 15/pump control region 1482 are not in contact with the inner wall of the pump chamber 181 or the wall of the pump control chamber 171B. However, once the membrane 15/pump control region 1482 contacts the inner wall of the pump chamber 181 or the wall of the pump control chamber 171B (i.e., the "end of stroke"), the pressure fluctuation is generally damped or otherwise changes in a way that is detectable by the pressure sensor in the pump control chamber 171B. This change in pressure fluctuation can be used to identify the end of stroke, and the pump and other components of the cassette 24 and/or cycler 14 may be controlled accordingly.

Figure 31:
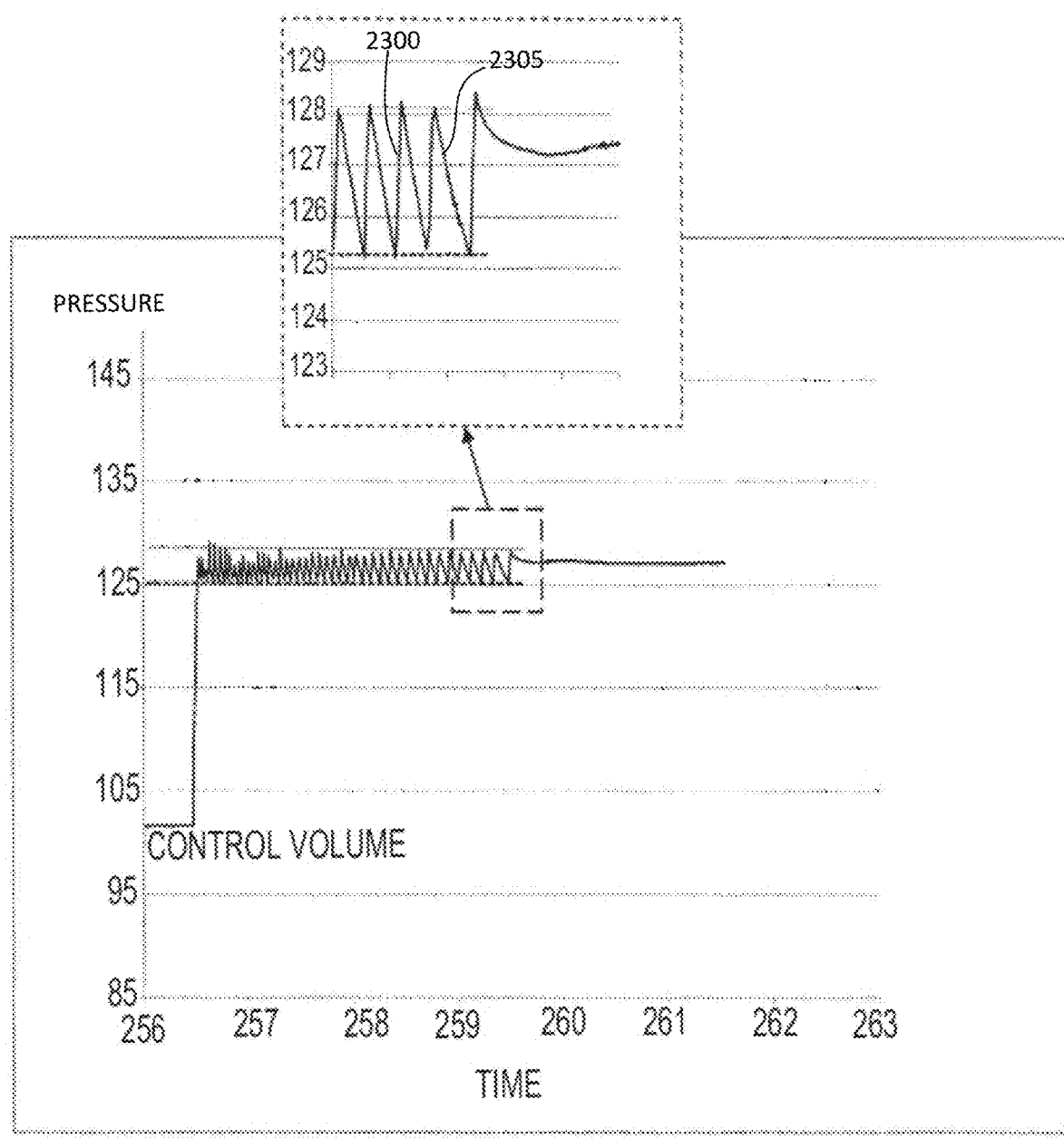
FIG. 31 shows a pressure tracing from a control or actuation chamber of a pumping cassette during a liquid delivery stroke.

In one embodiment, the pneumatic pressure applied to the control chamber 171B is actively controlled by a processor receiving a signal from a pressure transducer 2672 (FIG. 26) connected to the control chamber 171B and a fast acting binary valve X1A, X1B between a pressure reservoir 2620, 2610 and the control chamber 171B. The processor may control the pressure with a variety of control algorithms including closed loop proportional or proportional-integrator feedback control that varies the valve duty cycle to achieve the desired pressure in the control volume 171B. In one embodiment, the processor controls the pressure in the control chamber with an on-off controller often called a bang-bang controller. The on-off controller monitors the pressure in the control volume 171B during a deliver stroke and open the binary valve X1B (connecting the control volume 171B to the positive reservoir 2620) when the pressure is less than a lower first limit and closes the binary valve X1B when the pressure is above a higher second limit. During a fill stroke, the on-off controller opens the binary valve X1A (connecting the control volume 171B to the negative reservoir 2610) when the pressure is greater than a third limit and closes the binary valve X1A when the pressure is less than a fourth limit, where the fourth limit is lower than the third limit and both the third and fourth limits are less than the first limit. A plot of the pump control chamber pressure over time during a deliver stroke and the associated pressure measurement is shown in FIG. 31. The control chamber pressure oscillates between a lower first limit and a higher second limit as the membrane 15 moves across the control chamber 171B. The pressure stops oscillating between the limits when the membrane 15 stops moving. The membrane 15 typically stops moving when it contacts either the spacers 50 of the cassette or it contacts the control chamber surface 171B. The membrane 15 may also stop moving if the outlet fluid line is occluded.

The automation computer (AC) 300 detects the end of stroke by evaluating the pressure signals. There are many possible algorithms to detect the end of pressure oscillation that indicate the end-of-stroke (EOS). The algorithms and methods to detect EOS in the section labeled "Detailed Description of the system and Method of Measuring Change Fluid Flow Rate" in U.S. Pat. No. 6,520,747 and the section describing the filtering to detect end of stroke in U.S. Pat. No. 8,292,594 are herein incorporated by reference.

One example of an algorithm to detect EOS, the AC 300 evaluates the time between the pressure crossing the first and second limits during a deliver stroke or third and fourth limits during a fill stroke. The on-off controller opens and closes the valves X1A, X1B in response to the pressure oscillating between the two limits as the control chamber volume changes during the fill or deliver stroke. When the membrane 15 stops moving at the end-of-stroke, the pressure changes will significantly diminish so that the pressure no longer exceeds one or both limits. The AC 300 may detect EOS by measuring the time between the pressure exceeding alternating limits. If the time since the pressure crossed the last limit exceeds a predefined threshold, then the AC 300 may declare an EOS. The algorithm may further include an initial period during which the AC 300 does not measure the time between limit crossings.

In another example algorithm, the AC 300 evaluates the derivative of the pressure signal with respect to time. The AC 300 may declare an EOS, if the derivative remains below a minimum threshold for a minimum length of time. In a further example, the minimum threshold is the average of the absolute value of the average pressure derivative during the stroke. The algorithm calculates the slope (derivative with respect to time) of a curve fit to a set of data points, where the data points are taken from a moving window. The absolute value of each slope is then averaged over the stroke to calculate the absolute value of the average pressure derivative. In another example of an EOS algorithm, the AC 300 may not include the pressure data until after an initial delay. The AC 300 ignores the initial pressure data to avoid false EOS detections due to irregular pressure traces that occasionally occur during the early part of the stroke. In another example, the AC 300 declares an EOS only after the second derivative of the pressure in the later part of the stroke has remained below a threshold for a minimum time and a wait period of time has past.

The criteria to declare an EOS may be optimized for different pumping conditions. The optimized EOS detection conditions include the second pressure derivative threshold, the minimum time to remain below the second derivative threshold, the duration of the initial delay and a length of the wait period. These EOS detection criteria may be optimized differently, for example, the fill stroke from the bags 20, 22, the deliver stroke to the patient, the fill stroke from the patient, and the deliver stroke to the bags 20, 22. Alternatively each EOS detection criteria may be a function of the pumping pressure in the control chamber 171B.

Noise Reduction Features of the Cycler

In accordance with aspects of the invention, the cycler 14 may include one or more features to reduce noise generated by the cycler 14 during operation and/or when idle. In one aspect of the invention, the cycler 14 may include a single pump that generates both pressure and vacuum that are used to control the various pneumatic systems of the cycler 14. In one embodiment, the pump can simultaneously generate both pressure and vacuum, thereby reducing overall run time, and allowing the pump to run more slowly (and thus more quietly). In another embodiment, the air pump start and/or stop may be ramped, e.g., slowly increases pump speed or power output at starting and/or slowly decreases pump speed or power output at shut down. This arrangement may help reduce "on/off" noise associated with start and stop of the air pump so pump noise is less noticeable. In another embodiment, the air pump may be operated at a lower duty cycle when nearing a target output pressure or volume flow rate so that the air pump can continue operating as opposed to shutting off, only to be turned on after a short time. As a result, disruption caused by repeated on and off cycles of the air pump may be avoided.

Figure 32:
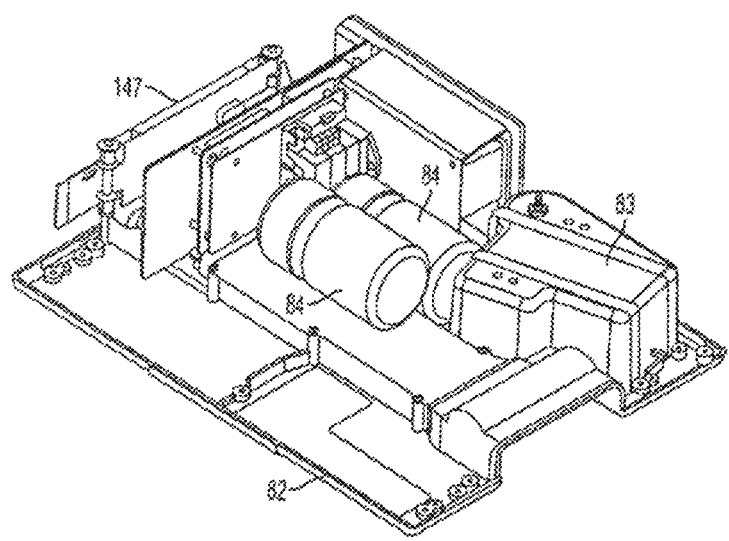
FIG. 32 is a perspective view of an interior section of the cycler of FIG. 1 with the upper portion of the housing removed.

FIG. 32 shows a perspective view of an interior section of the cycler 14 with the upper portion of the housing 82 removed. In this illustrative embodiment, the cycler 14 includes a single air pump 83, which includes the actual pump and motor drive contained within a sound barrier enclosure. The sound barrier enclosure includes an outer shield, such as a metal or plastic frame, and a sound insulation material within the outer shield and at least partially surrounding the motor and pump. This air pump 83 may simultaneously provide air pressure and vacuum, e.g., to a pair of accumulator tanks 84. One of the tanks 84 may store positive pressure air, while the other stores vacuum. A suitable manifold and valve arrangement may be coupled to the tanks 84 so as to provide and control air pressure/vacuum supplied to the components of the cycler 14.

Figure 30:
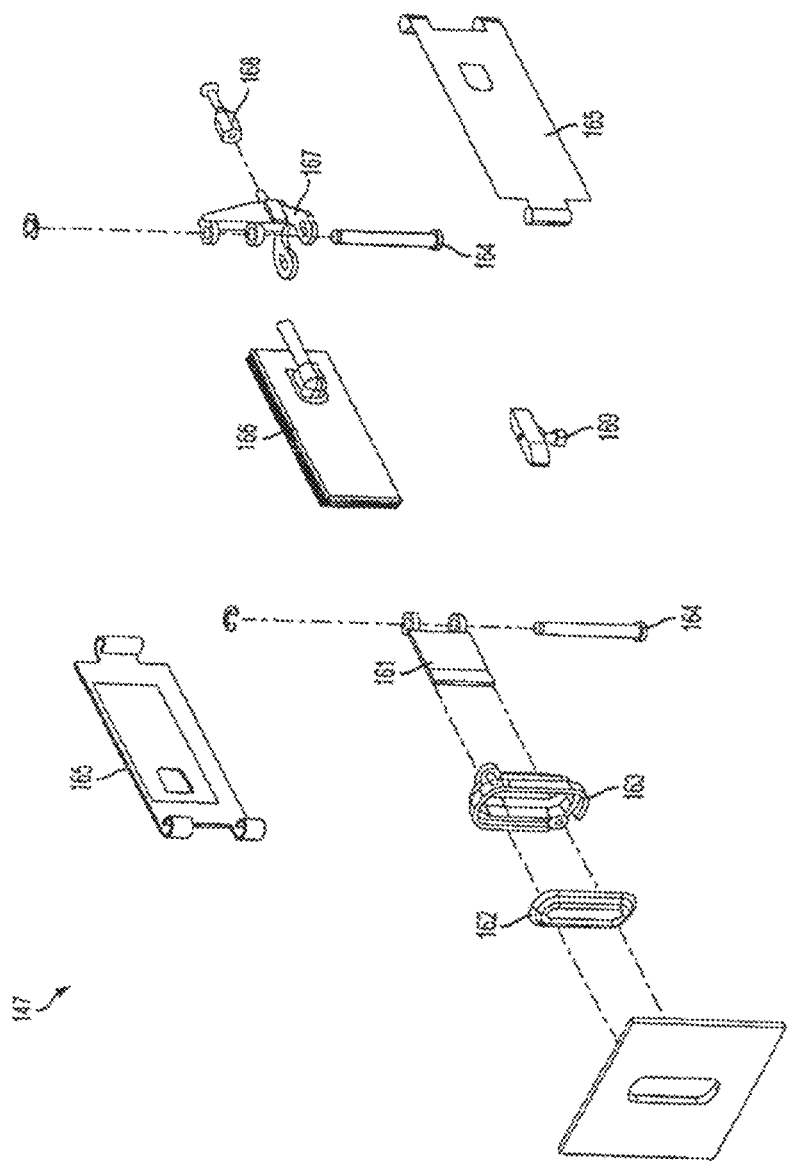
FIG. 30 is an exploded perspective view of an occluder in an illustrative embodiment.

In an embodiment, components that require a relatively constant pressure or vacuum supply during cycler operation, such as an occluder, may be isolated from the source of air pressure/vacuum at least for relatively long periods of time. For example, the occluder 147 in the cycler 14 (shown in FIG. 30) generally requires a constant air pressure in the occluder bladder 166 so that the patient and drain lines remain open for flow. If the cycler 14 continues to operate properly without power failure, etc., the bladder 166 may be inflated once at the beginning of system operation and remain inflated until shut down. The inventors have recognized that in some circumstances air powered devices that are relatively static, such as the bladder 166, may "creak" or otherwise make noise in response to slight variations in supplied air pressure. Such variations may cause the bladder 166 to change size slightly, which causes associated mechanical parts to move and potentially make noise. In accordance with an aspect of the bladder 166 and other components having similar pneumatic power requirements, may be isolated from the air pump 83 and/or the tanks 84, e.g., by the closing of a valve, so as to reduce variations of pressure in the bladder or other pneumatic component, thus reducing noise that may be generated as a result of pressure variations. Another component that may be isolated from the pneumatic supply is the bladder in the door 141 at the cassette mounting location 145 which inflates to press the cassette 24 against the control gasket 148 when the door 141 is closed. Other suitable components may be isolated as desired.

In another embodiment, the speed and/or force at which pneumatic components are actuated may be controlled to as to reduce noise generated by component operation. For example, movement of the valve control regions 1481 to move a corresponding portion of the cassette membrane 15 so as to open or close a valve port on the cassette 24 may cause a "popping" noise as the membrane 15 slaps against and/or pull away from the cassette 24. Such noise may be reduced by controlling the rate of operation of the valve control regions 1481, e.g., by restricting the flow rate of air used to move the control regions 1481. Air flow may be restricted by, for example, providing a suitably small sized orifice in the line leading to the associated control chamber, or in other ways.

A controller may also be programmed to apply pulse width modulation ("PWM") to the activation of one or more pneumatic source valves at a manifold of cycler 14. The effect on a pressure tracing associated with a pump chamber can be seen in FIG. 31. The pneumatic pressure delivered to various valves and pumps of cassette 24 can be controlled by causing the associated manifold source valves to open and close repeatedly during the period of actuation of a valve or pump in cassette 24. The rate of rise 2300 or fall 2302 of pressure against membrane 15/control gasket 148 can then be controlled by modulating the duration of the "on" portion of the particular manifold valve during the actuation period. An additional advantage of applying PWM to the manifold source valves is that variable pneumatic pressure can be delivered to the cassette 24 components using only a binary (on-off) source valve, rather than a more expensive and potentially less reliable variable-orifice source valve.

In another embodiment, the movement of one or more valve elements may be suitably damped so as to reduce noise generated by valve cycling. For example, a fluid (such as a ferro fluid) may be provided with the valve element of high frequency solenoid valves to damp the movement of the element and/or reduce noise generated by movement of the valve element between open and closed positions.

In another embodiment, pneumatic control line vents may be connected together and/or routed into a common, sound-insulated space so that noise associated with air pressure or vacuum release may be reduced. For example, when the occluder bladder 166 is vented to allow the spring plates 165 (see, for example, FIG. 30) to move toward each other and occlude one or more lines, the air pressure released may be released into a sound insulated enclosure, as opposed to being released into a space where noise associated with the release may be heard more easily. In another embodiment, lines that are arranged to release air pressure may be connected together with lines that are arranged to release an air vacuum. With this connection (which may include a vent to atmosphere, an accumulator or other), noise generated by pressure/vacuum release may be further reduced.

The invention claimed is:

1. A gasket for actuating a pump cassette,
the gasket having a first side configured for placement against a pressure delivery block and having an opposing second side configured for placement against a flexible cassette membrane overlying the pump cassette, the gasket having a main body and an elastomeric valve control region that moves outward toward the cassette under positive pressure and inward toward the pressure delivery block under negative pressure;
the valve control region configured to be positioned adjacent a valve actuation portion of the cassette membrane overlying a cassette valve of the pump cassette;
the valve control region comprising:
a central portion configured to align with and to be pressed against a valve seat defining an orifice of the cassette valve;
a peripheral portion configured to extend over a valve chamber of the pump cassette surrounding the valve orifice;
a vacuum channel forming a perimeter around at least a portion of the peripheral portion of the valve control region, the vacuum channel defined by an inner wall contiguous with the peripheral portion of the valve control region, a floor, and an outer wall contiguous with or formed from the main body of the gasket, the vacuum channel being open to the second side of the gasket;

the vacuum channel fluidically connected to a vacuum port in the gasket that penetrates from the second side to the first side of the gasket, the vacuum port configured to communicate with a corresponding pressure delivery block vacuum port when the gasket is positioned against the pressure delivery block;

wherein the inner wall of the vacuum channel is configured to flex toward the pressure delivery block when the valve control region is placed under negative pressure, at least partially collapsing the inner wall of the vacuum channel while the valve control region moves inward and is pulled away from the cassette valve orifice when the pump cassette is present against the gasket.

2. The gasket of claim 1, wherein the cassette valve seat comprises a raised circumferential wall, and wherein the valve control region is configured to press the cassette membrane against the circumferential wall to occlude or close the cassette valve.

3. The gasket of claim 2, wherein the vacuum channel of the valve control region is configured to be positioned outside the circumferential wall of the valve seat and over the valve chamber of the cassette valve.

4. The gasket of claim 3, wherein the inner and outer walls of the vacuum channel are configured to apply pressure between the valve control region and the valve seat when the first side of the valve actuation region is exposed to atmospheric pressure and the pump cassette is placed against the gasket.

5. A fluid pumping system comprising:
a pump cassette comprising a flexible membrane and a membrane based valve;
a base pumping unit comprising a source of positive or negative pressure, a pressure distribution manifold, and a pressure delivery block configured to be positioned adjacent the cassette membrane and valve;
a gasket configured for placement between the pressure delivery block and the cassette membrane, a first side of the gasket positioned against the pressure delivery block and a second opposing side of the gasket positioned against the cassette, the gasket comprising an elastomeric valve control region for positioning against the cassette membrane and valve;

the pressure delivery block comprising a control port for delivering positive pressure to the valve control region to move the cassette membrane against a valve seat of the cassette valve, and for delivering negative pressure to the valve control region to move the cassette membrane away from the valve seat of the cassette valve;

the gasket comprising a vacuum channel forming a perimeter around at least a portion of the valve control region, the vacuum channel defined by an inner wall contiguous with the valve control region, a floor, and an outer wall contiguous with or formed from a non-actuation region of the gasket surrounding the valve actuation region;

the vacuum channel in communication with a vacuum port in the gasket that penetrates from the second side to the first side of the gasket and that is aligned with a pressure delivery block vacuum port;

wherein the inner wall of the vacuum channel is configured to flex toward the pressure delivery block when negative pressure is applied to the valve control region via the control port, and patency of the vacuum channel is maintained.

6. The fluid pumping system of claim 5, wherein the positive or negative pressure is pneumatic pressure.

7. The fluid pumping system of claim 5, wherein the vacuum channel is positioned circumferentially around the periphery of the valve control region.

8. The fluid pumping system of claim 5, wherein the cassette valve seat comprises a raised circumferential wall, and wherein the valve control region is configured to press the cassette membrane against the circumferential wall to occlude or close the cassette valve.

9. The fluid pumping system of claim 8, wherein the vacuum channel of the valve actuation region is positioned outside the circumferential wall of the valve seat and over the valve chamber of the cassette valve.

10. The fluid pumping system of claim 9, wherein the inner and outer walls of the vacuum channel are configured to apply pressure between the valve control region and the valve seat when the first side of the valve control region is exposed to atmospheric or ambient pressure.

* * * * *